US012649780B2

(12) United States Patent
Fiorina et al.

(10) Patent No.: US 12,649,780 B2
(45) Date of Patent: Jun. 9, 2026

(54) METHODS FOR TREATING DIABETIC KIDNEY DISEASE AND GLOMERULAR DISEASE

(71) Applicant: Nephris SrL, Milan (IT)

(72) Inventors: Paolo Fiorina, Boston, MA (US);
Francesca D'Addio, Milan (IT)

(73) Assignee: Nephris SrL, Milan (IT)

( * ) Notice: Subject to any disclaimer, the term of this patent is extended or adjusted under 35 U.S.C. 154(b) by 0 days.

(21) Appl. No.: 19/281,468

(22) Filed: Jul. 25, 2025

(65) Prior Publication Data

US 2025/0346656 A1      Nov. 13, 2025

Related U.S. Application Data

(63) Continuation of application No. 18/292,826, filed as application No. PCT/EP2022/071139 on Jul. 27, 2022, now abandoned.

(60) Provisional application No. 63/302,460, filed on Jan. 24, 2022, provisional application No. 63/226,125, filed on Jul. 27, 2021.

(51) Int. Cl.
| | |
|---|---|
| *C07K 16/00* | (2006.01) |
| *A61K 39/395* | (2006.01) |
| *A61P 13/12* | (2006.01) |
| *C07K 16/18* | (2006.01) |
| *A61K 39/00* | (2006.01) |

(52) U.S. Cl.
CPC .............. *C07K 16/18* (2013.01); *A61P 13/12* (2018.01); *A61K 2039/505* (2013.01); *C07K 2317/24* (2013.01); *C07K 2317/52* (2013.01); *C07K 2317/55* (2013.01); *C07K 2317/565* (2013.01); *C07K 2317/567* (2013.01); *C07K*

*2317/71* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| | | | |
|---|---|---|---|
| WO | WO 2009/105548 A2 | | 8/2009 |
| WO | WO/2020/018005 | * | 1/2020 |

OTHER PUBLICATIONS

Nolan, K., et al., "Structure of neuroblastoma suppressor of tumorigenicity 1 (NBL1): insights for the functional variability across bone morphogenetic protein (BMP) antagonists," J Biol Chem 290, Feb. 20, 2015, pp. 4759-4771.
PCT International Search Report and Written Opinion, PCT Application No. PCT/EP2022/071139, Jan. 12, 2023, 22 pages.
Zhang, Y. et al., "Bone morphogenetic protein-7 and Gremlin: New emerging therapeutic targets for diabetic nephropathy," Biochemical and Biophysical Research Communications 383(1), May 22, 2009, pp. 1-3.

* cited by examiner

*Primary Examiner* — Meera Natarajan
(74) *Attorney, Agent, or Firm* — Fenwick & West LLP; Dan Becker; Kelly Ndubuka

(57) ABSTRACT

Methods are provided for delaying onset or progression of kidney damage, or treating kidney disease, in a subject who has type 1 diabetes or type 2 diabetes or glomerular disease. The methods comprise administering to a subject with type 1 or type 2 diabetes or glomerular disease an effective amount of an agent capable of inhibiting NBL1 activity, and in particular, capable of inhibiting NBL1-mediated toxicity of human podocytes. In some embodiments, the agent is an antibody capable of binding to human NBL1.

28 Claims, 12 Drawing Sheets

Specification includes a Sequence Listing.

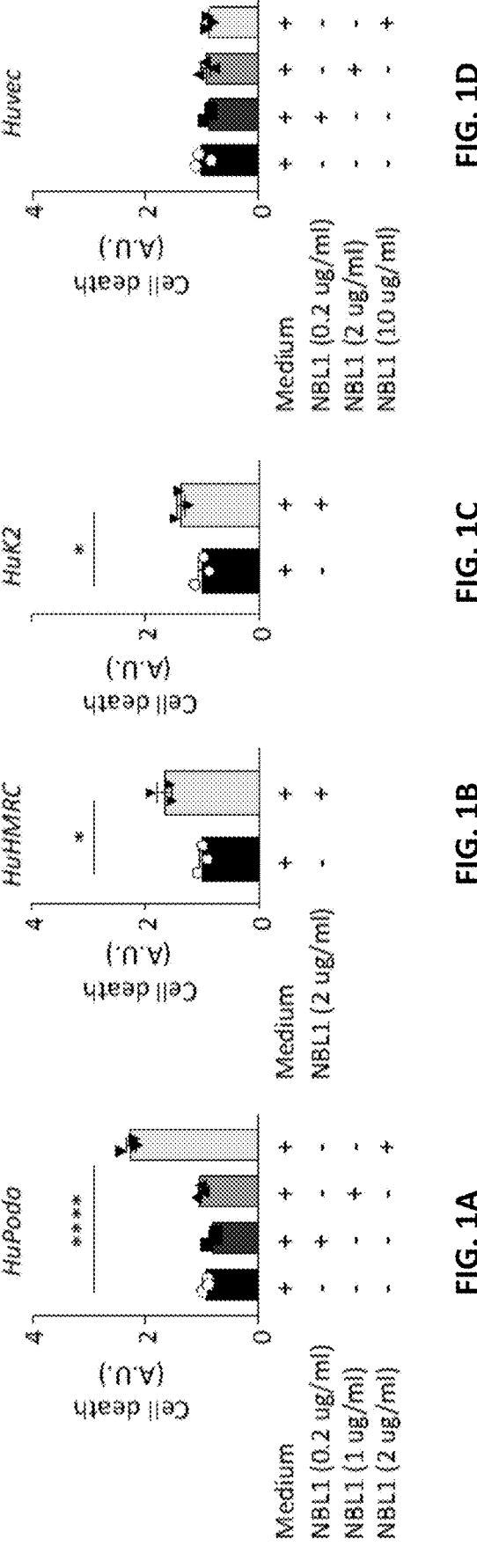

```
SEQUENCE LISTING

Sequence total quantity: 704
SEQ ID NO: 1           moltype = AA  length = 9
FEATURE                Location/Qualifiers
source                 1..9
                       mol_type = protein
                       organism = synthetic construct
SEQUENCE: 1
GGSISSGGY                                                    9

SEQ ID NO: 2           moltype = AA  length = 12
FEATURE                Location/Qualifiers
source                 1..12
                       mol_type = protein
                       organism = synthetic construct
SEQUENCE: 2
GGSISSGGYY WS                                                12

SEQ ID NO: 3           moltype = AA  length = 7
FEATURE                Location/Qualifiers
source                 1..7
                       mol_type = protein
                       organism = synthetic construct
SEQUENCE: 3
SGGYYWS                                                      7
```

```
SEQ ID NO: 4          moltype = AA   length = 8
FEATURE               Location/Qualifiers
source                1..8
                      mol_type = protein
                      organism = synthetic construct
SEQUENCE: 4
SSGGYYWS                                                              8

SEQ ID NO: 5          moltype = AA   length = 10
FEATURE               Location/Qualifiers
source                1..10
                      mol_type = protein
                      organism = synthetic construct
SEQUENCE: 5
GGSISSGGYY                                                            10

SEQ ID NO: 6          moltype = AA   length = 5
FEATURE               Location/Qualifiers
source                1..5
                      mol_type = protein
                      organism = synthetic construct
SEQUENCE: 6
YYSGS                                                                 5

SEQ ID NO: 7          moltype = AA   length = 9
FEATURE               Location/Qualifiers
source                1..9
                      mol_type = protein
                      organism = synthetic construct
SEQUENCE: 7
YIYYSGSTY                                                             9

SEQ ID NO: 8          moltype = AA   length = 16
FEATURE               Location/Qualifiers
source                1..16
                      mol_type = protein
                      organism = synthetic construct
SEQUENCE: 8
YIYYSGSTYY NPSLKS                                                     16

SEQ ID NO: 9          moltype = AA   length = 12
FEATURE               Location/Qualifiers
source                1..12
                      mol_type = protein
                      organism = synthetic construct
SEQUENCE: 9
WIGYIYYSGS TY                                                         12

SEQ ID NO: 10         moltype = AA   length = 7
FEATURE               Location/Qualifiers
source                1..7
                      mol_type = protein
                      organism = synthetic construct
SEQUENCE: 10
IYYSGST                                                               7

SEQ ID NO: 11         moltype = AA   length = 10
FEATURE               Location/Qualifiers
source                1..10
                      mol_type = protein
                      organism = synthetic construct
SEQUENCE: 11
TNSRITMIAD                                                            10

SEQ ID NO: 12         moltype = AA   length = 10
FEATURE               Location/Qualifiers
source                1..10
                      mol_type = protein
                      organism = synthetic construct
SEQUENCE: 12
TNSRITMIAD                                                            10

SEQ ID NO: 13         moltype = AA   length = 10
FEATURE               Location/Qualifiers
source                1..10
                      mol_type = protein
                      organism = synthetic construct
SEQUENCE: 13
TNSRITMIAD                                                            10
```

-continued

```
SEQ ID NO: 14          moltype = AA  length = 11
FEATURE                Location/Qualifiers
source                 1..11
                       mol_type = protein
                       organism = synthetic construct
SEQUENCE: 14
ARTNSRITMI A                                                    11

SEQ ID NO: 15          moltype = AA  length = 12
FEATURE                Location/Qualifiers
source                 1..12
                       mol_type = protein
                       organism = synthetic construct
SEQUENCE: 15
ARTNSRITMI AD                                                   12

SEQ ID NO: 16          moltype = AA  length = 13
FEATURE                Location/Qualifiers
source                 1..13
                       mol_type = protein
                       organism = synthetic construct
SEQUENCE: 16
SGSSSNIGNN YVS                                                  13

SEQ ID NO: 17          moltype = AA  length = 13
FEATURE                Location/Qualifiers
source                 1..13
                       mol_type = protein
                       organism = synthetic construct
SEQUENCE: 17
SGSSSNIGNN YVS                                                  13

SEQ ID NO: 18          moltype = AA  length = 13
FEATURE                Location/Qualifiers
source                 1..13
                       mol_type = protein
                       organism = synthetic construct
SEQUENCE: 18
SGSSSNIGNN YVS                                                  13

SEQ ID NO: 19          moltype = AA  length = 9
FEATURE                Location/Qualifiers
source                 1..9
                       mol_type = protein
                       organism = synthetic construct
SEQUENCE: 19
IGNNYVSWY                                                       9

SEQ ID NO: 20          moltype = AA  length = 8
FEATURE                Location/Qualifiers
source                 1..8
                       mol_type = protein
                       organism = synthetic construct
SEQUENCE: 20
SSNIGNNY                                                        8

SEQ ID NO: 21          moltype = AA  length = 7
FEATURE                Location/Qualifiers
source                 1..7
                       mol_type = protein
                       organism = synthetic construct
SEQUENCE: 21
DNNKRPS                                                         7

SEQ ID NO: 22          moltype = AA  length = 7
FEATURE                Location/Qualifiers
source                 1..7
                       mol_type = protein
                       organism = synthetic construct
SEQUENCE: 22
DNNKRPS                                                         7

SEQ ID NO: 23          moltype = AA  length = 7
FEATURE                Location/Qualifiers
source                 1..7
                       mol_type = protein
                       organism = synthetic construct
SEQUENCE: 23
```

```
DNNKRPS                                                             7

SEQ ID NO: 24        moltype = AA   length = 10
FEATURE              Location/Qualifiers
source               1..10
                     mol_type = protein
                     organism = synthetic construct
SEQUENCE: 24
LLIYDNNKRP                                                          10

SEQ ID NO: 25        moltype =    length =
SEQUENCE: 25
000

SEQ ID NO: 26        moltype = AA   length = 11
FEATURE              Location/Qualifiers
source               1..11
                     mol_type = protein
                     organism = synthetic construct
SEQUENCE: 26
GTWDSSLSAG V                                                        11

SEQ ID NO: 27        moltype = AA   length = 11
FEATURE              Location/Qualifiers
source               1..11
                     mol_type = protein
                     organism = synthetic construct
SEQUENCE: 27
GTWDSSLSAG V                                                        11

SEQ ID NO: 28        moltype = AA   length = 11
FEATURE              Location/Qualifiers
source               1..11
                     mol_type = protein
                     organism = synthetic construct
SEQUENCE: 28
GTWDSSLSAG V                                                        11

SEQ ID NO: 29        moltype = AA   length = 10
FEATURE              Location/Qualifiers
source               1..10
                     mol_type = protein
                     organism = synthetic construct
SEQUENCE: 29
GTWDSSLSAG                                                          10

SEQ ID NO: 30        moltype = AA   length = 11
FEATURE              Location/Qualifiers
source               1..11
                     mol_type = protein
                     organism = synthetic construct
SEQUENCE: 30
GTWDSSLSAG V                                                        11

SEQ ID NO: 31        moltype = AA   length = 9
FEATURE              Location/Qualifiers
source               1..9
                     mol_type = protein
                     organism = synthetic construct
SEQUENCE: 31
GGSISSGGY                                                           9

SEQ ID NO: 32        moltype = AA   length = 9
FEATURE              Location/Qualifiers
source               1..9
                     mol_type = protein
                     organism = synthetic construct
SEQUENCE: 32
GGSISSGGY                                                           9

SEQ ID NO: 33        moltype = AA   length = 7
FEATURE              Location/Qualifiers
source               1..7
                     mol_type = protein
                     organism = synthetic construct
SEQUENCE: 33
SGGYYWS                                                             7

SEQ ID NO: 34        moltype = AA   length = 8
```

| FEATURE | Location/Qualifiers |
|---|---|
| source | 1..8 |
|  | mol_type = protein |
|  | organism = synthetic construct |

SEQUENCE: 34
SSGGYYWS                                                                           8

| SEQ ID NO: 35 | moltype = AA  length = 10 |
| FEATURE | Location/Qualifiers |
| source | 1..10 |
|  | mol_type = protein |
|  | organism = synthetic construct |

SEQUENCE: 35
GGSISSGGYY                                                                         10

| SEQ ID NO: 36 | moltype = AA  length = 5 |
| FEATURE | Location/Qualifiers |
| source | 1..5 |
|  | mol_type = protein |
|  | organism = synthetic construct |

SEQUENCE: 36
YYSGS                                                                              5

| SEQ ID NO: 37 | moltype = AA  length = 9 |
| FEATURE | Location/Qualifiers |
| source | 1..9 |
|  | mol_type = protein |
|  | organism = synthetic construct |

SEQUENCE: 37
YIYYSGSTY                                                                          9

| SEQ ID NO: 38 | moltype = AA  length = 16 |
| FEATURE | Location/Qualifiers |
| source | 1..16 |
|  | mol_type = protein |
|  | organism = synthetic construct |

SEQUENCE: 38
YIYYSGSTYY NPSLKS                                                                  16

| SEQ ID NO: 39 | moltype = AA  length = 12 |
| FEATURE | Location/Qualifiers |
| source | 1..12 |
|  | mol_type = protein |
|  | organism = synthetic construct |

SEQUENCE: 39
WIGYIYYSGS TY                                                                      12

| SEQ ID NO: 40 | moltype = AA  length = 7 |
| FEATURE | Location/Qualifiers |
| source | 1..7 |
|  | mol_type = protein |
|  | organism = synthetic construct |

SEQUENCE: 40
IYYSGST                                                                            7

| SEQ ID NO: 41 | moltype = AA  length = 10 |
| FEATURE | Location/Qualifiers |
| source | 1..10 |
|  | mol_type = protein |
|  | organism = synthetic construct |

SEQUENCE: 41
TNSRITMIAD                                                                         10

| SEQ ID NO: 42 | moltype = AA  length = 10 |
| FEATURE | Location/Qualifiers |
| source | 1..10 |
|  | mol_type = protein |
|  | organism = synthetic construct |

SEQUENCE: 42
TNSRITMIAD                                                                         10

| SEQ ID NO: 43 | moltype = AA  length = 10 |
| FEATURE | Location/Qualifiers |
| source | 1..10 |
|  | mol_type = protein |
|  | organism = synthetic construct |

SEQUENCE: 43
TNSRITMIAD                                                                         10

-continued

```
SEQ ID NO: 44           moltype = AA   length = 11
FEATURE                 Location/Qualifiers
source                  1..11
                        mol_type = protein
                        organism = synthetic construct
SEQUENCE: 44
ARTNSRITMI A                                                    11

SEQ ID NO: 45           moltype = AA   length = 12
FEATURE                 Location/Qualifiers
source                  1..12
                        mol_type = protein
                        organism = synthetic construct
SEQUENCE: 45
ARTNSRITMI AD                                                   12

SEQ ID NO: 46           moltype = AA   length = 13
FEATURE                 Location/Qualifiers
source                  1..13
                        mol_type = protein
                        organism = synthetic construct
SEQUENCE: 46
SGSSSNIGNN YVS                                                  13

SEQ ID NO: 47           moltype = AA   length = 13
FEATURE                 Location/Qualifiers
source                  1..13
                        mol_type = protein
                        organism = synthetic construct
SEQUENCE: 47
SGSSSNIGNN YVS                                                  13

SEQ ID NO: 48           moltype = AA   length = 13
FEATURE                 Location/Qualifiers
source                  1..13
                        mol_type = protein
                        organism = synthetic construct
SEQUENCE: 48
SGSSSNIGNN YVS                                                  13

SEQ ID NO: 49           moltype = AA   length = 9
FEATURE                 Location/Qualifiers
source                  1..9
                        mol_type = protein
                        organism = synthetic construct
SEQUENCE: 49
IGNNYVSWY                                                       9

SEQ ID NO: 50           moltype = AA   length = 8
FEATURE                 Location/Qualifiers
source                  1..8
                        mol_type = protein
                        organism = synthetic construct
SEQUENCE: 50
SSNIGNNY                                                        8

SEQ ID NO: 51           moltype = AA   length = 7
FEATURE                 Location/Qualifiers
source                  1..7
                        mol_type = protein
                        organism = synthetic construct
SEQUENCE: 51
DNNKRPS                                                         7

SEQ ID NO: 52           moltype = AA   length = 7
FEATURE                 Location/Qualifiers
source                  1..7
                        mol_type = protein
                        organism = synthetic construct
SEQUENCE: 52
DNNKRPS                                                         7

SEQ ID NO: 53           moltype = AA   length = 7
FEATURE                 Location/Qualifiers
source                  1..7
                        mol_type = protein
                        organism = synthetic construct
SEQUENCE: 53
DNNKRPS                                                         7
```

-continued

```
SEQ ID NO: 54          moltype = AA   length = 10
FEATURE                Location/Qualifiers
source                 1..10
                       mol_type = protein
                       organism = synthetic construct
SEQUENCE: 54
LLTYDNNKRP                                                     10

SEQ ID NO: 55          moltype =   length =
SEQUENCE: 55
000

SEQ ID NO: 56          moltype = AA   length = 12
FEATURE                Location/Qualifiers
source                 1..12
                       mol_type = protein
                       organism = synthetic construct
SEQUENCE: 56
GTWDSSLSAG HV                                                  12

SEQ ID NO: 57          moltype = AA   length = 12
FEATURE                Location/Qualifiers
source                 1..12
                       mol_type = protein
                       organism = synthetic construct
SEQUENCE: 57
GTWDSSLSAG HV                                                  12

SEQ ID NO: 58          moltype = AA   length = 12
FEATURE                Location/Qualifiers
source                 1..12
                       mol_type = protein
                       organism = synthetic construct
SEQUENCE: 58
GTWDSSLSAG HV                                                  12

SEQ ID NO: 59          moltype = AA   length = 11
FEATURE                Location/Qualifiers
source                 1..11
                       mol_type = protein
                       organism = synthetic construct
SEQUENCE: 59
GTWDSSLSAG H                                                   11

SEQ ID NO: 60          moltype = AA   length = 12
FEATURE                Location/Qualifiers
source                 1..12
                       mol_type = protein
                       organism = synthetic construct
SEQUENCE: 60
GTWDSSLSAG HV                                                  12

SEQ ID NO: 61          moltype = AA   length = 7
FEATURE                Location/Qualifiers
source                 1..7
                       mol_type = protein
                       organism = synthetic construct
SEQUENCE: 61
GFTFSSY                                                        7

SEQ ID NO: 62          moltype = AA   length = 10
FEATURE                Location/Qualifiers
source                 1..10
                       mol_type = protein
                       organism = synthetic construct
SEQUENCE: 62
GFTFSSYAMS                                                     10

SEQ ID NO: 63          moltype = AA   length = 5
FEATURE                Location/Qualifiers
source                 1..5
                       mol_type = protein
                       organism = synthetic construct
SEQUENCE: 63
SYAMS                                                          5

SEQ ID NO: 64          moltype = AA   length = 6
FEATURE                Location/Qualifiers
```

-continued

```
source                 1..6
                       mol_type = protein
                       organism = synthetic construct
SEQUENCE: 64
SSYAMS                                                                 6

SEQ ID NO: 65          moltype = AA   length = 8
FEATURE                Location/Qualifiers
source                 1..8
                       mol_type = protein
                       organism = synthetic construct
SEQUENCE: 65
GFTFSSYA                                                               8

SEQ ID NO: 66          moltype = AA   length = 6
FEATURE                Location/Qualifiers
source                 1..6
                       mol_type = protein
                       organism = synthetic construct
SEQUENCE: 66
SGSGGS                                                                 6

SEQ ID NO: 67          moltype = AA   length = 10
FEATURE                Location/Qualifiers
source                 1..10
                       mol_type = protein
                       organism = synthetic construct
SEQUENCE: 67
AISGSGGSTY                                                             10

SEQ ID NO: 68          moltype = AA   length = 17
FEATURE                Location/Qualifiers
source                 1..17
                       mol_type = protein
                       organism = synthetic construct
SEQUENCE: 68
AISGSGGSTY YADSVKG                                                     17

SEQ ID NO: 69          moltype = AA   length = 13
FEATURE                Location/Qualifiers
source                 1..13
                       mol_type = protein
                       organism = synthetic construct
SEQUENCE: 69
WVSAISGSGG STY                                                         13

SEQ ID NO: 70          moltype = AA   length = 8
FEATURE                Location/Qualifiers
source                 1..8
                       mol_type = protein
                       organism = synthetic construct
SEQUENCE: 70
ISGSGGST                                                               8

SEQ ID NO: 71          moltype = AA   length = 16
FEATURE                Location/Qualifiers
source                 1..16
                       mol_type = protein
                       organism = synthetic construct
SEQUENCE: 71
GSPYYYDSSG YYPLDY                                                      16

SEQ ID NO: 72          moltype = AA   length = 16
FEATURE                Location/Qualifiers
source                 1..16
                       mol_type = protein
                       organism = synthetic construct
SEQUENCE: 72
GSPYYYDSSG YYPLDY                                                      16

SEQ ID NO: 73          moltype = AA   length = 16
FEATURE                Location/Qualifiers
source                 1..16
                       mol_type = protein
                       organism = synthetic construct
SEQUENCE: 73
GSPYYYDSSG YYPLDY                                                      16

SEQ ID NO: 74          moltype = AA   length = 17
```

-continued

```
FEATURE                Location/Qualifiers
source                 1..17
                       mol_type = protein
                       organism = synthetic construct
SEQUENCE: 74
AKGSPYYYDS SGYYPLD                                          17

SEQ ID NO: 75          moltype = AA  length = 18
FEATURE                Location/Qualifiers
source                 1..18
                       mol_type = protein
                       organism = synthetic construct
SEQUENCE: 75
AKGSPYYYDS SGYYPLDY                                         18

SEQ ID NO: 76          moltype = AA  length = 18
FEATURE                Location/Qualifiers
source                 1..18
                       mol_type = protein
                       organism = synthetic construct
SEQUENCE: 76
AKGSPYYYDS SGYYPLDY                                         18

SEQ ID NO: 77          moltype = AA  length = 16
FEATURE                Location/Qualifiers
source                 1..16
                       mol_type = protein
                       organism = synthetic construct
SEQUENCE: 77
RSSQSLLHSN GYNYLD                                           16

SEQ ID NO: 78          moltype = AA  length = 16
FEATURE                Location/Qualifiers
source                 1..16
                       mol_type = protein
                       organism = synthetic construct
SEQUENCE: 78
RSSQSLLHSN GYNYLD                                           16

SEQ ID NO: 79          moltype = AA  length = 12
FEATURE                Location/Qualifiers
source                 1..12
                       mol_type = protein
                       organism = synthetic construct
SEQUENCE: 79
LHSNGYNYLD WY                                               12

SEQ ID NO: 80          moltype = AA  length = 11
FEATURE                Location/Qualifiers
source                 1..11
                       mol_type = protein
                       organism = synthetic construct
SEQUENCE: 80
QSLLHSNGYN Y                                                11

SEQ ID NO: 81          moltype = AA  length = 7
FEATURE                Location/Qualifiers
source                 1..7
                       mol_type = protein
                       organism = synthetic construct
SEQUENCE: 81
LGSNRAP                                                     7

SEQ ID NO: 82          moltype = AA  length = 7
FEATURE                Location/Qualifiers
source                 1..7
                       mol_type = protein
                       organism = synthetic construct
SEQUENCE: 82
LGSNRAP                                                     7

SEQ ID NO: 83          moltype = AA  length = 7
FEATURE                Location/Qualifiers
source                 1..7
                       mol_type = protein
                       organism = synthetic construct
SEQUENCE: 83
LGSNRAP                                                     7
```

```
SEQ ID NO: 84         moltype = AA  length = 10
FEATURE               Location/Qualifiers
source                1..10
                      mol_type = protein
                      organism = synthetic construct
SEQUENCE: 84
LLIYLGSNRA                                                              10

SEQ ID NO: 85         moltype =   length =
SEQUENCE: 85
000

SEQ ID NO: 86         moltype = AA  length = 9
FEATURE               Location/Qualifiers
source                1..9
                      mol_type = protein
                      organism = synthetic construct
SEQUENCE: 86
MQALQTPLT                                                               9

SEQ ID NO: 87         moltype = AA  length = 9
FEATURE               Location/Qualifiers
source                1..9
                      mol_type = protein
                      organism = synthetic construct
SEQUENCE: 87
MQALQTPLT                                                               9

SEQ ID NO: 88         moltype = AA  length = 9
FEATURE               Location/Qualifiers
source                1..9
                      mol_type = protein
                      organism = synthetic construct
SEQUENCE: 88
MQALQTPLT                                                               9

SEQ ID NO: 89         moltype = AA  length = 8
FEATURE               Location/Qualifiers
source                1..8
                      mol_type = protein
                      organism = synthetic construct
SEQUENCE: 89
MQALQTPL                                                                8

SEQ ID NO: 90         moltype = AA  length = 9
FEATURE               Location/Qualifiers
source                1..9
                      mol_type = protein
                      organism = synthetic construct
SEQUENCE: 90
MQALQTPLT                                                               9

SEQ ID NO: 91         moltype = AA  length = 9
FEATURE               Location/Qualifiers
source                1..9
                      mol_type = protein
                      organism = synthetic construct
SEQUENCE: 91
GGSISSGDY                                                               9

SEQ ID NO: 92         moltype = AA  length = 12
FEATURE               Location/Qualifiers
source                1..12
                      mol_type = protein
                      organism = synthetic construct
SEQUENCE: 92
GGSISSGDYY WS                                                           12

SEQ ID NO: 93         moltype = AA  length = 7
FEATURE               Location/Qualifiers
source                1..7
                      mol_type = protein
                      organism = synthetic construct
SEQUENCE: 93
SGDYYWS                                                                 7

SEQ ID NO: 94         moltype = AA  length = 8
FEATURE               Location/Qualifiers
source                1..8
```

-continued

```
                            mol_type = protein
                            organism = synthetic construct
SEQUENCE: 94
SSGDYYWS                                                        8

SEQ ID NO: 95               moltype = AA   length = 10
FEATURE                     Location/Qualifiers
source                      1..10
                            mol_type = protein
                            organism = synthetic construct
SEQUENCE: 95
GGSISSGDYY                                                     10

SEQ ID NO: 96               moltype = AA   length = 5
FEATURE                     Location/Qualifiers
source                      1..5
                            mol_type = protein
                            organism = synthetic construct
SEQUENCE: 96
YYSGS                                                           5

SEQ ID NO: 97               moltype = AA   length = 9
FEATURE                     Location/Qualifiers
source                      1..9
                            mol_type = protein
                            organism = synthetic construct
SEQUENCE: 97
YIYYSGSTY                                                       9

SEQ ID NO: 98               moltype = AA   length = 16
FEATURE                     Location/Qualifiers
source                      1..16
                            mol_type = protein
                            organism = synthetic construct
SEQUENCE: 98
YIYYSGSTYY NPSLKS                                              16

SEQ ID NO: 99               moltype = AA   length = 12
FEATURE                     Location/Qualifiers
source                      1..12
                            mol_type = protein
                            organism = synthetic construct
SEQUENCE: 99
WIGYIYYSGS TY                                                  12

SEQ ID NO: 100              moltype = AA   length = 7
FEATURE                     Location/Qualifiers
source                      1..7
                            mol_type = protein
                            organism = synthetic construct
SEQUENCE: 100
IYYSGST                                                         7

SEQ ID NO: 101              moltype = AA   length = 8
FEATURE                     Location/Qualifiers
source                      1..8
                            mol_type = protein
                            organism = synthetic construct
SEQUENCE: 101
GRRLLLFH                                                        8

SEQ ID NO: 102              moltype = AA   length = 8
FEATURE                     Location/Qualifiers
source                      1..8
                            mol_type = protein
                            organism = synthetic construct
SEQUENCE: 102
GRRLLLFH                                                        8

SEQ ID NO: 103              moltype = AA   length = 8
FEATURE                     Location/Qualifiers
source                      1..8
                            mol_type = protein
                            organism = synthetic construct
SEQUENCE: 103
GRRLLLFH                                                        8

SEQ ID NO: 104              moltype = AA   length = 9
FEATURE                     Location/Qualifiers
```

```
source                  1..9
                        mol_type = protein
                        organism = synthetic construct
SEQUENCE: 104
ARGRRLLLF                                                           9

SEQ ID NO: 105          moltype = AA   length = 10
FEATURE                 Location/Qualifiers
source                  1..10
                        mol_type = protein
                        organism = synthetic construct
SEQUENCE: 105
ARGRRLLLFH                                                          10

SEQ ID NO: 106          moltype = AA   length = 13
FEATURE                 Location/Qualifiers
source                  1..13
                        mol_type = protein
                        organism = synthetic construct
SEQUENCE: 106
SGSGSSIGNN YVS                                                      13

SEQ ID NO: 107          moltype = AA   length = 13
FEATURE                 Location/Qualifiers
source                  1..13
                        mol_type = protein
                        organism = synthetic construct
SEQUENCE: 107
SGSGSSIGNN YVS                                                      13

SEQ ID NO: 108          moltype = AA   length = 13
FEATURE                 Location/Qualifiers
source                  1..13
                        mol_type = protein
                        organism = synthetic construct
SEQUENCE: 108
SGSGSSIGNN YVS                                                      13

SEQ ID NO: 109          moltype = AA   length = 9
FEATURE                 Location/Qualifiers
source                  1..9
                        mol_type = protein
                        organism = synthetic construct
SEQUENCE: 109
IGNNYVSWY                                                           9

SEQ ID NO: 110          moltype = AA   length = 8
FEATURE                 Location/Qualifiers
source                  1..8
                        mol_type = protein
                        organism = synthetic construct
SEQUENCE: 110
GSSIGNNY                                                            8

SEQ ID NO: 111          moltype = AA   length = 7
FEATURE                 Location/Qualifiers
source                  1..7
                        mol_type = protein
                        organism = synthetic construct
SEQUENCE: 111
DNNKRAS                                                             7

SEQ ID NO: 112          moltype = AA   length = 7
FEATURE                 Location/Qualifiers
source                  1..7
                        mol_type = protein
                        organism = synthetic construct
SEQUENCE: 112
DNNKRAS                                                             7

SEQ ID NO: 113          moltype = AA   length = 7
FEATURE                 Location/Qualifiers
source                  1..7
                        mol_type = protein
                        organism = synthetic construct
SEQUENCE: 113
DNNKRAS                                                             7

SEQ ID NO: 114          moltype = AA   length = 10
```

-continued

```
FEATURE                  Location/Qualifiers
source                   1..10
                         mol_type = protein
                         organism = synthetic construct
SEQUENCE: 114
LLIYDNNKRA                                                            10

SEQ ID NO: 115           moltype =   length =
SEQUENCE: 115
000

SEQ ID NO: 116           moltype = AA  length = 11
FEATURE                  Location/Qualifiers
source                   1..11
                         mol_type = protein
                         organism = synthetic construct
SEQUENCE: 116
GTWDNSLSAV V                                                          11

SEQ ID NO: 117           moltype = AA  length = 11
FEATURE                  Location/Qualifiers
source                   1..11
                         mol_type = protein
                         organism = synthetic construct
SEQUENCE: 117
GTWDNSLSAV V                                                          11

SEQ ID NO: 118           moltype = AA  length = 11
FEATURE                  Location/Qualifiers
source                   1..11
                         mol_type = protein
                         organism = synthetic construct
SEQUENCE: 118
GTWDNSLSAV V                                                          11

SEQ ID NO: 119           moltype = AA  length = 10
FEATURE                  Location/Qualifiers
source                   1..10
                         mol_type = protein
                         organism = synthetic construct
SEQUENCE: 119
GTWDNSLSAV                                                            10

SEQ ID NO: 120           moltype = AA  length = 11
FEATURE                  Location/Qualifiers
source                   1..11
                         mol_type = protein
                         organism = synthetic construct
SEQUENCE: 120
GTWDNSLSAV V                                                          11

SEQ ID NO: 121           moltype = AA  length = 7
FEATURE                  Location/Qualifiers
source                   1..7
                         mol_type = protein
                         organism = synthetic construct
SEQUENCE: 121
GYTFTSY                                                               7

SEQ ID NO: 122           moltype = AA  length = 10
FEATURE                  Location/Qualifiers
source                   1..10
                         mol_type = protein
                         organism = synthetic construct
SEQUENCE: 122
GYTFTSYAMH                                                            10

SEQ ID NO: 123           moltype = AA  length = 5
FEATURE                  Location/Qualifiers
source                   1..5
                         mol_type = protein
                         organism = synthetic construct
SEQUENCE: 123
SYAMH                                                                 5

SEQ ID NO: 124           moltype = AA  length = 6
FEATURE                  Location/Qualifiers
source                   1..6
                         mol_type = protein
```

-continued

```
                              organism = synthetic construct
SEQUENCE: 124
TSYAMH                                                                          6

SEQ ID NO: 125           moltype = AA   length = 8
FEATURE                  Location/Qualifiers
source                   1..8
                         mol_type = protein
                         organism = synthetic construct
SEQUENCE: 125
GYTFTSYA                                                                        8

SEQ ID NO: 126           moltype = AA   length = 6
FEATURE                  Location/Qualifiers
source                   1..6
                         mol_type = protein
                         organism = synthetic construct
SEQUENCE: 126
NAGNGN                                                                          6

SEQ ID NO: 127           moltype = AA   length = 10
FEATURE                  Location/Qualifiers
source                   1..10
                         mol_type = protein
                         organism = synthetic construct
SEQUENCE: 127
WINAGNGNTK                                                                      10

SEQ ID NO: 128           moltype = AA   length = 17
FEATURE                  Location/Qualifiers
source                   1..17
                         mol_type = protein
                         organism = synthetic construct
SEQUENCE: 128
WINAGNGNTK YSQKFQG                                                              17

SEQ ID NO: 129           moltype = AA   length = 13
FEATURE                  Location/Qualifiers
source                   1..13
                         mol_type = protein
                         organism = synthetic construct
SEQUENCE: 129
WMGWINAGNG NTK                                                                  13

SEQ ID NO: 130           moltype = AA   length = 8
FEATURE                  Location/Qualifiers
source                   1..8
                         mol_type = protein
                         organism = synthetic construct
SEQUENCE: 130
INAGNGNT                                                                        8

SEQ ID NO: 131           moltype = AA   length = 9
FEATURE                  Location/Qualifiers
source                   1..9
                         mol_type = protein
                         organism = synthetic construct
SEQUENCE: 131
GRELLTFDY                                                                       9

SEQ ID NO: 132           moltype = AA   length = 9
FEATURE                  Location/Qualifiers
source                   1..9
                         mol_type = protein
                         organism = synthetic construct
SEQUENCE: 132
GRELLTFDY                                                                       9

SEQ ID NO: 133           moltype = AA   length = 9
FEATURE                  Location/Qualifiers
source                   1..9
                         mol_type = protein
                         organism = synthetic construct
SEQUENCE: 133
GRELLTFDY                                                                       9

SEQ ID NO: 134           moltype = AA   length = 10
FEATURE                  Location/Qualifiers
source                   1..10
```

-continued

```
                         mol_type = protein
                         organism = synthetic construct
SEQUENCE: 134
ARGRELLTFD                                                            10

SEQ ID NO: 135           moltype = AA   length = 11
FEATURE                  Location/Qualifiers
source                   1..11
                         mol_type = protein
                         organism = synthetic construct
SEQUENCE: 135
ARGRELLTFD Y                                                          11

SEQ ID NO: 136           moltype = AA   length = 16
FEATURE                  Location/Qualifiers
source                   1..16
                         mol_type = protein
                         organism = synthetic construct
SEQUENCE: 136
RSSQSLLHSN GYNYLD                                                     16

SEQ ID NO: 137           moltype = AA   length = 16
FEATURE                  Location/Qualifiers
source                   1..16
                         mol_type = protein
                         organism = synthetic construct
SEQUENCE: 137
RSSQSLLHSN GYNYLD                                                     16

SEQ ID NO: 138           moltype = AA   length = 16
FEATURE                  Location/Qualifiers
source                   1..16
                         mol_type = protein
                         organism = synthetic construct
SEQUENCE: 138
RSSQSLLHSN GYNYLD                                                     16

SEQ ID NO: 139           moltype = AA   length = 12
FEATURE                  Location/Qualifiers
source                   1..12
                         mol_type = protein
                         organism = synthetic construct
SEQUENCE: 139
LHSNGYNYLD WY                                                         12

SEQ ID NO: 140           moltype = AA   length = 11
FEATURE                  Location/Qualifiers
source                   1..11
                         mol_type = protein
                         organism = synthetic construct
SEQUENCE: 140
QSLLHSNGYN Y                                                          11

SEQ ID NO: 141           moltype = AA   length = 7
FEATURE                  Location/Qualifiers
source                   1..7
                         mol_type = protein
                         organism = synthetic construct
SEQUENCE: 141
LGSNRAS                                                               7

SEQ ID NO: 142           moltype = AA   length = 7
FEATURE                  Location/Qualifiers
source                   1..7
                         mol_type = protein
                         organism = synthetic construct
SEQUENCE: 142
LGSNRAS                                                               7

SEQ ID NO: 143           moltype = AA   length = 7
FEATURE                  Location/Qualifiers
source                   1..7
                         mol_type = protein
                         organism = synthetic construct
SEQUENCE: 143
LGSNRAS                                                               7

SEQ ID NO: 144           moltype = AA   length = 10
FEATURE                  Location/Qualifiers
```

-continued

```
source                  1..10
                        mol_type = protein
                        organism = synthetic construct
SEQUENCE: 144
LLIYLGSNRA                                                          10

SEQ ID NO: 145          moltype =   length =
SEQUENCE: 145
000

SEQ ID NO: 146          moltype = AA  length = 9
FEATURE                 Location/Qualifiers
source                  1..9
                        mol_type = protein
                        organism = synthetic construct
SEQUENCE: 146
MQALQTPLT                                                           9

SEQ ID NO: 147          moltype = AA  length = 9
FEATURE                 Location/Qualifiers
source                  1..9
                        mol_type = protein
                        organism = synthetic construct
SEQUENCE: 147
MQALQTPLT                                                           9

SEQ ID NO: 148          moltype = AA  length = 9
FEATURE                 Location/Qualifiers
source                  1..9
                        mol_type = protein
                        organism = synthetic construct
SEQUENCE: 148
MQALQTPLT                                                           9

SEQ ID NO: 149          moltype = AA  length = 8
FEATURE                 Location/Qualifiers
source                  1..8
                        mol_type = protein
                        organism = synthetic construct
SEQUENCE: 149
MQALQTPL                                                            8

SEQ ID NO: 150          moltype = AA  length = 9
FEATURE                 Location/Qualifiers
source                  1..9
                        mol_type = protein
                        organism = synthetic construct
SEQUENCE: 150
MQALQTPLT                                                           9

SEQ ID NO: 151          moltype = AA  length = 9
FEATURE                 Location/Qualifiers
source                  1..9
                        mol_type = protein
                        organism = synthetic construct
SEQUENCE: 151
GGSISSGGY                                                           9

SEQ ID NO: 152          moltype = AA  length = 12
FEATURE                 Location/Qualifiers
source                  1..12
                        mol_type = protein
                        organism = synthetic construct
SEQUENCE: 152
GGSISSGGYY WS                                                       12

SEQ ID NO: 153          moltype = AA  length = 7
FEATURE                 Location/Qualifiers
source                  1..7
                        mol_type = protein
                        organism = synthetic construct
SEQUENCE: 153
SGGYYWS                                                             7

SEQ ID NO: 154          moltype = AA  length = 8
FEATURE                 Location/Qualifiers
source                  1..8
                        mol_type = protein
                        organism = synthetic construct
```

-continued

```
SEQUENCE: 154
SSGGYYWS                                                                   8

SEQ ID NO: 155        moltype = AA  length = 10
FEATURE               Location/Qualifiers
source                1..10
                      mol_type = protein
                      organism = synthetic construct
SEQUENCE: 155
GGSISSGGYY                                                                10

SEQ ID NO: 156        moltype = AA  length = 5
FEATURE               Location/Qualifiers
source                1..5
                      mol_type = protein
                      organism = synthetic construct
SEQUENCE: 156
YYSGS                                                                      5

SEQ ID NO: 157        moltype = AA  length = 9
FEATURE               Location/Qualifiers
source                1..9
                      mol_type = protein
                      organism = synthetic construct
SEQUENCE: 157
YIYYSGSTY                                                                  9

SEQ ID NO: 158        moltype = AA  length = 16
FEATURE               Location/Qualifiers
source                1..16
                      mol_type = protein
                      organism = synthetic construct
SEQUENCE: 158
YIYYSGSTYY NPSLKS                                                         16

SEQ ID NO: 159        moltype = AA  length = 12
FEATURE               Location/Qualifiers
source                1..12
                      mol_type = protein
                      organism = synthetic construct
SEQUENCE: 159
WIGYIYYSGS TY                                                             12

SEQ ID NO: 160        moltype = AA  length = 7
FEATURE               Location/Qualifiers
source                1..7
                      mol_type = protein
                      organism = synthetic construct
SEQUENCE: 160
IYYSGST                                                                    7

SEQ ID NO: 161        moltype = AA  length = 11
FEATURE               Location/Qualifiers
source                1..11
                      mol_type = protein
                      organism = synthetic construct
SEQUENCE: 161
DAPLRIGAFD I                                                              11

SEQ ID NO: 162        moltype = AA  length = 11
FEATURE               Location/Qualifiers
source                1..11
                      mol_type = protein
                      organism = synthetic construct
SEQUENCE: 162
DAPLRIGAFD I                                                              11

SEQ ID NO: 163        moltype = AA  length = 11
FEATURE               Location/Qualifiers
source                1..11
                      mol_type = protein
                      organism = synthetic construct
SEQUENCE: 163
DAPLRIGAFD I                                                              11

SEQ ID NO: 164        moltype = AA  length = 12
FEATURE               Location/Qualifiers
source                1..12
                      mol_type = protein
```

-continued

```
                            organism = synthetic construct
SEQUENCE: 164
ARDAPLRIGA FD                                                               12

SEQ ID NO: 165              moltype = AA   length = 13
FEATURE                     Location/Qualifiers
source                      1..13
                            mol_type = protein
                            organism = synthetic construct
SEQUENCE: 165
ARDAPLRIGA FDI                                                              13

SEQ ID NO: 166              moltype = AA   length = 13
FEATURE                     Location/Qualifiers
source                      1..13
                            mol_type = protein
                            organism = synthetic construct
SEQUENCE: 166
SGSSSNIGNN YVS                                                              13

SEQ ID NO: 167              moltype = AA   length = 13
FEATURE                     Location/Qualifiers
source                      1..13
                            mol_type = protein
                            organism = synthetic construct
SEQUENCE: 167
SGSSSNIGNN YVS                                                              13

SEQ ID NO: 168              moltype = AA   length = 13
FEATURE                     Location/Qualifiers
source                      1..13
                            mol_type = protein
                            organism = synthetic construct
SEQUENCE: 168
SGSSSNIGNN YVS                                                              13

SEQ ID NO: 169              moltype = AA   length = 9
FEATURE                     Location/Qualifiers
source                      1..9
                            mol_type = protein
                            organism = synthetic construct
SEQUENCE: 169
IGNNYVSWY                                                                    9

SEQ ID NO: 170              moltype = AA   length = 8
FEATURE                     Location/Qualifiers
source                      1..8
                            mol_type = protein
                            organism = synthetic construct
SEQUENCE: 170
SSNIGNNY                                                                     8

SEQ ID NO: 171              moltype = AA   length = 7
FEATURE                     Location/Qualifiers
source                      1..7
                            mol_type = protein
                            organism = synthetic construct
SEQUENCE: 171
DNNKRPS                                                                      7

SEQ ID NO: 172              moltype = AA   length = 7
FEATURE                     Location/Qualifiers
source                      1..7
                            mol_type = protein
                            organism = synthetic construct
SEQUENCE: 172
DNNKRPS                                                                      7

SEQ ID NO: 173              moltype = AA   length = 7
FEATURE                     Location/Qualifiers
source                      1..7
                            mol_type = protein
                            organism = synthetic construct
SEQUENCE: 173
DNNKRPS                                                                      7

SEQ ID NO: 174              moltype = AA   length = 10
FEATURE                     Location/Qualifiers
source                      1..10
```

-continued

```
                              mol_type = protein
                              organism = synthetic construct
SEQUENCE: 174
LLIYDNNKRP                                                         10

SEQ ID NO: 175       moltype =    length =
SEQUENCE: 175
000

SEQ ID NO: 176       moltype = AA   length = 11
FEATURE              Location/Qualifiers
source               1..11
                     mol_type = protein
                     organism = synthetic construct
SEQUENCE: 176
GTWDSSLSAG V                                                       11

SEQ ID NO: 177       moltype = AA   length = 11
FEATURE              Location/Qualifiers
source               1..11
                     mol_type = protein
                     organism = synthetic construct
SEQUENCE: 177
GTWDSSLSAG V                                                       11

SEQ ID NO: 178       moltype = AA   length = 11
FEATURE              Location/Qualifiers
source               1..11
                     mol_type = protein
                     organism = synthetic construct
SEQUENCE: 178
GTWDSSLSAG V                                                       11

SEQ ID NO: 179       moltype = AA   length = 10
FEATURE              Location/Qualifiers
source               1..10
                     mol_type = protein
                     organism = synthetic construct
SEQUENCE: 179
GTWDSSLSAG                                                         10

SEQ ID NO: 180       moltype = AA   length = 11
FEATURE              Location/Qualifiers
source               1..11
                     mol_type = protein
                     organism = synthetic construct
SEQUENCE: 180
GTWDSSLSAG V                                                       11

SEQ ID NO: 181       moltype = AA   length = 7
FEATURE              Location/Qualifiers
source               1..7
                     mol_type = protein
                     organism = synthetic construct
SEQUENCE: 181
GFTFSSY                                                            7

SEQ ID NO: 182       moltype = AA   length = 10
FEATURE              Location/Qualifiers
source               1..10
                     mol_type = protein
                     organism = synthetic construct
SEQUENCE: 182
GFTFSSYAMH                                                         10

SEQ ID NO: 183       moltype = AA   length = 5
FEATURE              Location/Qualifiers
source               1..5
                     mol_type = protein
                     organism = synthetic construct
SEQUENCE: 183
SYAMH                                                              5

SEQ ID NO: 184       moltype = AA   length = 6
FEATURE              Location/Qualifiers
source               1..6
                     mol_type = protein
                     organism = synthetic construct
SEQUENCE: 184
```

```
SSYAMH                                                        6

SEQ ID NO: 185          moltype = AA   length = 8
FEATURE                 Location/Qualifiers
source                  1..8
                        mol_type = protein
                        organism = synthetic construct
SEQUENCE: 185
GFTFSSYA                                                      8

SEQ ID NO: 186          moltype = AA   length = 6
FEATURE                 Location/Qualifiers
source                  1..6
                        mol_type = protein
                        organism = synthetic construct
SEQUENCE: 186
SYDGSN                                                        6

SEQ ID NO: 187          moltype = AA   length = 10
FEATURE                 Location/Qualifiers
source                  1..10
                        mol_type = protein
                        organism = synthetic construct
SEQUENCE: 187
VISYDGSNKY                                                    10

SEQ ID NO: 188          moltype = AA   length = 17
FEATURE                 Location/Qualifiers
source                  1..17
                        mol_type = protein
                        organism = synthetic construct
SEQUENCE: 188
VISYDGSNKY YADSVKG                                            17

SEQ ID NO: 189          moltype = AA   length = 13
FEATURE                 Location/Qualifiers
source                  1..13
                        mol_type = protein
                        organism = synthetic construct
SEQUENCE: 189
WVAVISYDGS NKY                                                13

SEQ ID NO: 190          moltype = AA   length = 8
FEATURE                 Location/Qualifiers
source                  1..8
                        mol_type = protein
                        organism = synthetic construct
SEQUENCE: 190
ISYDGSNK                                                      8

SEQ ID NO: 191          moltype = AA   length = 12
FEATURE                 Location/Qualifiers
source                  1..12
                        mol_type = protein
                        organism = synthetic construct
SEQUENCE: 191
PVLRYFDWLP NY                                                 12

SEQ ID NO: 192          moltype = AA   length = 12
FEATURE                 Location/Qualifiers
source                  1..12
                        mol_type = protein
                        organism = synthetic construct
SEQUENCE: 192
PVLRYFDWLP NY                                                 12

SEQ ID NO: 193          moltype = AA   length = 12
FEATURE                 Location/Qualifiers
source                  1..12
                        mol_type = protein
                        organism = synthetic construct
SEQUENCE: 193
PVLRYFDWLP NY                                                 12

SEQ ID NO: 194          moltype = AA   length = 13
FEATURE                 Location/Qualifiers
source                  1..13
                        mol_type = protein
                        organism = synthetic construct
```

-continued

```
SEQUENCE: 194
ASPVLRYFDW LPN                                                            13

SEQ ID NO: 195          moltype = AA  length = 14
FEATURE                 Location/Qualifiers
source                  1..14
                        mol_type = protein
                        organism = synthetic construct
SEQUENCE: 195
ASPVLRYFDW LPNY                                                           14

SEQ ID NO: 196          moltype = AA  length = 16
FEATURE                 Location/Qualifiers
source                  1..16
                        mol_type = protein
                        organism = synthetic construct
SEQUENCE: 196
RSSQSLVYSD GNTYLN                                                         16

SEQ ID NO: 197          moltype = AA  length = 16
FEATURE                 Location/Qualifiers
source                  1..16
                        mol_type = protein
                        organism = synthetic construct
SEQUENCE: 197
RSSQSLVYSD GNTYLN                                                         16

SEQ ID NO: 198          moltype = AA  length = 16
FEATURE                 Location/Qualifiers
source                  1..16
                        mol_type = protein
                        organism = synthetic construct
SEQUENCE: 198
RSSQSLVYSD GNTYLN                                                         16

SEQ ID NO: 199          moltype = AA  length = 12
FEATURE                 Location/Qualifiers
source                  1..12
                        mol_type = protein
                        organism = synthetic construct
SEQUENCE: 199
VYSDGNTYLN WF                                                             12

SEQ ID NO: 200          moltype = AA  length = 11
FEATURE                 Location/Qualifiers
source                  1..11
                        mol_type = protein
                        organism = synthetic construct
SEQUENCE: 200
QSLVYSDGNT Y                                                              11

SEQ ID NO: 201          moltype = AA  length = 7
FEATURE                 Location/Qualifiers
source                  1..7
                        mol_type = protein
                        organism = synthetic construct
SEQUENCE: 201
KVSNRDS                                                                   7

SEQ ID NO: 202          moltype = AA  length = 7
FEATURE                 Location/Qualifiers
source                  1..7
                        mol_type = protein
                        organism = synthetic construct
SEQUENCE: 202
KVSNRDS                                                                   7

SEQ ID NO: 203          moltype = AA  length = 7
FEATURE                 Location/Qualifiers
source                  1..7
                        mol_type = protein
                        organism = synthetic construct
SEQUENCE: 203
KVSNRDS                                                                   7

SEQ ID NO: 204          moltype = AA  length = 10
FEATURE                 Location/Qualifiers
source                  1..10
                        mol_type = protein
```

-continued

```
SEQUENCE: 204
RLIYKVSNRD                                                              10

SEQ ID NO: 205          moltype =    length =
SEQUENCE: 205
000

SEQ ID NO: 206          moltype = AA   length = 9
FEATURE                 Location/Qualifiers
source                  1..9
                        mol_type = protein
                        organism = synthetic construct
SEQUENCE: 206
MQGTHWPPA                                                                9

SEQ ID NO: 207          moltype = AA   length = 9
FEATURE                 Location/Qualifiers
source                  1..9
                        mol_type = protein
                        organism = synthetic construct
SEQUENCE: 207
MQGTHWPPA                                                                9

SEQ ID NO: 208          moltype = AA   length = 9
FEATURE                 Location/Qualifiers
source                  1..9
                        mol_type = protein
                        organism = synthetic construct
SEQUENCE: 208
MQGTHWPPA                                                                9

SEQ ID NO: 209          moltype = AA   length = 8
FEATURE                 Location/Qualifiers
source                  1..8
                        mol_type = protein
                        organism = synthetic construct
SEQUENCE: 209
MQGTHWPP                                                                 8

SEQ ID NO: 210          moltype = AA   length = 9
FEATURE                 Location/Qualifiers
source                  1..9
                        mol_type = protein
                        organism = synthetic construct
SEQUENCE: 210
MQGTHWPPA                                                                9

SEQ ID NO: 211          moltype = AA   length = 7
FEATURE                 Location/Qualifiers
source                  1..7
                        mol_type = protein
                        organism = synthetic construct
SEQUENCE: 211
GYTFTSY                                                                  7

SEQ ID NO: 212          moltype = AA   length = 10
FEATURE                 Location/Qualifiers
source                  1..10
                        mol_type = protein
                        organism = synthetic construct
SEQUENCE: 212
GYTFTSYGIS                                                              10

SEQ ID NO: 213          moltype = AA   length = 5
FEATURE                 Location/Qualifiers
source                  1..5
                        mol_type = protein
                        organism = synthetic construct
SEQUENCE: 213
SYGIS                                                                    5

SEQ ID NO: 214          moltype = AA   length = 6
FEATURE                 Location/Qualifiers
source                  1..6
                        mol_type = protein
                        organism = synthetic construct
SEQUENCE: 214
TSYGIS                                                                   6
```

-continued

```
SEQ ID NO: 215            moltype = AA   length = 8
FEATURE                   Location/Qualifiers
source                    1..8
                          mol_type = protein
                          organism = synthetic construct
SEQUENCE: 215
GYTFTSYG                                                         8

SEQ ID NO: 216            moltype = AA   length = 6
FEATURE                   Location/Qualifiers
source                    1..6
                          mol_type = protein
                          organism = synthetic construct
SEQUENCE: 216
SAYNGN                                                           6

SEQ ID NO: 217            moltype = AA   length = 10
FEATURE                   Location/Qualifiers
source                    1..10
                          mol_type = protein
                          organism = synthetic construct
SEQUENCE: 217
WISAYNGNTN                                                       10

SEQ ID NO: 218            moltype = AA   length = 17
FEATURE                   Location/Qualifiers
source                    1..17
                          mol_type = protein
                          organism = synthetic construct
SEQUENCE: 218
WISAYNGNTN YAQKLQG                                               17

SEQ ID NO: 219            moltype = AA   length = 13
FEATURE                   Location/Qualifiers
source                    1..13
                          mol_type = protein
                          organism = synthetic construct
SEQUENCE: 219
WMGWISAYNG NTN                                                   13

SEQ ID NO: 220            moltype = AA   length = 8
FEATURE                   Location/Qualifiers
source                    1..8
                          mol_type = protein
                          organism = synthetic construct
SEQUENCE: 220
ISAYNGNT                                                         8

SEQ ID NO: 221            moltype = AA   length = 11
FEATURE                   Location/Qualifiers
source                    1..11
                          mol_type = protein
                          organism = synthetic construct
SEQUENCE: 221
DVGYSYGIFD Y                                                     11

SEQ ID NO: 222            moltype = AA   length = 11
FEATURE                   Location/Qualifiers
source                    1..11
                          mol_type = protein
                          organism = synthetic construct
SEQUENCE: 222
DVGYSYGIFD Y                                                     11

SEQ ID NO: 223            moltype = AA   length = 11
FEATURE                   Location/Qualifiers
source                    1..11
                          mol_type = protein
                          organism = synthetic construct
SEQUENCE: 223
DVGYSYGIFD Y                                                     11

SEQ ID NO: 224            moltype = AA   length = 12
FEATURE                   Location/Qualifiers
source                    1..12
                          mol_type = protein
                          organism = synthetic construct
SEQUENCE: 224
```

-continued

```
ARDVGYSYGI FD                                                          12

SEQ ID NO: 225          moltype = AA  length = 13
FEATURE                 Location/Qualifiers
source                  1..13
                        mol_type = protein
                        organism = synthetic construct
SEQUENCE: 225
ARDVGYSYGI FDY                                                         13

SEQ ID NO: 226          moltype = AA  length = 16
FEATURE                 Location/Qualifiers
source                  1..16
                        mol_type = protein
                        organism = synthetic construct
SEQUENCE: 226
RSSQSLLHSN GYNYLD                                                      16

SEQ ID NO: 227          moltype = AA  length = 16
FEATURE                 Location/Qualifiers
source                  1..16
                        mol_type = protein
                        organism = synthetic construct
SEQUENCE: 227
RSSQSLLHSN GYNYLD                                                      16

SEQ ID NO: 228          moltype = AA  length = 16
FEATURE                 Location/Qualifiers
source                  1..16
                        mol_type = protein
                        organism = synthetic construct
SEQUENCE: 228
RSSQSLLHSN GYNYLD                                                      16

SEQ ID NO: 229          moltype = AA  length = 12
FEATURE                 Location/Qualifiers
source                  1..12
                        mol_type = protein
                        organism = synthetic construct
SEQUENCE: 229
LHSNGYNYLD WY                                                          12

SEQ ID NO: 230          moltype = AA  length = 11
FEATURE                 Location/Qualifiers
source                  1..11
                        mol_type = protein
                        organism = synthetic construct
SEQUENCE: 230
QSLLHSNGYN Y                                                           11

SEQ ID NO: 231          moltype = AA  length = 7
FEATURE                 Location/Qualifiers
source                  1..7
                        mol_type = protein
                        organism = synthetic construct
SEQUENCE: 231
LGSNRAS                                                                7

SEQ ID NO: 232          moltype = AA  length = 7
FEATURE                 Location/Qualifiers
source                  1..7
                        mol_type = protein
                        organism = synthetic construct
SEQUENCE: 232
LGSNRAS                                                                7

SEQ ID NO: 233          moltype = AA  length = 7
FEATURE                 Location/Qualifiers
source                  1..7
                        mol_type = protein
                        organism = synthetic construct
SEQUENCE: 233
LGSNRAS                                                                7

SEQ ID NO: 234          moltype = AA  length = 10
FEATURE                 Location/Qualifiers
source                  1..10
                        mol_type = protein
                        organism = synthetic construct
```

-continued

```
SEQUENCE: 234
LLIYLGSNRA                                                    10

SEQ ID NO: 235          moltype =   length =
SEQUENCE: 235
000

SEQ ID NO: 236          moltype = AA  length = 9
FEATURE                 Location/Qualifiers
source                  1..9
                        mol_type = protein
                        organism = synthetic construct
SEQUENCE: 236
MQALQTPYT                                                     9

SEQ ID NO: 237          moltype = AA  length = 9
FEATURE                 Location/Qualifiers
source                  1..9
                        mol_type = protein
                        organism = synthetic construct
SEQUENCE: 237
MQALQTPYT                                                     9

SEQ ID NO: 238          moltype = AA  length = 9
FEATURE                 Location/Qualifiers
source                  1..9
                        mol_type = protein
                        organism = synthetic construct
SEQUENCE: 238
MQALQTPYT                                                     9

SEQ ID NO: 239          moltype = AA  length = 8
FEATURE                 Location/Qualifiers
source                  1..8
                        mol_type = protein
                        organism = synthetic construct
SEQUENCE: 239
MQALQTPY                                                      8

SEQ ID NO: 240          moltype = AA  length = 9
FEATURE                 Location/Qualifiers
source                  1..9
                        mol_type = protein
                        organism = synthetic construct
SEQUENCE: 240
MQALQTPYT                                                     9

SEQ ID NO: 241          moltype = AA  length = 7
FEATURE                 Location/Qualifiers
source                  1..7
                        mol_type = protein
                        organism = synthetic construct
SEQUENCE: 241
GYTFTSY                                                       7

SEQ ID NO: 242          moltype = AA  length = 10
FEATURE                 Location/Qualifiers
source                  1..10
                        mol_type = protein
                        organism = synthetic construct
SEQUENCE: 242
GYTFTSYYMH                                                    10

SEQ ID NO: 243          moltype = AA  length = 5
FEATURE                 Location/Qualifiers
source                  1..5
                        mol_type = protein
                        organism = synthetic construct
SEQUENCE: 243
SYYMH                                                         5

SEQ ID NO: 244          moltype = AA  length = 6
FEATURE                 Location/Qualifiers
source                  1..6
                        mol_type = protein
                        organism = synthetic construct
SEQUENCE: 244
TSYYMH                                                        6
```

-continued

```
SEQ ID NO: 245              moltype = AA   length = 8
FEATURE                     Location/Qualifiers
source                      1..8
                            mol_type = protein
                            organism = synthetic construct
SEQUENCE: 245
GYTFTSYY                                                              8

SEQ ID NO: 246              moltype = AA   length = 6
FEATURE                     Location/Qualifiers
source                      1..6
                            mol_type = protein
                            organism = synthetic construct
SEQUENCE: 246
NPSGGS                                                                6

SEQ ID NO: 247              moltype = AA   length = 10
FEATURE                     Location/Qualifiers
source                      1..10
                            mol_type = protein
                            organism = synthetic construct
SEQUENCE: 247
IINPSGGSTS                                                            10

SEQ ID NO: 248              moltype = AA   length = 17
FEATURE                     Location/Qualifiers
source                      1..17
                            mol_type = protein
                            organism = synthetic construct
SEQUENCE: 248
IINPSGGSTS YAQKFQG                                                    17

SEQ ID NO: 249              moltype = AA   length = 13
FEATURE                     Location/Qualifiers
source                      1..13
                            mol_type = protein
                            organism = synthetic construct
SEQUENCE: 249
WMGIINPSGG STS                                                        13

SEQ ID NO: 250              moltype = AA   length = 8
FEATURE                     Location/Qualifiers
source                      1..8
                            mol_type = protein
                            organism = synthetic construct
SEQUENCE: 250
INPSGGST                                                              8

SEQ ID NO: 251              moltype = AA   length = 9
FEATURE                     Location/Qualifiers
source                      1..9
                            mol_type = protein
                            organism = synthetic construct
SEQUENCE: 251
APGKFPLDY                                                             9

SEQ ID NO: 252              moltype = AA   length = 9
FEATURE                     Location/Qualifiers
source                      1..9
                            mol_type = protein
                            organism = synthetic construct
SEQUENCE: 252
APGKFPLDY                                                             9

SEQ ID NO: 253              moltype = AA   length = 9
FEATURE                     Location/Qualifiers
source                      1..9
                            mol_type = protein
                            organism = synthetic construct
SEQUENCE: 253
APGKFPLDY                                                             9

SEQ ID NO: 254              moltype = AA   length = 10
FEATURE                     Location/Qualifiers
source                      1..10
                            mol_type = protein
                            organism = synthetic construct
SEQUENCE: 254
ARAPGKFPLD                                                            10
```

-continued

```
SEQ ID NO: 255            moltype = AA   length = 11
FEATURE                   Location/Qualifiers
source                    1..11
                          mol_type = protein
                          organism = synthetic construct
SEQUENCE: 255
ARAPGKFPLD Y                                               11

SEQ ID NO: 256            moltype = AA   length = 16
FEATURE                   Location/Qualifiers
source                    1..16
                          mol_type = protein
                          organism = synthetic construct
SEQUENCE: 256
RSSQSLLHSN GYNYLD                                          16

SEQ ID NO: 257            moltype = AA   length = 16
FEATURE                   Location/Qualifiers
source                    1..16
                          mol_type = protein
                          organism = synthetic construct
SEQUENCE: 257
RSSQSLLHSN GYNYLD                                          16

SEQ ID NO: 258            moltype = AA   length = 16
FEATURE                   Location/Qualifiers
source                    1..16
                          mol_type = protein
                          organism = synthetic construct
SEQUENCE: 258
RSSQSLLHSN GYNYLD                                          16

SEQ ID NO: 259            moltype = AA   length = 12
FEATURE                   Location/Qualifiers
source                    1..12
                          mol_type = protein
                          organism = synthetic construct
SEQUENCE: 259
LHSNGYNYLD WY                                              12

SEQ ID NO: 260            moltype = AA   length = 11
FEATURE                   Location/Qualifiers
source                    1..11
                          mol_type = protein
                          organism = synthetic construct
SEQUENCE: 260
QSLLHSNGYN Y                                               11

SEQ ID NO: 261            moltype = AA   length = 7
FEATURE                   Location/Qualifiers
source                    1..7
                          mol_type = protein
                          organism = synthetic construct
SEQUENCE: 261
LGSNRAS                                                    7

SEQ ID NO: 262            moltype = AA   length = 7
FEATURE                   Location/Qualifiers
source                    1..7
                          mol_type = protein
                          organism = synthetic construct
SEQUENCE: 262
LGSNRAS                                                    7

SEQ ID NO: 263            moltype = AA   length = 7
FEATURE                   Location/Qualifiers
source                    1..7
                          mol_type = protein
                          organism = synthetic construct
SEQUENCE: 263
LGSNRAS                                                    7

SEQ ID NO: 264            moltype = AA   length = 10
FEATURE                   Location/Qualifiers
source                    1..10
                          mol_type = protein
                          organism = synthetic construct
SEQUENCE: 264
```

-continued

```
LLIYLGSNRA                                                    10

SEQ ID NO: 265       moltype =    length =
SEQUENCE: 265
000

SEQ ID NO: 266       moltype = AA   length = 9
FEATURE              Location/Qualifiers
source               1..9
                     mol_type = protein
                     organism = synthetic construct
SEQUENCE: 266
MQALQTPRT                                                     9

SEQ ID NO: 267       moltype = AA   length = 9
FEATURE              Location/Qualifiers
source               1..9
                     mol_type = protein
                     organism = synthetic construct
SEQUENCE: 267
MQALQTPRT                                                     9

SEQ ID NO: 268       moltype = AA   length = 9
FEATURE              Location/Qualifiers
source               1..9
                     mol_type = protein
                     organism = synthetic construct
SEQUENCE: 268
MQALQTPRT                                                     9

SEQ ID NO: 269       moltype = AA   length = 8
FEATURE              Location/Qualifiers
source               1..8
                     mol_type = protein
                     organism = synthetic construct
SEQUENCE: 269
MQALQTPR                                                      8

SEQ ID NO: 270       moltype = AA   length = 9
FEATURE              Location/Qualifiers
source               1..9
                     mol_type = protein
                     organism = synthetic construct
SEQUENCE: 270
MQALQTPRT                                                     9

SEQ ID NO: 271       moltype = AA   length = 7
FEATURE              Location/Qualifiers
source               1..7
                     mol_type = protein
                     organism = synthetic construct
SEQUENCE: 271
GFTFSSY                                                       7

SEQ ID NO: 272       moltype = AA   length = 10
FEATURE              Location/Qualifiers
source               1..10
                     mol_type = protein
                     organism = synthetic construct
SEQUENCE: 272
GFTFSSYAMS                                                    10

SEQ ID NO: 273       moltype = AA   length = 5
FEATURE              Location/Qualifiers
source               1..5
                     mol_type = protein
                     organism = synthetic construct
SEQUENCE: 273
SYAMS                                                         5

SEQ ID NO: 274       moltype = AA   length = 6
FEATURE              Location/Qualifiers
source               1..6
                     mol_type = protein
                     organism = synthetic construct
SEQUENCE: 274
SSYAMS                                                        6

SEQ ID NO: 275       moltype = AA   length = 8
```

-continued

```
FEATURE              Location/Qualifiers
source               1..8
                     mol_type = protein
                     organism = synthetic construct
SEQUENCE: 275
GFTFSSYA                                                              8

SEQ ID NO: 276       moltype = AA  length = 6
FEATURE              Location/Qualifiers
source               1..6
                     mol_type = protein
                     organism = synthetic construct
SEQUENCE: 276
SGSGGS                                                                6

SEQ ID NO: 277       moltype = AA  length = 10
FEATURE              Location/Qualifiers
source               1..10
                     mol_type = protein
                     organism = synthetic construct
SEQUENCE: 277
AISGSGGSTY                                                           10

SEQ ID NO: 278       moltype = AA  length = 17
FEATURE              Location/Qualifiers
source               1..17
                     mol_type = protein
                     organism = synthetic construct
SEQUENCE: 278
AISGSGGSTY YADSVKG                                                   17

SEQ ID NO: 279       moltype = AA  length = 13
FEATURE              Location/Qualifiers
source               1..13
                     mol_type = protein
                     organism = synthetic construct
SEQUENCE: 279
WVSAISGSGG STY                                                       13

SEQ ID NO: 280       moltype = AA  length = 8
FEATURE              Location/Qualifiers
source               1..8
                     mol_type = protein
                     organism = synthetic construct
SEQUENCE: 280
ISGSGGST                                                              8

SEQ ID NO: 281       moltype = AA  length = 16
FEATURE              Location/Qualifiers
source               1..16
                     mol_type = protein
                     organism = synthetic construct
SEQUENCE: 281
GGFWGSYRYW SAAFDI                                                    16

SEQ ID NO: 282       moltype = AA  length = 16
FEATURE              Location/Qualifiers
source               1..16
                     mol_type = protein
                     organism = synthetic construct
SEQUENCE: 282
GGFWGSYRYW SAAFDI                                                    16

SEQ ID NO: 283       moltype = AA  length = 16
FEATURE              Location/Qualifiers
source               1..16
                     mol_type = protein
                     organism = synthetic construct
SEQUENCE: 283
GGFWGSYRYW SAAFDI                                                    16

SEQ ID NO: 284       moltype = AA  length = 17
FEATURE              Location/Qualifiers
source               1..17
                     mol_type = protein
                     organism = synthetic construct
SEQUENCE: 284
ARGGFWGSYR YWSAAFD                                                   17
```

-continued

```
SEQ ID NO: 285          moltype = AA  length = 18
FEATURE                 Location/Qualifiers
source                  1..18
                        mol_type = protein
                        organism = synthetic construct
SEQUENCE: 285
ARGGFWGSYR YWSAAFDI                                        18

SEQ ID NO: 286          moltype = AA  length = 16
FEATURE                 Location/Qualifiers
source                  1..16
                        mol_type = protein
                        organism = synthetic construct
SEQUENCE: 286
RSSQSLLHSN GYNYLD                                          16

SEQ ID NO: 287          moltype = AA  length = 16
FEATURE                 Location/Qualifiers
source                  1..16
                        mol_type = protein
                        organism = synthetic construct
SEQUENCE: 287
RSSQSLLHSN GYNYLD                                          16

SEQ ID NO: 288          moltype = AA  length = 16
FEATURE                 Location/Qualifiers
source                  1..16
                        mol_type = protein
                        organism = synthetic construct
SEQUENCE: 288
RSSQSLLHSN GYNYLD                                          16

SEQ ID NO: 289          moltype = AA  length = 12
FEATURE                 Location/Qualifiers
source                  1..12
                        mol_type = protein
                        organism = synthetic construct
SEQUENCE: 289
LHSNGYNYLD WY                                              12

SEQ ID NO: 290          moltype = AA  length = 11
FEATURE                 Location/Qualifiers
source                  1..11
                        mol_type = protein
                        organism = synthetic construct
SEQUENCE: 290
QSLLHSNGYN Y                                               11

SEQ ID NO: 291          moltype = AA  length = 7
FEATURE                 Location/Qualifiers
source                  1..7
                        mol_type = protein
                        organism = synthetic construct
SEQUENCE: 291
LGSNRAS                                                    7

SEQ ID NO: 292          moltype = AA  length = 7
FEATURE                 Location/Qualifiers
source                  1..7
                        mol_type = protein
                        organism = synthetic construct
SEQUENCE: 292
LGSNRAS                                                    7

SEQ ID NO: 293          moltype = AA  length = 7
FEATURE                 Location/Qualifiers
source                  1..7
                        mol_type = protein
                        organism = synthetic construct
SEQUENCE: 293
LGSNRAS                                                    7

SEQ ID NO: 294          moltype = AA  length = 10
FEATURE                 Location/Qualifiers
source                  1..10
                        mol_type = protein
                        organism = synthetic construct
SEQUENCE: 294
LLIYLGSNRA                                                 10
```

-continued

```
SEQ ID NO: 295            moltype =    length =
SEQUENCE: 295
000

SEQ ID NO: 296            moltype = AA   length = 9
FEATURE                   Location/Qualifiers
source                    1..9
                          mol_type = protein
                          organism = synthetic construct
SEQUENCE: 296
MQALQTPPT                                                                 9

SEQ ID NO: 297            moltype = AA   length = 9
FEATURE                   Location/Qualifiers
source                    1..9
                          mol_type = protein
                          organism = synthetic construct
SEQUENCE: 297
MQALQTPPT                                                                 9

SEQ ID NO: 298            moltype = AA   length = 9
FEATURE                   Location/Qualifiers
source                    1..9
                          mol_type = protein
                          organism = synthetic construct
SEQUENCE: 298
MQALQTPPT                                                                 9

SEQ ID NO: 299            moltype = AA   length = 8
FEATURE                   Location/Qualifiers
source                    1..8
                          mol_type = protein
                          organism = synthetic construct
SEQUENCE: 299
MQALQTPP                                                                  8

SEQ ID NO: 300            moltype = AA   length = 9
FEATURE                   Location/Qualifiers
source                    1..9
                          mol_type = protein
                          organism = synthetic construct
SEQUENCE: 300
MQALQTPPT                                                                 9

SEQ ID NO: 301            moltype = AA   length = 7
FEATURE                   Location/Qualifiers
source                    1..7
                          mol_type = protein
                          organism = synthetic construct
SEQUENCE: 301
GYTFTSY                                                                   7

SEQ ID NO: 302            moltype = AA   length = 10
FEATURE                   Location/Qualifiers
source                    1..10
                          mol_type = protein
                          organism = synthetic construct
SEQUENCE: 302
GYTFTSYGIT                                                                10

SEQ ID NO: 303            moltype = AA   length = 5
FEATURE                   Location/Qualifiers
source                    1..5
                          mol_type = protein
                          organism = synthetic construct
SEQUENCE: 303
SYGIT                                                                     5

SEQ ID NO: 304            moltype = AA   length = 6
FEATURE                   Location/Qualifiers
source                    1..6
                          mol_type = protein
                          organism = synthetic construct
SEQUENCE: 304
TSYGIT                                                                    6

SEQ ID NO: 305            moltype = AA   length = 8
FEATURE                   Location/Qualifiers
```

-continued

```
source                      1..8
                            mol_type = protein
                            organism = synthetic construct
SEQUENCE: 305
GYTFTSYG                                                                            8

SEQ ID NO: 306              moltype = AA   length = 6
FEATURE                     Location/Qualifiers
source                      1..6
                            mol_type = protein
                            organism = synthetic construct
SEQUENCE: 306
SAYNGN                                                                              6

SEQ ID NO: 307              moltype = AA   length = 10
FEATURE                     Location/Qualifiers
source                      1..10
                            mol_type = protein
                            organism = synthetic construct
SEQUENCE: 307
WISAYNGNTN                                                                          10

SEQ ID NO: 308              moltype = AA   length = 17
FEATURE                     Location/Qualifiers
source                      1..17
                            mol_type = protein
                            organism = synthetic construct
SEQUENCE: 308
WISAYNGNTN YAQKLQG                                                                  17

SEQ ID NO: 309              moltype = AA   length = 13
FEATURE                     Location/Qualifiers
source                      1..13
                            mol_type = protein
                            organism = synthetic construct
SEQUENCE: 309
WMGWISAYNG NTN                                                                      13

SEQ ID NO: 310              moltype = AA   length = 8
FEATURE                     Location/Qualifiers
source                      1..8
                            mol_type = protein
                            organism = synthetic construct
SEQUENCE: 310
ISAYNGT                                                                             8

SEQ ID NO: 311              moltype = AA   length = 14
FEATURE                     Location/Qualifiers
source                      1..14
                            mol_type = protein
                            organism = synthetic construct
SEQUENCE: 311
HHPTGGSATI VFDY                                                                     14

SEQ ID NO: 312              moltype = AA   length = 14
FEATURE                     Location/Qualifiers
source                      1..14
                            mol_type = protein
                            organism = synthetic construct
SEQUENCE: 312
HHPTGGSATI VFDY                                                                     14

SEQ ID NO: 313              moltype = AA   length = 14
FEATURE                     Location/Qualifiers
source                      1..14
                            mol_type = protein
                            organism = synthetic construct
SEQUENCE: 313
HHPTGGSATI VFDY                                                                     14

SEQ ID NO: 314              moltype = AA   length = 15
FEATURE                     Location/Qualifiers
source                      1..15
                            mol_type = protein
                            organism = synthetic construct
SEQUENCE: 314
ARHHPTGGSA TIVFD                                                                    15

SEQ ID NO: 315              moltype = AA   length = 16
```

-continued

```
FEATURE                 Location/Qualifiers
source                  1..16
                        mol_type = protein
                        organism = synthetic construct
SEQUENCE: 315
ARHHPTGGSA TIVFDY                                                    16

SEQ ID NO: 316          moltype = AA  length = 16
FEATURE                 Location/Qualifiers
source                  1..16
                        mol_type = protein
                        organism = synthetic construct
SEQUENCE: 316
RSSQSLLHSN GYNYLD                                                    16

SEQ ID NO: 317          moltype = AA  length = 16
FEATURE                 Location/Qualifiers
source                  1..16
                        mol_type = protein
                        organism = synthetic construct
SEQUENCE: 317
RSSQSLLHSN GYNYLD                                                    16

SEQ ID NO: 318          moltype = AA  length = 16
FEATURE                 Location/Qualifiers
source                  1..16
                        mol_type = protein
                        organism = synthetic construct
SEQUENCE: 318
RSSQSLLHSN GYNYLD                                                    16

SEQ ID NO: 319          moltype = AA  length = 12
FEATURE                 Location/Qualifiers
source                  1..12
                        mol_type = protein
                        organism = synthetic construct
SEQUENCE: 319
LHSNGYNYLD WY                                                        12

SEQ ID NO: 320          moltype = AA  length = 11
FEATURE                 Location/Qualifiers
source                  1..11
                        mol_type = protein
                        organism = synthetic construct
SEQUENCE: 320
QSLLHSNGYN Y                                                         11

SEQ ID NO: 321          moltype = AA  length = 7
FEATURE                 Location/Qualifiers
source                  1..7
                        mol_type = protein
                        organism = synthetic construct
SEQUENCE: 321
LGSNRAS                                                              7

SEQ ID NO: 322          moltype = AA  length = 7
FEATURE                 Location/Qualifiers
source                  1..7
                        mol_type = protein
                        organism = synthetic construct
SEQUENCE: 322
LGSNRAS                                                              7

SEQ ID NO: 323          moltype = AA  length = 7
FEATURE                 Location/Qualifiers
source                  1..7
                        mol_type = protein
                        organism = synthetic construct
SEQUENCE: 323
LGSNRAS                                                              7

SEQ ID NO: 324          moltype = AA  length = 10
FEATURE                 Location/Qualifiers
source                  1..10
                        mol_type = protein
                        organism = synthetic construct
SEQUENCE: 324
LLIYLGSNRA                                                          10
```

```
SEQ ID NO: 325                moltype =   length =
SEQUENCE: 325
000

SEQ ID NO: 326                moltype = AA   length = 9
FEATURE                       Location/Qualifiers
source                        1..9
                              mol_type = protein
                              organism = synthetic construct
SEQUENCE: 326
MQALQTPLT                                                         9

SEQ ID NO: 327                moltype = AA   length = 9
FEATURE                       Location/Qualifiers
source                        1..9
                              mol_type = protein
                              organism = synthetic construct
SEQUENCE: 327
MQALQTPLT                                                         9

SEQ ID NO: 328                moltype = AA   length = 9
FEATURE                       Location/Qualifiers
source                        1..9
                              mol_type = protein
                              organism = synthetic construct
SEQUENCE: 328
MQALQTPLT                                                         9

SEQ ID NO: 329                moltype = AA   length = 8
FEATURE                       Location/Qualifiers
source                        1..8
                              mol_type = protein
                              organism = synthetic construct
SEQUENCE: 329
MQALQTPL                                                          8

SEQ ID NO: 330                moltype = AA   length = 9
FEATURE                       Location/Qualifiers
source                        1..9
                              mol_type = protein
                              organism = synthetic construct
SEQUENCE: 330
MQALQTPLT                                                         9

SEQ ID NO: 331                moltype = AA   length = 7
FEATURE                       Location/Qualifiers
source                        1..7
                              mol_type = protein
                              organism = synthetic construct
SEQUENCE: 331
GYTFTSY                                                           7

SEQ ID NO: 332                moltype = AA   length = 10
FEATURE                       Location/Qualifiers
source                        1..10
                              mol_type = protein
                              organism = synthetic construct
SEQUENCE: 332
GYTFTSYYMH                                                        10

SEQ ID NO: 333                moltype = AA   length = 5
FEATURE                       Location/Qualifiers
source                        1..5
                              mol_type = protein
                              organism = synthetic construct
SEQUENCE: 333
SYYMH                                                             5

SEQ ID NO: 334                moltype = AA   length = 6
FEATURE                       Location/Qualifiers
source                        1..6
                              mol_type = protein
                              organism = synthetic construct
SEQUENCE: 334
TSYYMH                                                            6

SEQ ID NO: 335                moltype = AA   length = 8
FEATURE                       Location/Qualifiers
source                        1..8
```

-continued

```
                        mol_type = protein
                        organism = synthetic construct
SEQUENCE: 335
GYTFTSYY                                                        8

SEQ ID NO: 336          moltype = AA   length = 6
FEATURE                 Location/Qualifiers
source                  1..6
                        mol_type = protein
                        organism = synthetic construct
SEQUENCE: 336
NPSGGS                                                          6

SEQ ID NO: 337          moltype = AA   length = 10
FEATURE                 Location/Qualifiers
source                  1..10
                        mol_type = protein
                        organism = synthetic construct
SEQUENCE: 337
IINPSGGSTS                                                      10

SEQ ID NO: 338          moltype = AA   length = 17
FEATURE                 Location/Qualifiers
source                  1..17
                        mol_type = protein
                        organism = synthetic construct
SEQUENCE: 338
IINPSGGSTS YAQKFQG                                              17

SEQ ID NO: 339          moltype = AA   length = 13
FEATURE                 Location/Qualifiers
source                  1..13
                        mol_type = protein
                        organism = synthetic construct
SEQUENCE: 339
WMGIINPSGG STS                                                  13

SEQ ID NO: 340          moltype = AA   length = 8
FEATURE                 Location/Qualifiers
source                  1..8
                        mol_type = protein
                        organism = synthetic construct
SEQUENCE: 340
INPSGGST                                                        8

SEQ ID NO: 341          moltype = AA   length = 9
FEATURE                 Location/Qualifiers
source                  1..9
                        mol_type = protein
                        organism = synthetic construct
SEQUENCE: 341
APGKFPLDY                                                       9

SEQ ID NO: 342          moltype = AA   length = 9
FEATURE                 Location/Qualifiers
source                  1..9
                        mol_type = protein
                        organism = synthetic construct
SEQUENCE: 342
APGKFPLDY                                                       9

SEQ ID NO: 343          moltype = AA   length = 9
FEATURE                 Location/Qualifiers
source                  1..9
                        mol_type = protein
                        organism = synthetic construct
SEQUENCE: 343
APGKFPLDY                                                       9

SEQ ID NO: 344          moltype = AA   length = 10
FEATURE                 Location/Qualifiers
source                  1..10
                        mol_type = protein
                        organism = synthetic construct
SEQUENCE: 344
ARAPGKFPLD                                                      10

SEQ ID NO: 345          moltype = AA   length = 11
FEATURE                 Location/Qualifiers
```

```
source                    1..11
                          mol_type = protein
                          organism = synthetic construct
SEQUENCE: 345
ARAPGKFPLD Y                                                              11

SEQ ID NO: 346            moltype = AA   length = 16
FEATURE                   Location/Qualifiers
source                    1..16
                          mol_type = protein
                          organism = synthetic construct
SEQUENCE: 346
RSSQSLLHSN GYNYLD                                                         16

SEQ ID NO: 347            moltype = AA   length = 16
FEATURE                   Location/Qualifiers
source                    1..16
                          mol_type = protein
                          organism = synthetic construct
SEQUENCE: 347
RSSQSLLHSN GYNYLD                                                         16

SEQ ID NO: 348            moltype = AA   length = 16
FEATURE                   Location/Qualifiers
source                    1..16
                          mol_type = protein
                          organism = synthetic construct
SEQUENCE: 348
RSSQSLLHSN GYNYLD                                                         16

SEQ ID NO: 349            moltype = AA   length = 12
FEATURE                   Location/Qualifiers
source                    1..12
                          mol_type = protein
                          organism = synthetic construct
SEQUENCE: 349
LHSNGYNYLD WY                                                             12

SEQ ID NO: 350            moltype = AA   length = 11
FEATURE                   Location/Qualifiers
source                    1..11
                          mol_type = protein
                          organism = synthetic construct
SEQUENCE: 350
QSLLHSNGYN Y                                                              11

SEQ ID NO: 351            moltype = AA   length = 7
FEATURE                   Location/Qualifiers
source                    1..7
                          mol_type = protein
                          organism = synthetic construct
SEQUENCE: 351
LGSNRAS                                                                   7

SEQ ID NO: 352            moltype = AA   length = 7
FEATURE                   Location/Qualifiers
source                    1..7
                          mol_type = protein
                          organism = synthetic construct
SEQUENCE: 352
LGSNRAS                                                                   7

SEQ ID NO: 353            moltype = AA   length = 7
FEATURE                   Location/Qualifiers
source                    1..7
                          mol_type = protein
                          organism = synthetic construct
SEQUENCE: 353
LGSNRAS                                                                   7

SEQ ID NO: 354            moltype = AA   length = 10
FEATURE                   Location/Qualifiers
source                    1..10
                          mol_type = protein
                          organism = synthetic construct
SEQUENCE: 354
LLIYLGSNRA                                                                10

SEQ ID NO: 355            moltype =    length =
```

-continued

```
SEQUENCE: 355
000

SEQ ID NO: 356           moltype = AA  length = 8
FEATURE                  Location/Qualifiers
source                   1..8
                         mol_type = protein
                         organism = synthetic construct
SEQUENCE: 356
MQALQTPG                                                           8

SEQ ID NO: 357           moltype = AA  length = 8
FEATURE                  Location/Qualifiers
source                   1..8
                         mol_type = protein
                         organism = synthetic construct
SEQUENCE: 357
MQALQTPG                                                           8

SEQ ID NO: 358           moltype = AA  length = 8
FEATURE                  Location/Qualifiers
source                   1..8
                         mol_type = protein
                         organism = synthetic construct
SEQUENCE: 358
MQALQTPG                                                           8

SEQ ID NO: 359           moltype = AA  length = 7
FEATURE                  Location/Qualifiers
source                   1..7
                         mol_type = protein
                         organism = synthetic construct
SEQUENCE: 359
MQALQTP                                                            7

SEQ ID NO: 360           moltype = AA  length = 8
FEATURE                  Location/Qualifiers
source                   1..8
                         mol_type = protein
                         organism = synthetic construct
SEQUENCE: 360
MQALQTPG                                                           8

SEQ ID NO: 361           moltype = AA  length = 7
FEATURE                  Location/Qualifiers
source                   1..7
                         mol_type = protein
                         organism = synthetic construct
SEQUENCE: 361
GYTFTSY                                                            7

SEQ ID NO: 362           moltype = AA  length = 10
FEATURE                  Location/Qualifiers
source                   1..10
                         mol_type = protein
                         organism = synthetic construct
SEQUENCE: 362
GYTFTSYYMH                                                         10

SEQ ID NO: 363           moltype = AA  length = 5
FEATURE                  Location/Qualifiers
source                   1..5
                         mol_type = protein
                         organism = synthetic construct
SEQUENCE: 363
SYYMH                                                              5

SEQ ID NO: 364           moltype = AA  length = 6
FEATURE                  Location/Qualifiers
source                   1..6
                         mol_type = protein
                         organism = synthetic construct
SEQUENCE: 364
TSYYMH                                                             6

SEQ ID NO: 365           moltype = AA  length = 8
FEATURE                  Location/Qualifiers
source                   1..8
                         mol_type = protein
```

-continued

SEQUENCE: 365
GYTFTSYY                                                                      8

SEQ ID NO: 366          moltype = AA   length = 6
FEATURE                 Location/Qualifiers
source                  1..6
                        mol_type = protein
                        organism = synthetic construct
SEQUENCE: 366
NPSGGS                                                                        6

SEQ ID NO: 367          moltype = AA   length = 10
FEATURE                 Location/Qualifiers
source                  1..10
                        mol_type = protein
                        organism = synthetic construct
SEQUENCE: 367
IINPSGGSTS                                                                    10

SEQ ID NO: 368          moltype = AA   length = 17
FEATURE                 Location/Qualifiers
source                  1..17
                        mol_type = protein
                        organism = synthetic construct
SEQUENCE: 368
IINPSGGSTS YAQKFQG                                                            17

SEQ ID NO: 369          moltype = AA   length = 13
FEATURE                 Location/Qualifiers
source                  1..13
                        mol_type = protein
                        organism = synthetic construct
SEQUENCE: 369
WMGIINPSGG STS                                                                13

SEQ ID NO: 370          moltype = AA   length = 8
FEATURE                 Location/Qualifiers
source                  1..8
                        mol_type = protein
                        organism = synthetic construct
SEQUENCE: 370
INPSGGST                                                                      8

SEQ ID NO: 371          moltype = AA   length = 9
FEATURE                 Location/Qualifiers
source                  1..9
                        mol_type = protein
                        organism = synthetic construct
SEQUENCE: 371
APGKFPLDY                                                                     9

SEQ ID NO: 372          moltype = AA   length = 9
FEATURE                 Location/Qualifiers
source                  1..9
                        mol_type = protein
                        organism = synthetic construct
SEQUENCE: 372
APGKFPLDY                                                                     9

SEQ ID NO: 373          moltype = AA   length = 9
FEATURE                 Location/Qualifiers
source                  1..9
                        mol_type = protein
                        organism = synthetic construct
SEQUENCE: 373
APGKFPLDY                                                                     9

SEQ ID NO: 374          moltype = AA   length = 10
FEATURE                 Location/Qualifiers
source                  1..10
                        mol_type = protein
                        organism = synthetic construct
SEQUENCE: 374
ARAPGKFPLD                                                                    10

SEQ ID NO: 375          moltype = AA   length = 11
FEATURE                 Location/Qualifiers
source                  1..11

```
                        mol_type = protein
                        organism = synthetic construct
SEQUENCE: 375
ARAPGKFPLD Y                                              11

SEQ ID NO: 376          moltype = AA  length = 16
FEATURE                 Location/Qualifiers
source                  1..16
                        mol_type = protein
                        organism = synthetic construct
SEQUENCE: 376
RSSQSLLHSN GYNYLD                                         16

SEQ ID NO: 377          moltype = AA  length = 16
FEATURE                 Location/Qualifiers
source                  1..16
                        mol_type = protein
                        organism = synthetic construct
SEQUENCE: 377
RSSQSLLHSN GYNYLD                                         16

SEQ ID NO: 378          moltype = AA  length = 16
FEATURE                 Location/Qualifiers
source                  1..16
                        mol_type = protein
                        organism = synthetic construct
SEQUENCE: 378
RSSQSLLHSN GYNYLD                                         16

SEQ ID NO: 379          moltype = AA  length = 12
FEATURE                 Location/Qualifiers
source                  1..12
                        mol_type = protein
                        organism = synthetic construct
SEQUENCE: 379
LHSNGYNYLD WY                                             12

SEQ ID NO: 380          moltype = AA  length = 11
FEATURE                 Location/Qualifiers
source                  1..11
                        mol_type = protein
                        organism = synthetic construct
SEQUENCE: 380
QSLLHSNGYN Y                                              11

SEQ ID NO: 381          moltype = AA  length = 7
FEATURE                 Location/Qualifiers
source                  1..7
                        mol_type = protein
                        organism = synthetic construct
SEQUENCE: 381
LGSNRAS                                                   7

SEQ ID NO: 382          moltype = AA  length = 7
FEATURE                 Location/Qualifiers
source                  1..7
                        mol_type = protein
                        organism = synthetic construct
SEQUENCE: 382
LGSNRAS                                                   7

SEQ ID NO: 383          moltype = AA  length = 7
FEATURE                 Location/Qualifiers
source                  1..7
                        mol_type = protein
                        organism = synthetic construct
SEQUENCE: 383
LGSNRAS                                                   7

SEQ ID NO: 384          moltype = AA  length = 10
FEATURE                 Location/Qualifiers
source                  1..10
                        mol_type = protein
                        organism = synthetic construct
SEQUENCE: 384
LLIYLGSNRA                                                10

SEQ ID NO: 385          moltype =    length =
SEQUENCE: 385
```

-continued

```
000

SEQ ID NO: 386          moltype = AA  length = 9
FEATURE                 Location/Qualifiers
source                  1..9
                        mol_type = protein
                        organism = synthetic construct SEQUENCE: 386
MQALQTPWT                                                                  9

SEQ ID NO: 387          moltype = AA  length = 9
FEATURE                 Location/Qualifiers
source                  1..9
                        mol_type = protein
                        organism = synthetic construct SEQUENCE: 387
MQALQTPWT                                                                  9

SEQ ID NO: 388          moltype = AA  length = 9
FEATURE                 Location/Qualifiers
source                  1..9
                        mol_type = protein
                        organism = synthetic construct SEQUENCE: 388
MQALQTPWT                                                                  9

SEQ ID NO: 389          moltype = AA  length = 8
FEATURE                 Location/Qualifiers
source                  1..8
                        mol_type = protein
                        organism = synthetic construct SEQUENCE: 389
MQALQTPW                                                                   8

SEQ ID NO: 390          moltype = AA  length = 9
FEATURE                 Location/Qualifiers
source                  1..9
                        mol_type = protein
                        organism = synthetic construct SEQUENCE: 390
MQALQTPWT                                                                  9

SEQ ID NO: 391          moltype = AA  length = 7
FEATURE                 Location/Qualifiers
source                  1..7
                        mol_type = protein
                        organism = synthetic construct SEQUENCE: 391
GYSFTSY                                                                    7

SEQ ID NO: 392          moltype = AA  length = 10
FEATURE                 Location/Qualifiers
source                  1..10
                        mol_type = protein
                        organism = synthetic construct SEQUENCE: 392
GYSFTSYWIG                                                                 10

SEQ ID NO: 393          moltype = AA  length = 5
FEATURE                 Location/Qualifiers
source                  1..5
                        mol_type = protein
                        organism = synthetic construct SEQUENCE: 393
SYWIG                                                                      5

SEQ ID NO: 394          moltype = AA  length = 6
FEATURE                 Location/Qualifiers
source                  1..6
                        mol_type = protein
                        organism = synthetic construct SEQUENCE: 394
TSYWIG                                                                     6

SEQ ID NO: 395          moltype = AA  length = 8
FEATURE                 Location/Qualifiers
source                  1..8
                        mol_type = protein
                        organism = synthetic construct
```

```
SEQUENCE: 395
GYSFTSYW                                                              8

SEQ ID NO: 396         moltype = AA   length = 6
FEATURE                Location/Qualifiers
source                 1..6
                       mol_type = protein
                       organism = synthetic construct
SEQUENCE: 396
YPGDSD                                                                6

SEQ ID NO: 397         moltype = AA   length = 10
FEATURE                Location/Qualifiers
source                 1..10
                       mol_type = protein
                       organism = synthetic construct
SEQUENCE: 397
IIYPGDSDTR                                                           10

SEQ ID NO: 398         moltype = AA   length = 17
FEATURE                Location/Qualifiers
source                 1..17
                       mol_type = protein
                       organism = synthetic construct
SEQUENCE: 398
IIYPGDSDTR YSPSFQG                                                   17

SEQ ID NO: 399         moltype = AA   length = 13
FEATURE                Location/Qualifiers
source                 1..13
                       mol_type = protein
                       organism = synthetic construct
SEQUENCE: 399
WMGIIYPGDS DTR                                                       13

SEQ ID NO: 400         moltype = AA   length = 8
FEATURE                Location/Qualifiers
source                 1..8
                       mol_type = protein
                       organism = synthetic construct
SEQUENCE: 400
IYPGDSDT                                                              8

SEQ ID NO: 401         moltype = AA   length = 13
FEATURE                Location/Qualifiers
source                 1..13
                       mol_type = protein
                       organism = synthetic construct
SEQUENCE: 401
AIVGATSGYW FDP                                                       13

SEQ ID NO: 402         moltype = AA   length = 13
FEATURE                Location/Qualifiers
source                 1..13
                       mol_type = protein
                       organism = synthetic construct
SEQUENCE: 402
AIVGATSGYW FDP                                                       13

SEQ ID NO: 403         moltype = AA   length = 13
FEATURE                Location/Qualifiers
source                 1..13
                       mol_type = protein
                       organism = synthetic construct
SEQUENCE: 403
AIVGATSGYW FDP                                                       13

SEQ ID NO: 404         moltype = AA   length = 14
FEATURE                Location/Qualifiers
source                 1..14
                       mol_type = protein
                       organism = synthetic construct
SEQUENCE: 404
ARAIVGATSG YWFD                                                      14

SEQ ID NO: 405         moltype = AA   length = 15
FEATURE                Location/Qualifiers
source                 1..15
                       mol_type = protein
```

-continued

```
                      organism = synthetic construct
SEQUENCE: 405
ARAIVGATSG YWFDP                                                 15

SEQ ID NO: 406        moltype = AA  length = 16
FEATURE               Location/Qualifiers
source                1..16
                      mol_type = protein
                      organism = synthetic construct
SEQUENCE: 406
RSSQSLLHSN GYNYLD                                                16

SEQ ID NO: 407        moltype = AA  length = 16
FEATURE               Location/Qualifiers
source                1..16
                      mol_type = protein
                      organism = synthetic construct
SEQUENCE: 407
RSSQSLLHSN GYNYLD                                                16

SEQ ID NO: 408        moltype = AA  length = 16
FEATURE               Location/Qualifiers
source                1..16
                      mol_type = protein
                      organism = synthetic construct
SEQUENCE: 408
RSSQSLLHSN GYNYLD                                                16

SEQ ID NO: 409        moltype = AA  length = 12
FEATURE               Location/Qualifiers
source                1..12
                      mol_type = protein
                      organism = synthetic construct
SEQUENCE: 409
LHSNGYNYLD WY                                                    12

SEQ ID NO: 410        moltype = AA  length = 11
FEATURE               Location/Qualifiers
source                1..11
                      mol_type = protein
                      organism = synthetic construct
SEQUENCE: 410
QSLLHSNGYN Y                                                     11

SEQ ID NO: 411        moltype = AA  length = 7
FEATURE               Location/Qualifiers
source                1..7
                      mol_type = protein
                      organism = synthetic construct
SEQUENCE: 411
LGSNRAS                                                          7

SEQ ID NO: 412        moltype = AA  length = 7
FEATURE               Location/Qualifiers
source                1..7
                      mol_type = protein
                      organism = synthetic construct
SEQUENCE: 412
LGSNRAS                                                          7

SEQ ID NO: 413        moltype = AA  length = 7
FEATURE               Location/Qualifiers
source                1..7
                      mol_type = protein
                      organism = synthetic construct
SEQUENCE: 413
LGSNRAS                                                          7

SEQ ID NO: 414        moltype = AA  length = 10
FEATURE               Location/Qualifiers
source                1..10
                      mol_type = protein
                      organism = synthetic construct
SEQUENCE: 414
LLIYLGSNRA                                                       10

SEQ ID NO: 415        moltype =   length =
SEQUENCE: 415
000
```

-continued

```
SEQ ID NO: 416           moltype = AA   length = 9
FEATURE                  Location/Qualifiers
source                   1..9
                         mol_type = protein
                         organism = synthetic construct
SEQUENCE: 416
MQALQTPLT                                                              9

SEQ ID NO: 417           moltype = AA   length = 9
FEATURE                  Location/Qualifiers
source                   1..9
                         mol_type = protein
                         organism = synthetic construct
SEQUENCE: 417
MQALQTPLT                                                              9

SEQ ID NO: 418           moltype = AA   length = 9
FEATURE                  Location/Qualifiers
source                   1..9
                         mol_type = protein
                         organism = synthetic construct
SEQUENCE: 418
MQALQTPLT                                                              9

SEQ ID NO: 419           moltype = AA   length = 8
FEATURE                  Location/Qualifiers
source                   1..8
                         mol_type = protein
                         organism = synthetic construct
SEQUENCE: 419
MQALQTPL                                                               8

SEQ ID NO: 420           moltype = AA   length = 9
FEATURE                  Location/Qualifiers
source                   1..9
                         mol_type = protein
                         organism = synthetic construct
SEQUENCE: 420
MQALQTPLT                                                              9

SEQ ID NO: 421           moltype = AA   length = 7
FEATURE                  Location/Qualifiers
source                   1..7
                         mol_type = protein
                         organism = synthetic construct
SEQUENCE: 421
GFTFSSY                                                                7

SEQ ID NO: 422           moltype = AA   length = 10
FEATURE                  Location/Qualifiers
source                   1..10
                         mol_type = protein
                         organism = synthetic construct
SEQUENCE: 422
GFTFSSYAMH                                                             10

SEQ ID NO: 423           moltype = AA   length = 5
FEATURE                  Location/Qualifiers
source                   1..5
                         mol_type = protein
                         organism = synthetic construct
SEQUENCE: 423
SYAMH                                                                  5

SEQ ID NO: 424           moltype = AA   length = 6
FEATURE                  Location/Qualifiers
source                   1..6
                         mol_type = protein
                         organism = synthetic construct
SEQUENCE: 424
SSYAMH                                                                 6

SEQ ID NO: 425           moltype = AA   length = 8
FEATURE                  Location/Qualifiers
source                   1..8
                         mol_type = protein
                         organism = synthetic construct
SEQUENCE: 425
```

-continued

```
GFTFSSYA                                                              8

SEQ ID NO: 426          moltype = AA   length = 6
FEATURE                 Location/Qualifiers
source                  1..6
                        mol_type = protein
                        organism = synthetic construct SEQUENCE: 426
SYDGSN                                                                6

SEQ ID NO: 427          moltype = AA   length = 10
FEATURE                 Location/Qualifiers
source                  1..10
                        mol_type = protein
                        organism = synthetic construct SEQUENCE: 427
VISYDGSNKY                                                            10

SEQ ID NO: 428          moltype = AA   length = 17
FEATURE                 Location/Qualifiers
source                  1..17
                        mol_type = protein
                        organism = synthetic construct SEQUENCE: 428
VISYDGSNKY YADSVKG                                                    17

SEQ ID NO: 429          moltype = AA   length = 13
FEATURE                 Location/Qualifiers
source                  1..13
                        mol_type = protein
                        organism = synthetic construct SEQUENCE: 429
WVAVISYDGS NKY                                                        13

SEQ ID NO: 430          moltype = AA   length = 8
FEATURE                 Location/Qualifiers
source                  1..8
                        mol_type = protein
                        organism = synthetic construct SEQUENCE: 430
ISYDGSNK                                                              8

SEQ ID NO: 431          moltype = AA   length = 12
FEATURE                 Location/Qualifiers
source                  1..12
                        mol_type = protein
                        organism = synthetic construct SEQUENCE: 431
PVLRYFDWLP NY                                                         12

SEQ ID NO: 432          moltype = AA   length = 12
FEATURE                 Location/Qualifiers
source                  1..12
                        mol_type = protein
                        organism = synthetic construct SEQUENCE: 432
PVLRYFDWLP NY                                                         12

SEQ ID NO: 433          moltype = AA   length = 12
FEATURE                 Location/Qualifiers
source                  1..12
                        mol_type = protein
                        organism = synthetic construct SEQUENCE: 433
PVLRYFDWLP NY                                                         12

SEQ ID NO: 434          moltype = AA   length = 13
FEATURE                 Location/Qualifiers
source                  1..13
                        mol_type = protein
                        organism = synthetic construct SEQUENCE: 434
ASPVLRYFDW LPN                                                        13

SEQ ID NO: 435          moltype = AA   length = 14
FEATURE                 Location/Qualifiers
source                  1..14
                        mol_type = protein
                        organism = synthetic construct
```

-continued

```
SEQUENCE: 435
ASPVLRYFDW LPNY                                                        14

SEQ ID NO: 436        moltype = AA   length = 16
FEATURE               Location/Qualifiers
source                1..16
                      mol_type = protein
                      organism = synthetic construct
SEQUENCE: 436
RSSQSLVYSD GNTYLN                                                      16

SEQ ID NO: 437        moltype = AA   length = 16
FEATURE               Location/Qualifiers
source                1..16
                      mol_type = protein
                      organism = synthetic construct
SEQUENCE: 437
RSSQSLVYSD GNTYLN                                                      16

SEQ ID NO: 438        moltype = AA   length = 16
FEATURE               Location/Qualifiers
source                1..16
                      mol_type = protein
                      organism = synthetic construct
SEQUENCE: 438
RSSQSLVYSD GNTYLN                                                      16

SEQ ID NO: 439        moltype = AA   length = 12
FEATURE               Location/Qualifiers
source                1..12
                      mol_type = protein
                      organism = synthetic construct
SEQUENCE: 439
VYSDGNTYLN WF                                                          12

SEQ ID NO: 440        moltype = AA   length = 11
FEATURE               Location/Qualifiers
source                1..11
                      mol_type = protein
                      organism = synthetic construct
SEQUENCE: 440
QSLVYSDGNT Y                                                           11

SEQ ID NO: 441        moltype = AA   length = 7
FEATURE               Location/Qualifiers
source                1..7
                      mol_type = protein
                      organism = synthetic construct
SEQUENCE: 441
KVSNRDS                                                                7

SEQ ID NO: 442        moltype = AA   length = 7
FEATURE               Location/Qualifiers
source                1..7
                      mol_type = protein
                      organism = synthetic construct
SEQUENCE: 442
KVSNRDS                                                                7

SEQ ID NO: 443        moltype = AA   length = 7
FEATURE               Location/Qualifiers
source                1..7
                      mol_type = protein
                      organism = synthetic construct
SEQUENCE: 443
KVSNRDS                                                                7

SEQ ID NO: 444        moltype = AA   length = 10
FEATURE               Location/Qualifiers
source                1..10
                      mol_type = protein
                      organism = synthetic construct
SEQUENCE: 444
RLIYKVSNRD                                                             10

SEQ ID NO: 445        moltype =   length =
SEQUENCE: 445
000
```

-continued

```
SEQ ID NO: 446          moltype = AA   length = 9
FEATURE                 Location/Qualifiers
source                  1..9
                        mol_type = protein
                        organism = synthetic construct
SEQUENCE: 446
MQGTHWPYS                                                          9

SEQ ID NO: 447          moltype = AA   length = 9
FEATURE                 Location/Qualifiers
source                  1..9
                        mol_type = protein
                        organism = synthetic construct
SEQUENCE: 447
MQGTHWPYS                                                          9

SEQ ID NO: 448          moltype = AA   length = 9
FEATURE                 Location/Qualifiers
source                  1..9
                        mol_type = protein
                        organism = synthetic construct
SEQUENCE: 448
MQGTHWPYS                                                          9

SEQ ID NO: 449          moltype = AA   length = 8
FEATURE                 Location/Qualifiers
source                  1..8
                        mol_type = protein
                        organism = synthetic construct
SEQUENCE: 449
MQGTHWPY                                                           8

SEQ ID NO: 450          moltype = AA   length = 9
FEATURE                 Location/Qualifiers
source                  1..9
                        mol_type = protein
                        organism = synthetic construct
SEQUENCE: 450
MQGTHWPYS                                                          9

SEQ ID NO: 451          moltype = AA   length = 7
FEATURE                 Location/Qualifiers
source                  1..7
                        mol_type = protein
                        organism = synthetic construct
SEQUENCE: 451
GYSFTSY                                                            7

SEQ ID NO: 452          moltype = AA   length = 10
FEATURE                 Location/Qualifiers
source                  1..10
                        mol_type = protein
                        organism = synthetic construct
SEQUENCE: 452
GYSFTSYWIG                                                         10

SEQ ID NO: 453          moltype = AA   length = 5
FEATURE                 Location/Qualifiers
source                  1..5
                        mol_type = protein
                        organism = synthetic construct
SEQUENCE: 453
SYWIG                                                              5

SEQ ID NO: 454          moltype = AA   length = 6
FEATURE                 Location/Qualifiers
source                  1..6
                        mol_type = protein
                        organism = synthetic construct
SEQUENCE: 454
TSYWIG                                                             6

SEQ ID NO: 455          moltype = AA   length = 8
FEATURE                 Location/Qualifiers
source                  1..8
                        mol_type = protein
                        organism = synthetic construct
SEQUENCE: 455
GYSFTSYW                                                           8
```

```
SEQ ID NO: 456            moltype = AA   length = 6
FEATURE                   Location/Qualifiers
source                    1..6
                          mol_type = protein
                          organism = synthetic construct
SEQUENCE: 456
YPGDSD                                                            6

SEQ ID NO: 457            moltype = AA   length = 10
FEATURE                   Location/Qualifiers
source                    1..10
                          mol_type = protein
                          organism = synthetic construct
SEQUENCE: 457
IIYPGDSDTR                                                        10

SEQ ID NO: 458            moltype = AA   length = 17
FEATURE                   Location/Qualifiers
source                    1..17
                          mol_type = protein
                          organism = synthetic construct
SEQUENCE: 458
IIYPGDSDTR YSPSFQG                                                17

SEQ ID NO: 459            moltype = AA   length = 13
FEATURE                   Location/Qualifiers
source                    1..13
                          mol_type = protein
                          organism = synthetic construct
SEQUENCE: 459
WMGIIYPGDS DTR                                                    13

SEQ ID NO: 460            moltype = AA   length = 8
FEATURE                   Location/Qualifiers
source                    1..8
                          mol_type = protein
                          organism = synthetic construct
SEQUENCE: 460
IYPGDSDT                                                          8

SEQ ID NO: 461            moltype = AA   length = 9
FEATURE                   Location/Qualifiers
source                    1..9
                          mol_type = protein
                          organism = synthetic construct
SEQUENCE: 461
GHGATAFDI                                                         9

SEQ ID NO: 462            moltype = AA   length = 9
FEATURE                   Location/Qualifiers
source                    1..9
                          mol_type = protein
                          organism = synthetic construct
SEQUENCE: 462
GHGATAFDI                                                         9

SEQ ID NO: 463            moltype = AA   length = 9
FEATURE                   Location/Qualifiers
source                    1..9
                          mol_type = protein
                          organism = synthetic construct
SEQUENCE: 463
GHGATAFDI                                                         9

SEQ ID NO: 464            moltype = AA   length = 10
FEATURE                   Location/Qualifiers
source                    1..10
                          mol_type = protein
                          organism = synthetic construct
SEQUENCE: 464
ARGHGATAFD                                                        10

SEQ ID NO: 465            moltype = AA   length = 11
FEATURE                   Location/Qualifiers
source                    1..11
                          mol_type = protein
                          organism = synthetic construct
SEQUENCE: 465
```

-continued

```
ARGHGATAFD I                                                           11

SEQ ID NO: 466          moltype = AA  length = 16
FEATURE                 Location/Qualifiers
source                  1..16
                        mol_type = protein
                        organism = synthetic construct
SEQUENCE: 466
RSSQSLLHSN GYNYLD                                                      16

SEQ ID NO: 467          moltype = AA  length = 16
FEATURE                 Location/Qualifiers
source                  1..16
                        mol_type = protein
                        organism = synthetic construct
SEQUENCE: 467
RSSQSLLHSN GYNYLD                                                      16

SEQ ID NO: 468          moltype = AA  length = 16
FEATURE                 Location/Qualifiers
source                  1..16
                        mol_type = protein
                        organism = synthetic construct
SEQUENCE: 468
RSSQSLLHSN GYNYLD                                                      16

SEQ ID NO: 469          moltype = AA  length = 12
FEATURE                 Location/Qualifiers
source                  1..12
                        mol_type = protein
                        organism = synthetic construct
SEQUENCE: 469
LHSNGYNYLD WY                                                          12

SEQ ID NO: 470          moltype = AA  length = 11
FEATURE                 Location/Qualifiers
source                  1..11
                        mol_type = protein
                        organism = synthetic construct
SEQUENCE: 470
QSLLHSNGYN Y                                                           11

SEQ ID NO: 471          moltype = AA  length = 7
FEATURE                 Location/Qualifiers
source                  1..7
                        mol_type = protein
                        organism = synthetic construct
SEQUENCE: 471
LGSNRAS                                                                7

SEQ ID NO: 472          moltype = AA  length = 7
FEATURE                 Location/Qualifiers
source                  1..7
                        mol_type = protein
                        organism = synthetic construct
SEQUENCE: 472
LGSNRAS                                                                7

SEQ ID NO: 473          moltype = AA  length = 7
FEATURE                 Location/Qualifiers
source                  1..7
                        mol_type = protein
                        organism = synthetic construct
SEQUENCE: 473
LGSNRAS                                                                7

SEQ ID NO: 474          moltype = AA  length = 10
FEATURE                 Location/Qualifiers
source                  1..10
                        mol_type = protein
                        organism = synthetic construct
SEQUENCE: 474
LLIYLGSNRA                                                             10

SEQ ID NO: 475          moltype =    length =
SEQUENCE: 475
000

SEQ ID NO: 476          moltype = AA  length = 9
```

-continued

```
FEATURE              Location/Qualifiers
source               1..9
                     mol_type = protein
                     organism = synthetic construct
SEQUENCE: 476
MQALQTPPT                                                            9

SEQ ID NO: 477       moltype = AA  length = 9
FEATURE              Location/Qualifiers
source               1..9
                     mol_type = protein
                     organism = synthetic construct
SEQUENCE: 477
MQALQTPPT                                                            9

SEQ ID NO: 478       moltype = AA  length = 9
FEATURE              Location/Qualifiers
source               1..9
                     mol_type = protein
                     organism = synthetic construct
SEQUENCE: 478
MQALQTPPT                                                            9

SEQ ID NO: 479       moltype = AA  length = 8
FEATURE              Location/Qualifiers
source               1..8
                     mol_type = protein
                     organism = synthetic construct
SEQUENCE: 479
MQALQTPP                                                             8

SEQ ID NO: 480       moltype = AA  length = 9
FEATURE              Location/Qualifiers
source               1..9
                     mol_type = protein
                     organism = synthetic construct
SEQUENCE: 480
MQALQTPPT                                                            9

SEQ ID NO: 481       moltype = AA  length = 7
FEATURE              Location/Qualifiers
source               1..7
                     mol_type = protein
                     organism = synthetic construct
SEQUENCE: 481
GGTFSSY                                                              7

SEQ ID NO: 482       moltype = AA  length = 10
FEATURE              Location/Qualifiers
source               1..10
                     mol_type = protein
                     organism = synthetic construct
SEQUENCE: 482
GGTFSSYAIS                                                           10

SEQ ID NO: 483       moltype = AA  length = 5
FEATURE              Location/Qualifiers
source               1..5
                     mol_type = protein
                     organism = synthetic construct
SEQUENCE: 483
SYAIS                                                                5

SEQ ID NO: 484       moltype = AA  length = 6
FEATURE              Location/Qualifiers
source               1..6
                     mol_type = protein
                     organism = synthetic construct
SEQUENCE: 484
SSYAIS                                                               6

SEQ ID NO: 485       moltype = AA  length = 8
FEATURE              Location/Qualifiers
source               1..8
                     mol_type = protein
                     organism = synthetic construct
SEQUENCE: 485
GGTFSSYA                                                             8
```

-continued

```
SEQ ID NO: 486           moltype = AA   length = 6
FEATURE                  Location/Qualifiers
source                   1..6
                         mol_type = protein
                         organism = synthetic construct
SEQUENCE: 486
IPIFGT                                                             6

SEQ ID NO: 487           moltype = AA   length = 10
FEATURE                  Location/Qualifiers
source                   1..10
                         mol_type = protein
                         organism = synthetic construct
SEQUENCE: 487
GIIPIFGTAN                                                        10

SEQ ID NO: 488           moltype = AA   length = 17
FEATURE                  Location/Qualifiers
source                   1..17
                         mol_type = protein
                         organism = synthetic construct
SEQUENCE: 488
GIIPIFGTAN YAQKFQG                                                17

SEQ ID NO: 489           moltype = AA   length = 13
FEATURE                  Location/Qualifiers
source                   1..13
                         mol_type = protein
                         organism = synthetic construct
SEQUENCE: 489
WMGGIIPIFG TAN                                                    13

SEQ ID NO: 490           moltype = AA   length = 8
FEATURE                  Location/Qualifiers
source                   1..8
                         mol_type = protein
                         organism = synthetic construct
SEQUENCE: 490
IIPIFGTA                                                           8

SEQ ID NO: 491           moltype = AA   length = 14
FEATURE                  Location/Qualifiers
source                   1..14
                         mol_type = protein
                         organism = synthetic construct
SEQUENCE: 491
DRYYDSSGYY LMDP                                                   14

SEQ ID NO: 492           moltype = AA   length = 14
FEATURE                  Location/Qualifiers
source                   1..14
                         mol_type = protein
                         organism = synthetic construct
SEQUENCE: 492
DRYYDSSGYY LMDP                                                   14

SEQ ID NO: 493           moltype = AA   length = 14
FEATURE                  Location/Qualifiers
source                   1..14
                         mol_type = protein
                         organism = synthetic construct
SEQUENCE: 493
DRYYDSSGYY LMDP                                                   14

SEQ ID NO: 494           moltype = AA   length = 15
FEATURE                  Location/Qualifiers
source                   1..15
                         mol_type = protein
                         organism = synthetic construct
SEQUENCE: 494
ARDRYYDSSG YYLMD                                                  15

SEQ ID NO: 495           moltype = AA   length = 16
FEATURE                  Location/Qualifiers
source                   1..16
                         mol_type = protein
                         organism = synthetic construct
SEQUENCE: 495
ARDRYYDSSG YYLMDP                                                 16
```

-continued

```
SEQ ID NO: 496          moltype = AA   length = 16
FEATURE                 Location/Qualifiers
source                  1..16
                        mol_type = protein
                        organism = synthetic construct
SEQUENCE: 496
RSSQSLVHSD GNTYLS                                                      16

SEQ ID NO: 497          moltype = AA   length = 16
FEATURE                 Location/Qualifiers
source                  1..16
                        mol_type = protein
                        organism = synthetic construct
SEQUENCE: 497
RSSQSLVHSD GNTYLS                                                      16

SEQ ID NO: 498          moltype = AA   length = 16
FEATURE                 Location/Qualifiers
source                  1..16
                        mol_type = protein
                        organism = synthetic construct
SEQUENCE: 498
RSSQSLVHSD GNTYLS                                                      16

SEQ ID NO: 499          moltype = AA   length = 12
FEATURE                 Location/Qualifiers
source                  1..12
                        mol_type = protein
                        organism = synthetic construct
SEQUENCE: 499
VHSDGNTYLS WL                                                          12

SEQ ID NO: 500          moltype = AA   length = 11
FEATURE                 Location/Qualifiers
source                  1..11
                        mol_type = protein
                        organism = synthetic construct
SEQUENCE: 500
QSLVHSDGNT Y                                                           11

SEQ ID NO: 501          moltype = AA   length = 7
FEATURE                 Location/Qualifiers
source                  1..7
                        mol_type = protein
                        organism = synthetic construct
SEQUENCE: 501
KISNRFS                                                                7

SEQ ID NO: 502          moltype = AA   length = 7
FEATURE                 Location/Qualifiers
source                  1..7
                        mol_type = protein
                        organism = synthetic construct
SEQUENCE: 502
KISNRFS                                                                7

SEQ ID NO: 503          moltype = AA   length = 7
FEATURE                 Location/Qualifiers
source                  1..7
                        mol_type = protein
                        organism = synthetic construct
SEQUENCE: 503
KISNRFS                                                                7

SEQ ID NO: 504          moltype = AA   length = 10
FEATURE                 Location/Qualifiers
source                  1..10
                        mol_type = protein
                        organism = synthetic construct
SEQUENCE: 504
LLIYKISNRF                                                             10

SEQ ID NO: 505          moltype =    length =
SEQUENCE: 505
000

SEQ ID NO: 506          moltype = AA   length = 9
FEATURE                 Location/Qualifiers
```

-continued

```
source                  1..9
                        mol_type = protein
                        organism = synthetic construct
SEQUENCE: 506
MQATQFPLT                                                                9

SEQ ID NO: 507          moltype = AA   length = 9
FEATURE                 Location/Qualifiers
source                  1..9
                        mol_type = protein
                        organism = synthetic construct
SEQUENCE: 507
MQATQFPLT                                                                9

SEQ ID NO: 508          moltype = AA   length = 9
FEATURE                 Location/Qualifiers
source                  1..9
                        mol_type = protein
                        organism = synthetic construct
SEQUENCE: 508
MQATQFPLT                                                                9

SEQ ID NO: 509          moltype = AA   length = 8
FEATURE                 Location/Qualifiers
source                  1..8
                        mol_type = protein
                        organism = synthetic construct
SEQUENCE: 509
MQATQFPL                                                                 8

SEQ ID NO: 510          moltype = AA   length = 9
FEATURE                 Location/Qualifiers
source                  1..9
                        mol_type = protein
                        organism = synthetic construct
SEQUENCE: 510
MQATQFPLT                                                                9

SEQ ID NO: 511          moltype = AA   length = 7
FEATURE                 Location/Qualifiers
source                  1..7
                        mol_type = protein
                        organism = synthetic construct
SEQUENCE: 511
GYTFTSY                                                                  7

SEQ ID NO: 512          moltype = AA   length = 10
FEATURE                 Location/Qualifiers
source                  1..10
                        mol_type = protein
                        organism = synthetic construct
SEQUENCE: 512
GYTFTSYYMH                                                               10

SEQ ID NO: 513          moltype = AA   length = 5
FEATURE                 Location/Qualifiers
source                  1..5
                        mol_type = protein
                        organism = synthetic construct
SEQUENCE: 513
SYYMH                                                                    5

SEQ ID NO: 514          moltype = AA   length = 6
FEATURE                 Location/Qualifiers
source                  1..6
                        mol_type = protein
                        organism = synthetic construct
SEQUENCE: 514
TSYYMH                                                                   6

SEQ ID NO: 515          moltype = AA   length = 8
FEATURE                 Location/Qualifiers
source                  1..8
                        mol_type = protein
                        organism = synthetic construct
SEQUENCE: 515
GYTFTSYY                                                                 8

SEQ ID NO: 516          moltype = AA   length = 6
```

-continued

```
FEATURE              Location/Qualifiers
source               1..6
                     mol_type = protein
                     organism = synthetic construct
SEQUENCE: 516
NPSGGS                                                               6

SEQ ID NO: 517       moltype = AA  length = 10
FEATURE              Location/Qualifiers
source               1..10
                     mol_type = protein
                     organism = synthetic construct
SEQUENCE: 517
IINPSGGSTS                                                           10

SEQ ID NO: 518       moltype = AA  length = 17
FEATURE              Location/Qualifiers
source               1..17
                     mol_type = protein
                     organism = synthetic construct
SEQUENCE: 518
IINPSGGSTS YAQKFQG                                                   17

SEQ ID NO: 519       moltype = AA  length = 13
FEATURE              Location/Qualifiers
source               1..13
                     mol_type = protein
                     organism = synthetic construct
SEQUENCE: 519
WMGIINPSGG STS                                                       13

SEQ ID NO: 520       moltype = AA  length = 8
FEATURE              Location/Qualifiers
source               1..8
                     mol_type = protein
                     organism = synthetic construct
SEQUENCE: 520
INPSGGST                                                             8

SEQ ID NO: 521       moltype = AA  length = 9
FEATURE              Location/Qualifiers
source               1..9
                     mol_type = protein
                     organism = synthetic construct
SEQUENCE: 521
APGKFPLDY                                                            9

SEQ ID NO: 522       moltype = AA  length = 9
FEATURE              Location/Qualifiers
source               1..9
                     mol_type = protein
                     organism = synthetic construct
SEQUENCE: 522
APGKFPLDY                                                            9

SEQ ID NO: 523       moltype = AA  length = 9
FEATURE              Location/Qualifiers
source               1..9
                     mol_type = protein
                     organism = synthetic construct
SEQUENCE: 523
APGKFPLDY                                                            9

SEQ ID NO: 524       moltype = AA  length = 10
FEATURE              Location/Qualifiers
source               1..10
                     mol_type = protein
                     organism = synthetic construct
SEQUENCE: 524
ARAPGKFPLD                                                           10

SEQ ID NO: 525       moltype = AA  length = 11
FEATURE              Location/Qualifiers
source               1..11
                     mol_type = protein
                     organism = synthetic construct
SEQUENCE: 525
ARAPGKFPLD Y                                                         11
```

-continued

```
SEQ ID NO: 526              moltype = AA   length = 16
FEATURE                     Location/Qualifiers
source                      1..16
                            mol_type = protein
                            organism = synthetic construct
SEQUENCE: 526
RSSQSLLKSN GYNYLD                                               16

SEQ ID NO: 527              moltype = AA   length = 16
FEATURE                     Location/Qualifiers
source                      1..16
                            mol_type = protein
                            organism = synthetic construct
SEQUENCE: 527
RSSQSLLKSN GYNYLD                                               16

SEQ ID NO: 528              moltype = AA   length = 16
FEATURE                     Location/Qualifiers
source                      1..16
                            mol_type = protein
                            organism = synthetic construct
SEQUENCE: 528
RSSQSLLKSN GYNYLD                                               16

SEQ ID NO: 529              moltype = AA   length = 12
FEATURE                     Location/Qualifiers
source                      1..12
                            mol_type = protein
                            organism = synthetic construct
SEQUENCE: 529
LKSNGYNYLD WY                                                   12

SEQ ID NO: 530              moltype = AA   length = 11
FEATURE                     Location/Qualifiers
source                      1..11
                            mol_type = protein
                            organism = synthetic construct
SEQUENCE: 530
QSLLKSNGYN Y                                                    11

SEQ ID NO: 531              moltype = AA   length = 7
FEATURE                     Location/Qualifiers
source                      1..7
                            mol_type = protein
                            organism = synthetic construct
SEQUENCE: 531
LGSNRAS                                                         7

SEQ ID NO: 532              moltype = AA   length = 7
FEATURE                     Location/Qualifiers
source                      1..7
                            mol_type = protein
                            organism = synthetic construct
SEQUENCE: 532
LGSNRAS                                                         7

SEQ ID NO: 533              moltype = AA   length = 7
FEATURE                     Location/Qualifiers
source                      1..7
                            mol_type = protein
                            organism = synthetic construct
SEQUENCE: 533
LGSNRAS                                                         7

SEQ ID NO: 534              moltype = AA   length = 10
FEATURE                     Location/Qualifiers
source                      1..10
                            mol_type = protein
                            organism = synthetic construct
SEQUENCE: 534
LLIYLGSNRA                                                      10

SEQ ID NO: 535              moltype =    length =
SEQUENCE: 535
000

SEQ ID NO: 536              moltype = AA   length = 9
FEATURE                     Location/Qualifiers
source                      1..9
```

-continued

```
                          mol_type = protein
                          organism = synthetic construct
SEQUENCE: 536
MQTLQTPYT                                                              9

SEQ ID NO: 537            moltype = AA  length = 9
FEATURE                   Location/Qualifiers
source                    1..9
                          mol_type = protein
                          organism = synthetic construct
SEQUENCE: 537
MQTLQTPYT                                                              9

SEQ ID NO: 538            moltype = AA  length = 9
FEATURE                   Location/Qualifiers
source                    1..9
                          mol_type = protein
                          organism = synthetic construct
SEQUENCE: 538
MQTLQTPYT                                                              9

SEQ ID NO: 539            moltype = AA  length = 8
FEATURE                   Location/Qualifiers
source                    1..8
                          mol_type = protein
                          organism = synthetic construct
SEQUENCE: 539
MQTLQTPY                                                               8

SEQ ID NO: 540            moltype = AA  length = 9
FEATURE                   Location/Qualifiers
source                    1..9
                          mol_type = protein
                          organism = synthetic construct
SEQUENCE: 540
MQTLQTPYT                                                              9

SEQ ID NO: 541            moltype = AA  length = 9
FEATURE                   Location/Qualifiers
source                    1..9
                          mol_type = protein
                          organism = synthetic construct
SEQUENCE: 541
GGSISSGGY                                                              9

SEQ ID NO: 542            moltype = AA  length = 12
FEATURE                   Location/Qualifiers
source                    1..12
                          mol_type = protein
                          organism = synthetic construct
SEQUENCE: 542
GGSISSGGYY WS                                                          12

SEQ ID NO: 543            moltype = AA  length = 7
FEATURE                   Location/Qualifiers
source                    1..7
                          mol_type = protein
                          organism = synthetic construct
SEQUENCE: 543
SGGYYWS                                                                7

SEQ ID NO: 544            moltype = AA  length = 8
FEATURE                   Location/Qualifiers
source                    1..8
                          mol_type = protein
                          organism = synthetic construct
SEQUENCE: 544
SSGGYYWS                                                               8

SEQ ID NO: 545            moltype = AA  length = 10
FEATURE                   Location/Qualifiers
source                    1..10
                          mol_type = protein
                          organism = synthetic construct
SEQUENCE: 545
GGSISSGGYY                                                             10

SEQ ID NO: 546            moltype = AA  length = 5
FEATURE                   Location/Qualifiers
```

-continued

```
source                    1..5
                          mol_type = protein
                          organism = synthetic construct
SEQUENCE: 546
YYSGS                                                                5

SEQ ID NO: 547            moltype = AA   length = 9
FEATURE                   Location/Qualifiers
source                    1..9
                          mol_type = protein
                          organism = synthetic construct
SEQUENCE: 547
YIYYSGSTY                                                            9

SEQ ID NO: 548            moltype = AA   length = 16
FEATURE                   Location/Qualifiers
source                    1..16
                          mol_type = protein
                          organism = synthetic construct
SEQUENCE: 548
YIYYSGSTYY NPSLKS                                                    16

SEQ ID NO: 549            moltype = AA   length = 12
FEATURE                   Location/Qualifiers
source                    1..12
                          mol_type = protein
                          organism = synthetic construct
SEQUENCE: 549
WIGYIYYSGS TY                                                        12

SEQ ID NO: 550            moltype = AA   length = 7
FEATURE                   Location/Qualifiers
source                    1..7
                          mol_type = protein
                          organism = synthetic construct
SEQUENCE: 550
IYYSGST                                                              7

SEQ ID NO: 551            moltype = AA   length = 11
FEATURE                   Location/Qualifiers
source                    1..11
                          mol_type = protein
                          organism = synthetic construct
SEQUENCE: 551
SGAAGIPWFD P                                                         11

SEQ ID NO: 552            moltype = AA   length = 11
FEATURE                   Location/Qualifiers
source                    1..11
                          mol_type = protein
                          organism = synthetic construct
SEQUENCE: 552
SGAAGIPWFD P                                                         11

SEQ ID NO: 553            moltype = AA   length = 11
FEATURE                   Location/Qualifiers
source                    1..11
                          mol_type = protein
                          organism = synthetic construct
SEQUENCE: 553
SGAAGIPWFD P                                                         11

SEQ ID NO: 554            moltype = AA   length = 12
FEATURE                   Location/Qualifiers
source                    1..12
                          mol_type = protein
                          organism = synthetic construct
SEQUENCE: 554
ARSGAAGIPW FD                                                        12

SEQ ID NO: 555            moltype = AA   length = 13
FEATURE                   Location/Qualifiers
source                    1..13
                          mol_type = protein
                          organism = synthetic construct
SEQUENCE: 555
ARSGAAGIPW FDP                                                       13

SEQ ID NO: 556            moltype = AA   length = 13
```

-continued

```
FEATURE             Location/Qualifiers
source              1..13
                    mol_type = protein
                    organism = synthetic construct
SEQUENCE: 556
SGSSSNIGNN YVS                                                      13

SEQ ID NO: 557      moltype = AA  length = 13
FEATURE             Location/Qualifiers
source              1..13
                    mol_type = protein
                    organism = synthetic construct
SEQUENCE: 557
SGSSSNIGNN YVS                                                      13

SEQ ID NO: 558      moltype = AA  length = 13
FEATURE             Location/Qualifiers
source              1..13
                    mol_type = protein
                    organism = synthetic construct
SEQUENCE: 558
SGSSSNIGNN YVS                                                      13

SEQ ID NO: 559      moltype = AA  length = 9
FEATURE             Location/Qualifiers
source              1..9
                    mol_type = protein
                    organism = synthetic construct
SEQUENCE: 559
IGNNYVSWY                                                           9

SEQ ID NO: 560      moltype = AA  length = 8
FEATURE             Location/Qualifiers
source              1..8
                    mol_type = protein
                    organism = synthetic construct
SEQUENCE: 560
SSNIGNNY                                                            8

SEQ ID NO: 561      moltype = AA  length = 7
FEATURE             Location/Qualifiers
source              1..7
                    mol_type = protein
                    organism = synthetic construct
SEQUENCE: 561
ENNERPS                                                             7

SEQ ID NO: 562      moltype = AA  length = 7
FEATURE             Location/Qualifiers
source              1..7
                    mol_type = protein
                    organism = synthetic construct
SEQUENCE: 562
ENNERPS                                                             7

SEQ ID NO: 563      moltype = AA  length = 7
FEATURE             Location/Qualifiers
source              1..7
                    mol_type = protein
                    organism = synthetic construct
SEQUENCE: 563
ENNERPS                                                             7

SEQ ID NO: 564      moltype = AA  length = 10
FEATURE             Location/Qualifiers
source              1..10
                    mol_type = protein
                    organism = synthetic construct
SEQUENCE: 564
LLIYENNERP                                                          10

SEQ ID NO: 565      moltype =   length =
SEQUENCE: 565
000

SEQ ID NO: 566      moltype = AA  length = 11
FEATURE             Location/Qualifiers
source              1..11
                    mol_type = protein
```

-continued

```
                         organism = synthetic construct
SEQUENCE: 566
GTWDSSLSAV V                                                          11

SEQ ID NO: 567           moltype = AA   length = 11
FEATURE                  Location/Qualifiers
source                   1..11
                         mol_type = protein
                         organism = synthetic construct
SEQUENCE: 567
GTWDSSLSAV V                                                          11

SEQ ID NO: 568           moltype = AA   length = 11
FEATURE                  Location/Qualifiers
source                   1..11
                         mol_type = protein
                         organism = synthetic construct
SEQUENCE: 568
GTWDSSLSAV V                                                          11

SEQ ID NO: 569           moltype = AA   length = 10
FEATURE                  Location/Qualifiers
source                   1..10
                         mol_type = protein
                         organism = synthetic construct
SEQUENCE: 569
GTWDSSLSAV                                                            10

SEQ ID NO: 570           moltype = AA   length = 11
FEATURE                  Location/Qualifiers
source                   1..11
                         mol_type = protein
                         organism = synthetic construct
SEQUENCE: 570
GTWDSSLSAV V                                                          11

SEQ ID NO: 571           moltype = AA   length = 7
FEATURE                  Location/Qualifiers
source                   1..7
                         mol_type = protein
                         organism = synthetic construct
SEQUENCE: 571
GYTFTSY                                                               7

SEQ ID NO: 572           moltype = AA   length = 10
FEATURE                  Location/Qualifiers
source                   1..10
                         mol_type = protein
                         organism = synthetic construct
SEQUENCE: 572
GYTFTSYGIS                                                            10

SEQ ID NO: 573           moltype = AA   length = 5
FEATURE                  Location/Qualifiers
source                   1..5
                         mol_type = protein
                         organism = synthetic construct
SEQUENCE: 573
SYGIS                                                                 5

SEQ ID NO: 574           moltype = AA   length = 6
FEATURE                  Location/Qualifiers
source                   1..6
                         mol_type = protein
                         organism = synthetic construct
SEQUENCE: 574
TSYGIS                                                                6

SEQ ID NO: 575           moltype = AA   length = 8
FEATURE                  Location/Qualifiers
source                   1..8
                         mol_type = protein
                         organism = synthetic construct
SEQUENCE: 575
GYTFTSYG                                                              8

SEQ ID NO: 576           moltype = AA   length = 6
FEATURE                  Location/Qualifiers
source                   1..6
```

-continued

```
                         mol_type = protein
                         organism = synthetic construct
SEQUENCE: 576
SAYNGN                                                           6

SEQ ID NO: 577           moltype = AA   length = 10
FEATURE                  Location/Qualifiers
source                   1..10
                         mol_type = protein
                         organism = synthetic construct
SEQUENCE: 577
WISAYNGNTN                                                       10

SEQ ID NO: 578           moltype = AA   length = 17
FEATURE                  Location/Qualifiers
source                   1..17
                         mol_type = protein
                         organism = synthetic construct
SEQUENCE: 578
WISAYNGNTN YAQKLQG                                               17

SEQ ID NO: 579           moltype = AA   length = 13
FEATURE                  Location/Qualifiers
source                   1..13
                         mol_type = protein
                         organism = synthetic construct
SEQUENCE: 579
WMGWISAYNG NTN                                                   13

SEQ ID NO: 580           moltype = AA   length = 8
FEATURE                  Location/Qualifiers
source                   1..8
                         mol_type = protein
                         organism = synthetic construct
SEQUENCE: 580
ISAYNGT                                                          8

SEQ ID NO: 581           moltype = AA   length = 9
FEATURE                  Location/Qualifiers
source                   1..9
                         mol_type = protein
                         organism = synthetic construct
SEQUENCE: 581
GPRDGYNDY                                                        9

SEQ ID NO: 582           moltype = AA   length = 9
FEATURE                  Location/Qualifiers
source                   1..9
                         mol_type = protein
                         organism = synthetic construct
SEQUENCE: 582
GPRDGYNDY                                                        9

SEQ ID NO: 583           moltype = AA   length = 9
FEATURE                  Location/Qualifiers
source                   1..9
                         mol_type = protein
                         organism = synthetic construct
SEQUENCE: 583
GPRDGYNDY                                                        9

SEQ ID NO: 584           moltype = AA   length = 10
FEATURE                  Location/Qualifiers
source                   1..10
                         mol_type = protein
                         organism = synthetic construct
SEQUENCE: 584
ARGPRDGYND                                                       10

SEQ ID NO: 585           moltype = AA   length = 11
FEATURE                  Location/Qualifiers
source                   1..11
                         mol_type = protein
                         organism = synthetic construct
SEQUENCE: 585
ARGPRDGYND Y                                                     11

SEQ ID NO: 586           moltype = AA   length = 16
FEATURE                  Location/Qualifiers
```

```
source                    1..16
                          mol_type = protein
                          organism = synthetic construct
SEQUENCE: 586
RSSQSLLHSN GYNYLN                                          16

SEQ ID NO: 587            moltype = AA   length = 16
FEATURE                   Location/Qualifiers
source                    1..16
                          mol_type = protein
                          organism = synthetic construct
SEQUENCE: 587
RSSQSLLHSN GYNYLN                                          16

SEQ ID NO: 588            moltype = AA   length = 16
FEATURE                   Location/Qualifiers
source                    1..16
                          mol_type = protein
                          organism = synthetic construct
SEQUENCE: 588
RSSQSLLHSN GYNYLN                                          16

SEQ ID NO: 589            moltype = AA   length = 12
FEATURE                   Location/Qualifiers
source                    1..12
                          mol_type = protein
                          organism = synthetic construct
SEQUENCE: 589
LHSNGYNYLN WY                                              12

SEQ ID NO: 590            moltype = AA   length = 11
FEATURE                   Location/Qualifiers
source                    1..11
                          mol_type = protein
                          organism = synthetic construct
SEQUENCE: 590
QSLLHSNGYN Y                                               11

SEQ ID NO: 591            moltype = AA   length = 7
FEATURE                   Location/Qualifiers
source                    1..7
                          mol_type = protein
                          organism = synthetic construct
SEQUENCE: 591
LGSNRAS                                                    7

SEQ ID NO: 592            moltype = AA   length = 7
FEATURE                   Location/Qualifiers
source                    1..7
                          mol_type = protein
                          organism = synthetic construct
SEQUENCE: 592
LGSNRAS                                                    7

SEQ ID NO: 593            moltype = AA   length = 7
FEATURE                   Location/Qualifiers
source                    1..7
                          mol_type = protein
                          organism = synthetic construct
SEQUENCE: 593
LGSNRAS                                                    7

SEQ ID NO: 594            moltype = AA   length = 10
FEATURE                   Location/Qualifiers
source                    1..10
                          mol_type = protein
                          organism = synthetic construct
SEQUENCE: 594
LLIYLGSNRA                                                 10

SEQ ID NO: 595            moltype =    length =
SEQUENCE: 595
000

SEQ ID NO: 596            moltype = AA   length = 9
FEATURE                   Location/Qualifiers
source                    1..9
                          mol_type = protein
                          organism = synthetic construct
```

```
SEQUENCE: 596
MQPLQTPLT                                                                    9

SEQ ID NO: 597          moltype = AA  length = 9
FEATURE                 Location/Qualifiers
source                  1..9
                        mol_type = protein
                        organism = synthetic construct
SEQUENCE: 597
MQPLQTPLT                                                                    9

SEQ ID NO: 598          moltype = AA  length = 9
FEATURE                 Location/Qualifiers
source                  1..9
                        mol_type = protein
                        organism = synthetic construct
SEQUENCE: 598
MQPLQTPLT                                                                    9

SEQ ID NO: 599          moltype = AA  length = 8
FEATURE                 Location/Qualifiers
source                  1..8
                        mol_type = protein
                        organism = synthetic construct
SEQUENCE: 599
MQPLQTPL                                                                     8

SEQ ID NO: 600          moltype = AA  length = 9
FEATURE                 Location/Qualifiers
source                  1..9
                        mol_type = protein
                        organism = synthetic construct
SEQUENCE: 600
MQPLQTPLT                                                                    9

SEQ ID NO: 601          moltype = AA  length = 7
FEATURE                 Location/Qualifiers
source                  1..7
                        mol_type = protein
                        organism = synthetic construct
SEQUENCE: 601
GYTFTSY                                                                      7

SEQ ID NO: 602          moltype = AA  length = 10
FEATURE                 Location/Qualifiers
source                  1..10
                        mol_type = protein
                        organism = synthetic construct
SEQUENCE: 602
GYTFTSYGIS                                                                  10

SEQ ID NO: 603          moltype = AA  length = 5
FEATURE                 Location/Qualifiers
source                  1..5
                        mol_type = protein
                        organism = synthetic construct
SEQUENCE: 603
SYGIS                                                                        5

SEQ ID NO: 604          moltype = AA  length = 6
FEATURE                 Location/Qualifiers
source                  1..6
                        mol_type = protein
                        organism = synthetic construct
SEQUENCE: 604
TSYGIS                                                                       6

SEQ ID NO: 605          moltype = AA  length = 8
FEATURE                 Location/Qualifiers
source                  1..8
                        mol_type = protein
                        organism = synthetic construct
SEQUENCE: 605
GYTFTSYG                                                                     8

SEQ ID NO: 606          moltype = AA  length = 6
FEATURE                 Location/Qualifiers
source                  1..6
                        mol_type = protein
```

-continued

```
                     organism = synthetic construct
SEQUENCE: 606
SAYNGN                                                      6

SEQ ID NO: 607       moltype = AA  length = 10
FEATURE              Location/Qualifiers
source               1..10
                     mol_type = protein
                     organism = synthetic construct
SEQUENCE: 607
WISAYNGNTN                                                  10

SEQ ID NO: 608       moltype = AA  length = 17
FEATURE              Location/Qualifiers
source               1..17
                     mol_type = protein
                     organism = synthetic construct
SEQUENCE: 608
WISAYNGNTN YAQKLQG                                          17

SEQ ID NO: 609       moltype = AA  length = 13
FEATURE              Location/Qualifiers
source               1..13
                     mol_type = protein
                     organism = synthetic construct
SEQUENCE: 609
WMGWISAYNG NTN                                              13

SEQ ID NO: 610       moltype = AA  length = 8
FEATURE              Location/Qualifiers
source               1..8
                     mol_type = protein
                     organism = synthetic construct
SEQUENCE: 610
ISAYNGNT                                                    8

SEQ ID NO: 611       moltype = AA  length = 9
FEATURE              Location/Qualifiers
source               1..9
                     mol_type = protein
                     organism = synthetic construct
SEQUENCE: 611
MAGWELIDP                                                   9

SEQ ID NO: 612       moltype = AA  length = 9
FEATURE              Location/Qualifiers
source               1..9
                     mol_type = protein
                     organism = synthetic construct
SEQUENCE: 612
MAGWELIDP                                                   9

SEQ ID NO: 613       moltype = AA  length = 9
FEATURE              Location/Qualifiers
source               1..9
                     mol_type = protein
                     organism = synthetic construct
SEQUENCE: 613
MAGWELIDP                                                   9

SEQ ID NO: 614       moltype = AA  length = 10
FEATURE              Location/Qualifiers
source               1..10
                     mol_type = protein
                     organism = synthetic construct
SEQUENCE: 614
ARMAGWELID                                                  10

SEQ ID NO: 615       moltype = AA  length = 11
FEATURE              Location/Qualifiers
source               1..11
                     mol_type = protein
                     organism = synthetic construct
SEQUENCE: 615
ARMAGWELID P                                                11

SEQ ID NO: 616       moltype = AA  length = 16
FEATURE              Location/Qualifiers
source               1..16
```

-continued

```
                         mol_type = protein
                         organism = synthetic construct
SEQUENCE: 616
RSSQSLLHSN GYNYLD                                                   16

SEQ ID NO: 617           moltype = AA   length = 16
FEATURE                  Location/Qualifiers
source                   1..16
                         mol_type = protein
                         organism = synthetic construct
SEQUENCE: 617
RSSQSLLHSN GYNYLD                                                   16

SEQ ID NO: 618           moltype = AA   length = 16
FEATURE                  Location/Qualifiers
source                   1..16
                         mol_type = protein
                         organism = synthetic construct
SEQUENCE: 618
RSSQSLLHSN GYNYLD                                                   16

SEQ ID NO: 619           moltype = AA   length = 12
FEATURE                  Location/Qualifiers
source                   1..12
                         mol_type = protein
                         organism = synthetic construct
SEQUENCE: 619
LHSNGYNYLD WY                                                       12

SEQ ID NO: 620           moltype = AA   length = 11
FEATURE                  Location/Qualifiers
source                   1..11
                         mol_type = protein
                         organism = synthetic construct
SEQUENCE: 620
QSLLHSNGYN Y                                                        11

SEQ ID NO: 621           moltype = AA   length = 7
FEATURE                  Location/Qualifiers
source                   1..7
                         mol_type = protein
                         organism = synthetic construct
SEQUENCE: 621
LGSNRAS                                                             7

SEQ ID NO: 622           moltype = AA   length = 7
FEATURE                  Location/Qualifiers
source                   1..7
                         mol_type = protein
                         organism = synthetic construct
SEQUENCE: 622
LGSNRAS                                                             7

SEQ ID NO: 623           moltype = AA   length = 7
FEATURE                  Location/Qualifiers
source                   1..7
                         mol_type = protein
                         organism = synthetic construct
SEQUENCE: 623
LGSNRAS                                                             7

SEQ ID NO: 624           moltype = AA   length = 10
FEATURE                  Location/Qualifiers
source                   1..10
                         mol_type = protein
                         organism = synthetic construct
SEQUENCE: 624
LLIYLGSNRA                                                          10

SEQ ID NO: 625           moltype =    length =
SEQUENCE: 625
000

SEQ ID NO: 626           moltype = AA   length = 9
FEATURE                  Location/Qualifiers
source                   1..9
                         mol_type = protein
                         organism = synthetic construct
SEQUENCE: 626
```

-continued

```
MQALQTPYS                                                                9

SEQ ID NO: 627            moltype = AA  length = 9
FEATURE                   Location/Qualifiers
source                    1..9
                          mol_type = protein
                          organism = synthetic construct
SEQUENCE: 627
MQALQTPYS                                                                9

SEQ ID NO: 628            moltype = AA  length = 9
FEATURE                   Location/Qualifiers
source                    1..9
                          mol_type = protein
                          organism = synthetic construct
SEQUENCE: 628
MQALQTPYS                                                                9

SEQ ID NO: 629            moltype = AA  length = 8
FEATURE                   Location/Qualifiers
source                    1..8
                          mol_type = protein
                          organism = synthetic construct
SEQUENCE: 629
MQALQTPY                                                                 8

SEQ ID NO: 630            moltype = AA  length = 9
FEATURE                   Location/Qualifiers
source                    1..9
                          mol_type = protein
                          organism = synthetic construct
SEQUENCE: 630
MQALQTPYS                                                                9

SEQ ID NO: 631            moltype = AA  length = 7
FEATURE                   Location/Qualifiers
source                    1..7
                          mol_type = protein
                          organism = synthetic construct
SEQUENCE: 631
GYSFTSY                                                                  7

SEQ ID NO: 632            moltype = AA  length = 10
FEATURE                   Location/Qualifiers
source                    1..10
                          mol_type = protein
                          organism = synthetic construct
SEQUENCE: 632
GYSFTSYWIG                                                               10

SEQ ID NO: 633            moltype = AA  length = 5
FEATURE                   Location/Qualifiers
source                    1..5
                          mol_type = protein
                          organism = synthetic construct
SEQUENCE: 633
SYWIG                                                                    5

SEQ ID NO: 634            moltype = AA  length = 6
FEATURE                   Location/Qualifiers
source                    1..6
                          mol_type = protein
                          organism = synthetic construct
SEQUENCE: 634
TSYWIG                                                                   6

SEQ ID NO: 635            moltype = AA  length = 8
FEATURE                   Location/Qualifiers
source                    1..8
                          mol_type = protein
                          organism = synthetic construct
SEQUENCE: 635
GYSFTSYW                                                                 8

SEQ ID NO: 636            moltype = AA  length = 6
FEATURE                   Location/Qualifiers
source                    1..6
                          mol_type = protein
                          organism = synthetic construct
```

```
SEQUENCE: 636
YPGDSD                                                                    6

SEQ ID NO: 637         moltype = AA  length = 10
FEATURE                Location/Qualifiers
source                 1..10
                       mol_type = protein
                       organism = synthetic construct
SEQUENCE: 637
IIYPGDSDTR                                                               10

SEQ ID NO: 638         moltype = AA  length = 17
FEATURE                Location/Qualifiers
source                 1..17
                       mol_type = protein
                       organism = synthetic construct
SEQUENCE: 638
IIYPGDSDTR YSPSFQG                                                       17

SEQ ID NO: 639         moltype = AA  length = 13
FEATURE                Location/Qualifiers
source                 1..13
                       mol_type = protein
                       organism = synthetic construct
SEQUENCE: 639
WMGIIYPGDS DTR                                                           13

SEQ ID NO: 640         moltype = AA  length = 8
FEATURE                Location/Qualifiers
source                 1..8
                       mol_type = protein
                       organism = synthetic construct
SEQUENCE: 640
IYPGDSDT                                                                  8

SEQ ID NO: 641         moltype = AA  length = 9
FEATURE                Location/Qualifiers
source                 1..9
                       mol_type = protein
                       organism = synthetic construct
SEQUENCE: 641
GVGSVVFDY                                                                 9

SEQ ID NO: 642         moltype = AA  length = 9
FEATURE                Location/Qualifiers
source                 1..9
                       mol_type = protein
                       organism = synthetic construct
SEQUENCE: 642
GVGSVVFDY                                                                 9

SEQ ID NO: 643         moltype = AA  length = 9
FEATURE                Location/Qualifiers
source                 1..9
                       mol_type = protein
                       organism = synthetic construct
SEQUENCE: 643
GVGSVVFDY                                                                 9

SEQ ID NO: 644         moltype = AA  length = 10
FEATURE                Location/Qualifiers
source                 1..10
                       mol_type = protein
                       organism = synthetic construct
SEQUENCE: 644
ARGVGSVVFD                                                               10

SEQ ID NO: 645         moltype = AA  length = 10
FEATURE                Location/Qualifiers
source                 1..10
                       mol_type = protein
                       organism = synthetic construct
SEQUENCE: 645
ARGVGSVVFD                                                               10

SEQ ID NO: 646         moltype = AA  length = 16
FEATURE                Location/Qualifiers
source                 1..16
                       mol_type = protein
```

```
                         organism = synthetic construct
SEQUENCE: 646
RSSQSLLHSN GYNYLD                                                   16

SEQ ID NO: 647          moltype = AA   length = 16
FEATURE                 Location/Qualifiers
source                  1..16
                        mol_type = protein
                        organism = synthetic construct
SEQUENCE: 647
RSSQSLLHSN GYNYLD                                                   16

SEQ ID NO: 648          moltype = AA   length = 16
FEATURE                 Location/Qualifiers
source                  1..16
                        mol_type = protein
                        organism = synthetic construct
SEQUENCE: 648
RSSQSLLHSN GYNYLD                                                   16

SEQ ID NO: 649          moltype = AA   length = 12
FEATURE                 Location/Qualifiers
source                  1..12
                        mol_type = protein
                        organism = synthetic construct
SEQUENCE: 649
LHSNGYNYLD WY                                                       12

SEQ ID NO: 650          moltype = AA   length = 11
FEATURE                 Location/Qualifiers
source                  1..11
                        mol_type = protein
                        organism = synthetic construct
SEQUENCE: 650
QSLLHSNGYN Y                                                        11

SEQ ID NO: 651          moltype = AA   length = 7
FEATURE                 Location/Qualifiers
source                  1..7
                        mol_type = protein
                        organism = synthetic construct
SEQUENCE: 651
LGSNRAS                                                             7

SEQ ID NO: 652          moltype = AA   length = 7
FEATURE                 Location/Qualifiers
source                  1..7
                        mol_type = protein
                        organism = synthetic construct
SEQUENCE: 652
LGSNRAS                                                             7

SEQ ID NO: 653          moltype = AA   length = 7
FEATURE                 Location/Qualifiers
source                  1..7
                        mol_type = protein
                        organism = synthetic construct
SEQUENCE: 653
LGSNRAS                                                             7

SEQ ID NO: 654          moltype = AA   length = 10
FEATURE                 Location/Qualifiers
source                  1..10
                        mol_type = protein
                        organism = synthetic construct
SEQUENCE: 654
LLIYLGSNRA                                                          10

SEQ ID NO: 655          moltype =     length =
SEQUENCE: 655
000

SEQ ID NO: 656          moltype = AA   length = 9
FEATURE                 Location/Qualifiers
source                  1..9
                        mol_type = protein
                        organism = synthetic construct
SEQUENCE: 656
MQALQTPPT                                                           9
```

-continued

```
SEQ ID NO: 657              moltype = AA   length = 9
FEATURE                     Location/Qualifiers
source                      1..9
                            mol_type = protein
                            organism = synthetic construct
SEQUENCE: 657
MQALQTPPT                                                               9

SEQ ID NO: 658              moltype = AA   length = 9
FEATURE                     Location/Qualifiers
source                      1..9
                            mol_type = protein
                            organism = synthetic construct
SEQUENCE: 658
MQALQTPPT                                                               9

SEQ ID NO: 659              moltype = AA   length = 8
FEATURE                     Location/Qualifiers
source                      1..8
                            mol_type = protein
                            organism = synthetic construct
SEQUENCE: 659
MQALQTPP                                                                8

SEQ ID NO: 660              moltype = AA   length = 9
FEATURE                     Location/Qualifiers
source                      1..9
                            mol_type = protein
                            organism = synthetic construct
SEQUENCE: 660
MQALQTPPT                                                               9

SEQ ID NO: 661              moltype = AA   length = 120
FEATURE                     Location/Qualifiers
source                      1..120
                            mol_type = protein
                            organism = synthetic construct
SEQUENCE: 661
EVQLLESGPG LVKPSQTLSL TCTVSGGSIS SGGYYWSWIR QHPGKGLEWI GYIYYSGSTY       60
YNPSLKSRVT ISVDTSKNQF SLKLSSVTAA DTAVYYCART NSRITMIADW GQGTLVTVSS       120

SEQ ID NO: 662              moltype = AA   length = 110
FEATURE                     Location/Qualifiers
source                      1..110
                            mol_type = protein
                            organism = synthetic construct
SEQUENCE: 662
QSVLTQPPSV SAAPGQKVTI SCSGSSSNIG NNYVSWYQQL PGTAPKLLIY DNNKRPSGIP       60
DRFSGSKSGT SATLGITGLQ TGDEADYYCG TWDSSLSAGV FGGGTQLTVL                  110

SEQ ID NO: 663              moltype = AA   length = 120
FEATURE                     Location/Qualifiers
source                      1..120
                            mol_type = protein
                            organism = synthetic construct
SEQUENCE: 663
EVQLLESGPG LVKPSQTLSL TCTVSGGSIS SGGYYWSWIR QHPGKGLEWI GYIYYSGSTY       60
YNPSLKSRVT ISVDTSKNQF SLKLSSVTAA DTAVYYCART NSRITMIADW GQGTLVTVSS       120

SEQ ID NO: 664              moltype = AA   length = 111
FEATURE                     Location/Qualifiers
source                      1..111
                            mol_type = protein
                            organism = synthetic construct
SEQUENCE: 664
QSVLTQPPSV SAAPGQKVTI SCSGSSSNIG NNYVSWYQQL PGTAPKLLTY DNNKRPSGIP       60
DRFSGSKSGT SATLGITGLQ TGDEADYYCG TWDSSLSAGH VFGGGTKVTV L                111

SEQ ID NO: 665              moltype = AA   length = 125
FEATURE                     Location/Qualifiers
source                      1..125
                            mol_type = protein
                            organism = synthetic construct
SEQUENCE: 665
QVQLVESGGG LVQPGGSLRL SCAASGFTFS SYAMSWVRQA PGKGLEWVSA ISGSGGSTYY       60
ADSVKGRFTI SRDNSKNTLY LQMNSLRAED TAVYYCAKGS PYYYDSSGYY PLDYWGQGTL       120
VTVSS                                                                   125
```

-continued

```
SEQ ID NO: 666              moltype = AA  length = 112
FEATURE                     Location/Qualifiers
source                      1..112
                            mol_type = protein
                            organism = synthetic construct
SEQUENCE: 666
DVVMTQSPLS LPVTPGEPAS ISCRSSQSLL HSNGYNYLDW YLQKPGQSPQ LLIYLGSNRA  60
PGVPDRFSGS GSGTDFTLKI SRVEAEDVGV YYCMQALQTP LTFGPGTKLE IK          112

SEQ ID NO: 667              moltype = AA  length = 118
FEATURE                     Location/Qualifiers
source                      1..118
                            mol_type = protein
                            organism = synthetic construct
SEQUENCE: 667
EVQLLESGPG LVKPSQTLSL TCTVSGGSIS SGDYYWSWIR QPPGKGLEWI GYIYYSGSTY  60
YNPSLKSRVT ISVDTSKNQF SLKLSSVTAA DTAVYYCARG RRLLLFHWGQ GTTVTVSS    118

SEQ ID NO: 668              moltype = AA  length = 110
FEATURE                     Location/Qualifiers
source                      1..110
                            mol_type = protein
                            organism = synthetic construct
SEQUENCE: 668
QSVLTQPPSV SAAPGQKVTI SCSGSGSSIG NNYVSWYQQV PGTPPKLLIY DNNKRASGIP  60
DRFSGSKSGT SATLGITGLQ TGDEADYYCG TWDNSLSAVV FGGGTKLTVL             110

SEQ ID NO: 669              moltype = AA  length = 118
FEATURE                     Location/Qualifiers
source                      1..118
                            mol_type = protein
                            organism = synthetic construct
SEQUENCE: 669
QVQLVQSGAE VKKPGASVKV SCKASGYTFT SYAMHWVRQA PGQRLEWMGW INAGNGNTKY  60
SQKFQGRVTI TRDTSASTAY MELSSLRSED TAVYYCARGR ELLTFDYWGQ GTLVTVSS    118

SEQ ID NO: 670              moltype = AA  length = 112
FEATURE                     Location/Qualifiers
source                      1..112
                            mol_type = protein
                            organism = synthetic construct
SEQUENCE: 670
DVVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQALQTP LTFGGGTKVE IK          112

SEQ ID NO: 671              moltype = AA  length = 121
FEATURE                     Location/Qualifiers
source                      1..121
                            mol_type = protein
                            organism = synthetic construct
SEQUENCE: 671
QVQLQESGPG LVKPSQTLSL TCTVSGGSIS SGGYYWSWIR QHPGKGLEWI GYIYYSGSTY  60
YNPSLKSRVT ISVDTSKNQF SLKLSSVTAA DTAVYYCARD APLRIGAFDI WGQGTMVTVS  120
S                                                                  121

SEQ ID NO: 672              moltype = AA  length = 110
FEATURE                     Location/Qualifiers
source                      1..110
                            mol_type = protein
                            organism = synthetic construct
SEQUENCE: 672
QSVLTQPPSV SAAPGQKVTI SCSGSSSNIG NNYVSWYQQL PGTAPKLLIY DNNKRPSGIP  60
DRFSGSKSGT SATLGITRLQ TGDEADYYCG TWDSSLSAGV FGGGTKLTVL             110

SEQ ID NO: 673              moltype = AA  length = 121
FEATURE                     Location/Qualifiers
source                      1..121
                            mol_type = protein
                            organism = synthetic construct
SEQUENCE: 673
EVQLLESGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCASPV LRYFDWLPNY WGQGTLVTVS  120
S                                                                  121

SEQ ID NO: 674              moltype = AA  length = 112
FEATURE                     Location/Qualifiers
source                      1..112
                            mol_type = protein
                            organism = synthetic construct
```

```
SEQUENCE: 674
DVVMTQSPLS LPVTLGQPAS ISCRSSQSLV YSDGNTYLNW FQQRPGQSPR RLIYKVSNRD   60
SGVPDRFSGS GSGTDFTLKI SRVEAEDVGV YYCMQGTHWP PAFGPGTKVD IK           112

SEQ ID NO: 675          moltype = AA   length = 120
FEATURE                 Location/Qualifiers
source                  1..120
                        mol_type = protein
                        organism = synthetic construct
SEQUENCE: 675
EVQLVQSGAE VKKPGASVKV SCKASGYTFT SYGISWVRQA PGQGLEWMGW ISAYNGNTNY   60
AQKLQGRVTM TTDTSTSTAY MELRSLRSDD TAVYYCARDV GYSYGIFDYW GQGTLVTVSS  120

SEQ ID NO: 676          moltype = AA   length = 112
FEATURE                 Location/Qualifiers
source                  1..112
                        mol_type = protein
                        organism = synthetic construct
SEQUENCE: 676
DVVMTQSPLS LPATPGEPAS ISCRSSQSLL HSNGYNYLDW YLQKPGQSPQ LLIYLGSNRA   60
SGVPDRFSGS GSGTDFTLKI SRVEAEDVGV YYCMQALQTP YTFGQGTKVE IK           112

SEQ ID NO: 677          moltype = AA   length = 118
FEATURE                 Location/Qualifiers
source                  1..118
                        mol_type = protein
                        organism = synthetic construct
SEQUENCE: 677
EVQLVQSGAE VKKPGASVKV SCKASGYTFT SYYMHWVRQA PGQGLEWMGI INPSGGSTSY   60
AQKFQGRVTM TRDTSTSTVY MELSSLRSED TAVYYCARAP GKFPLDYWGQ GTLVTVSS    118

SEQ ID NO: 678          moltype = AA   length = 112
FEATURE                 Location/Qualifiers
source                  1..112
                        mol_type = protein
                        organism = synthetic construct
SEQUENCE: 678
DVVMTQSPLS LPVTPGEPAS ISCRSSQSLL HSNGYNYLDW YLQKPGQSPQ LLIYLGSNRA   60
SGVPDRFSGS GSGTDFTLKI SRVEAEDVGV YYCMQALQTP RTFGGGTKVE IK           112

SEQ ID NO: 679          moltype = AA   length = 125
FEATURE                 Location/Qualifiers
source                  1..125
                        mol_type = protein
                        organism = synthetic construct
SEQUENCE: 679
QVQLVQSGGG LVQPGGSLRL SCAASGFTFS SYAMSWVRQA PGKGLEWVSA ISGSGGSTYY   60
ADSVKGRFTI SRDNSKNTLY LQMNSLRAED TAVYYCARGG FWGSYRYWSA AFDIWGQGTM  120
VTVSS                                                             125

SEQ ID NO: 680          moltype = AA   length = 112
FEATURE                 Location/Qualifiers
source                  1..112
                        mol_type = protein
                        organism = synthetic construct
SEQUENCE: 680
DIVMTQSPLS LPVTPGEPAS ISCRSSQSLL HSNGYNYLDW YLQKPGQSPQ LLIYLGSNRA   60
SGVPDRFSGS GSGTDFTLKI SRVEAEDVGV YYCMQALQTP PTFGGGTKVE IK           112

SEQ ID NO: 681          moltype = AA   length = 123
FEATURE                 Location/Qualifiers
source                  1..123
                        mol_type = protein
                        organism = synthetic construct
SEQUENCE: 681
EVQLVESGAE VKKPGASVKV SCKASGYTFT SYGITWVRQA PGQGLEWMGW ISAYNGNTNY   60
AQKLQGRVTM TTDTSTSTAY MELRSLRSDD TAVYYCARHH PTGGSATIVF DYWGQGTLVT  120
VSS                                                               123

SEQ ID NO: 682          moltype = AA   length = 111
FEATURE                 Location/Qualifiers
source                  1..111
                        mol_type = protein
                        organism = synthetic construct
SEQUENCE: 682
DVVMTQSPLS LPVTPGEPAS ISCRSSQSLL HSNGYNYLDW YLQKPGQSPQ LLIYLGSNRA   60
SGVPDRFRGS GSGTDFTLKI SRVEAEDVGV YYCMQALQTP GFGQGTKVEI K            111

SEQ ID NO: 683          moltype = AA   length = 118
```

-continued

```
FEATURE             Location/Qualifiers
source              1..118
                    mol_type = protein
                    organism = synthetic construct
SEQUENCE: 683
QVQLVQSGAE VKKPGASVKV SCKASGYTFT SYYMHWVRQA PGQGLEWMGI INPSGGSTSY  60
AQKFQGRVTM TRDTSTSTVY MELSSLRSED TAVYYCARAP GKFPLDYWGQ GTLVTVSS    118

SEQ ID NO: 684       moltype = AA   length = 111
FEATURE             Location/Qualifiers
source              1..111
                    mol_type = protein
                    organism = synthetic construct
SEQUENCE: 684
DVVMTQSPLS LPVTPGEPAS ISCRSSQSLL HSNGYNYLDW YLQKPGQSPQ LLIYLGSNRA  60
SGVPDRFRGS GSGTDFTLKI SRVEAEDVGV YYCMQALQTP GFGQGTKVEI K           111

SEQ ID NO: 685       moltype = AA   length = 118
FEATURE             Location/Qualifiers
source              1..118
                    mol_type = protein
                    organism = synthetic construct
SEQUENCE: 685
EVQLVQSGAE VKKPGASVKV SCKASGYTFT SYYMHWVRQA PGQGLEWMGI INPSGGSTSY  60
AQKFQGRVTM TRDTSTSTVY MELSSLRSED TAVYYCARAP GKFPLDYWGQ GTLVTVSS    118

SEQ ID NO: 686       moltype = AA   length = 112
FEATURE             Location/Qualifiers
source              1..112
                    mol_type = protein
                    organism = synthetic construct
SEQUENCE: 686
DVVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQALQTP WTFGQGTKLE IK          112

SEQ ID NO: 687       moltype = AA   length = 122
FEATURE             Location/Qualifiers
source              1..122
                    mol_type = protein
                    organism = synthetic construct
SEQUENCE: 687
QVQLVQSGAE VKKPGESLKI SCKGSGYSFT SYWIGWVRQM PGKGLEWMGI IYPGDSDTRY  60
SPSFQGQVTI SADKSISTAY LQWSSLKASD TAMYYCARAI VGATSGYWFD PWGQGTLVTV  120
SS                                                                 122

SEQ ID NO: 688       moltype = AA   length = 112
FEATURE             Location/Qualifiers
source              1..112
                    mol_type = protein
                    organism = synthetic construct
SEQUENCE: 688
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQALQTP LTFGGGTKVE IK          112

SEQ ID NO: 689       moltype = AA   length = 121
FEATURE             Location/Qualifiers
source              1..121
                    mol_type = protein
                    organism = synthetic construct
SEQUENCE: 689
EVQLLESGGG VVQPGRSLRL SCAASGFTFS SYAMHWVRQA PGKGLEWVAV ISYDGSNKYY  60
ADSVKGRFTI SRDNSKNTLY LQMNSLRAED TAVYYCASPV LRYFDWLPNY WGQGTTVTVS  120
S                                                                  121

SEQ ID NO: 690       moltype = AA   length = 112
FEATURE             Location/Qualifiers
source              1..112
                    mol_type = protein
                    organism = synthetic construct
SEQUENCE: 690
DVVMTQSPLS LPVTLGQPAS ISCRSSQSLV YSDGNTYLNW FQQRPGQSPR RLIYKVSNRD  60
SGVPDRFSGS GSGTDFTLKI SRVEAEDVGV YYCMQGTHWP YSFGQGTKVE IK          112

SEQ ID NO: 691       moltype = AA   length = 118
FEATURE             Location/Qualifiers
source              1..118
                    mol_type = protein
                    organism = synthetic construct
SEQUENCE: 691
```

```
QVQLVQSGAE VKKPGESLKI SCKGSGYSFT SYWIGWVRQM PGKGLEWMGI IYPGDSDTRY  60
SPSFQGQVTI SADKSISTAY LQWSSLKASD TAMYYCARGH GATAFDIWGQ GTMVTVSS    118

SEQ ID NO: 692           moltype = AA  length = 112
FEATURE                  Location/Qualifiers
source                   1..112
                         mol_type = protein
                         organism = synthetic construct
SEQUENCE: 692
DVVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQALQTP PTFGPGTKLE IK          112

SEQ ID NO: 693           moltype = AA  length = 123
FEATURE                  Location/Qualifiers
source                   1..123
                         mol_type = protein
                         organism = synthetic construct
SEQUENCE: 693
QVQLVQSGAE VKKPGSSVKV SCKASGGTFS SYAISWVRQA PGQGLEWMGG IIPIFGTANY  60
AQKFQGRVTI TADKSTSTAY MELSSLRSED TAVYYCARDR YYDSSGYYLM DPWGQGTLVT  120
VSS                                                                123

SEQ ID NO: 694           moltype = AA  length = 112
FEATURE                  Location/Qualifiers
source                   1..112
                         mol_type = protein
                         organism = synthetic construct
SEQUENCE: 694
DIVMTQSPLS SPVTLGQPAS ISCRSSQSLV HSDGNTYLSW LQQRPGQPPR LLIYKISNRF  60
SGVPDRFSGS GAGTDFTLKI SRVEAEDVGV YYCMQATQFP LTFGGGTRLE IK          112

SEQ ID NO: 695           moltype = AA  length = 118
FEATURE                  Location/Qualifiers
source                   1..118
                         mol_type = protein
                         organism = synthetic construct
SEQUENCE: 695
QVQLVQSGAE VKKPGASVKV SCKASGYTFT SYYMHWVRQA PGQGLEWMGI INPSGGSTSY  60
AQKFQGRVTM TRDTSTSTVY MELSSLRSED TAVYYCARAP GKFPLDYWGQ GTLVTVSS    118

SEQ ID NO: 696           moltype = AA  length = 112
FEATURE                  Location/Qualifiers
source                   1..112
                         mol_type = protein
                         organism = synthetic construct
SEQUENCE: 696
DVVMTQSPLS LPVTPGEPAS ISCRSSQSLL KSNGYNYLDW YLQKPGQSPQ LLIYLGSNRA  60
SGVPDRFSGS GSGTDFSLKI RRVEAEDVGV YYCMQTLQTP YTFGQGTKLE IK          112

SEQ ID NO: 697           moltype = AA  length = 121
FEATURE                  Location/Qualifiers
source                   1..121
                         mol_type = protein
                         organism = synthetic construct
SEQUENCE: 697
QVQLVESGPG LVKPSQTLSL TCTVSGGSIS SGGYYWSWIR QHPGKGLEWI GYIYYSGSTY  60
YNPSLKSRVT ISVDTSKNQF SLKLSSVTAA DTAVYYCARS GAAGIPWFDP WGQGTLVTVS  120
S                                                                  121

SEQ ID NO: 698           moltype = AA  length = 110
FEATURE                  Location/Qualifiers
source                   1..110
                         mol_type = protein
                         organism = synthetic construct
SEQUENCE: 698
QSVLTQPPSV SAAPGQKVTI SCSGSSSNIG NNYVSWYQQL PGTAPKLLIY ENNERPSGIP  60
DRLSGSKSGT SATLAITGLQ TGDEADYYCG TWDSSLSAVV FGGGTKLTVL             110

SEQ ID NO: 699           moltype = AA  length = 118
FEATURE                  Location/Qualifiers
source                   1..118
                         mol_type = protein
                         organism = synthetic construct
SEQUENCE: 699
QVQLVQSGAE VKKPGASVKV SCKASGYTFT SYGISWVRQA PGRGLEWMGW ISAYNGNTNY  60
AQKLQGRVTM TTDTSTSTAY MELRSLRSDD TAVYYCARGP RDGYNDYWGQ GTLVTVSS    118

SEQ ID NO: 700           moltype = AA  length = 112
FEATURE                  Location/Qualifiers
```

-continued

```
source                   1..112
                         mol_type = protein
                         organism = synthetic construct
SEQUENCE: 700
DVVMTQSPLS LPVTPGEPAS ISCRSSQSLL HSNGYNYLNW YLQKPGQSPQ LLIYLGSNRA  60
SGVPDRFSGS GSGTDFTLKI SRVEAEDVGV YYCMQPLQTP LTFGGGTKLE IK          112

SEQ ID NO: 701          moltype = AA  length = 118
FEATURE                 Location/Qualifiers
source                  1..118
                        mol_type = protein
                        organism = synthetic construct
SEQUENCE: 701
QVQLVQSGAE VKKPGASVKV SCKASGYTFT SYGISWVRQA PGQGLEWMGW ISAYNGNTNY  60
AQKLQGRVTM TTDTSTSTAY MELRSLRSDD TAVYYCARMA GWELIDPWGQ GTLVTVSS    118

SEQ ID NO: 702          moltype = AA  length = 112
FEATURE                 Location/Qualifiers
source                  1..112
                        mol_type = protein
                        organism = synthetic construct
SEQUENCE: 702
DVVMTQSPLS LPVTPGEPAS ISCRSSQSLL HSNGYNYLDW YLQKPGKSPQ LLIYLGSNRA  60
SGVPDRFSGS GSGTDFTLKI SRVEAEDVGV YYCMQALQTP YSFGQGTKVE IK          112

SEQ ID NO: 703          moltype = AA  length = 118
FEATURE                 Location/Qualifiers
source                  1..118
                        mol_type = protein
                        organism = synthetic construct
SEQUENCE: 703
EVQLLESGAE VKKPGESLKI SCKGSGYSFT SYWIGWVRQM PGKGLEWMGI IYPGDSDTRY  60
SPSFQGQVTI SADKSISTAY LQWSSLKASD TAMYYCARGV GSVVFDYWGQ GTLVTVSS    118

SEQ ID NO: 704          moltype = AA  length = 112
FEATURE                 Location/Qualifiers
source                  1..112
                        mol_type = protein
                        organism = synthetic construct
SEQUENCE: 704
DVVMTQSPLP LPVTPGEPAS ISCRSSQSLL HSNGYNYLDW YLQKPGQSPQ LLIYLGSNRA  60
SGVPDRFSGS GSGTDFTLKI SRVEAEDVGV YYCMQALQTP PTFGQGTKVE IK          112
```

METHODS FOR TREATING DIABETIC KIDNEY DISEASE AND GLOMERULAR DISEASE

1. CROSS-REFERENCE TO RELATED APPLICATIONS

This application is a continuation of U.S. application Ser. No. 18/292,826, filed on Jan. 26, 2024, which is the National Stage of International Application No. PCT/EP2022/071139, filed on Jul. 27, 2022, which claims the benefit of and priority to U.S. Provisional Application No. 63/302,460, filed on Jan. 24, 2022, and 63/226,125, filed on Jul. 27, 2021, which are incorporated herein by reference in their entireties for all purposes.

1.1. Sequence Listing

The instant application contains a Sequence Listing which has been submitted electronically via Patent Center and is hereby incorporated by reference in its entirety. Said XML copy, created on Aug. 20, 2024, is named 49199US_Sequencelisting.xml, and is 601,375 bytes in size.

2. BACKGROUND OF INVENTION

Diabetes mellitus type 1 (T1D) and type 2 (T2D) collectively affect at least 347 million people worldwide, and prevalence is increasing. Diabetes is characterized by hyperglycemia and complications that greatly impact patient quality and duration of life, placing a major economic burden on society. Research conducted by the American Diabetes Association placed the national economic burden of diabetes in the USA in 2017 at $327 billion. This represents a 26% increase from 245 billion in 2012 when the cost was last examined.

There is no current cure for T1D or T2D. Most therapies help patients manage the symptoms to a certain extent, but diabetics still face multiple long-term health complications. Among these complications is kidney damage, which can progress to end-stage renal disease (ESRD). Diabetes was the primary cause of kidney failure in 44% of all new cases in 2011. Given the prevalence and severity of complications associated with diabetes, in particular kidney disease and its progression, there is a need for therapeutic agents that delay onset and progression of kidney disease in diabetes.

Kidney damage also has other etiologies. There is a need for therapeutic agents that delay onset and progression of kidney disease caused by disorders other than diabetes. There is a particular need for therapeutic agents that treat glomerular disorders.

3. SUMMARY OF THE INVENTION

As detailed in the experimental examples in this disclosure, we have discovered that the protein, neuroblastoma suppressor of tumorgenicity 1 (NBL1), is directly toxic to renal cells, including podocytes and tubular cells. The toxic effect is not mediated through inhibition of renal BMP proteins; we show that BMPs are not expressed in and are not secreted by kidney cells. Moreover, we have discovered that NBL1 is also not expressed in kidney cells, but is expressed in circulating immune cells. Neutralizing NBL1 with an antagonist, either sBMP2 or anti-NBL1 monoclonal antibodies, prevents toxicity in vitro. Finally, we demonstrate that NBL1 is elevated in Type 1 Diabetes and Type 2 Diabetes. Inhibition of NBL1 is therefore a new therapeutic approach for preventing onset and progression of kidney damage caused by circulating NBL1, and in particular, in a patient with type 1 or type 2 diabetes. Inhibition of NBL1 will also be effective in treating non-diabetes glomerular diseases in which damage is mediated by NBL1.

Accordingly, in a first aspect, methods are provided for delaying onset or progression of kidney damage in a subject who has type 1 diabetes or type 2 diabetes or a glomerular disease. The method comprises administering to the subject an effective amount of an agent capable of inhibiting NBL1 activity, in particular, capable of inhibiting NBL1 toxicity on human podocytes. In some embodiments, the method prevents onset of or slows decline in kidney function.

In a further aspect, methods are provided for slowing decline in kidney function in a subject who has type 1 or type 2 diabetes or a glomerular disease. The method comprises administering to the subject an effective amount of an agent capable of inhibiting NBL1 activity, in particular, capable of inhibiting NBL1 toxicity on human podocytes.

In a yet further aspect, methods are provided for treating diabetic kidney disease (DKD) in a subject who has type 1 or type 2 diabetes or a glomerular disease. The method comprises administering to the subject an effective amount of an agent capable of inhibiting NBL1 activity, in particular, capable of inhibiting NBL1 toxicity on human podocytes.

In some embodiments of these methods, the agent is capable of binding to NBL1. In some embodiments the agent is capable of binding to human NBL1.

In some embodiments the agent is an antibody, or an antigen binding fragment of an antibody, that is capable of binding to human NBL1.

In some embodiments the antibody or antigen-binding fragment comprises three heavy chain CDRs and three light chain CDRs having sequences selected from:
- a) SEQ ID NOs: 3, 8, and 13 and SEQ ID NOs: 18, 23, and 28 (antibody E05a);
- b) SEQ ID NOs: 33, 38, and 43 and SEQ ID NOs: 48, 53, and 58 (antibody H08);
- c) SED ID NOs: 63, 68, and 73 and SED ID NOs: 78, 83, and 88 (antibody F06);
- d) SEQ ID NOs: 93, 98, and 103 and SEQ ID NOs: 108, 113, and 118 (antibody A12);
- e) SED ID NOs: 123, 128, and 133 and SED ID NOs: 138, 143, and 148 (antibody G01);
- f) SED ID NOs: 153, 158, and 163 and SED ID NOs: 168, 173 and 178 (antibody E11);
- g) SEQ ID NOs: 183, 188, and 193 and SEQ ID NOs: 198, 203, and 208 (antibody B06);
- h) SED ID NOs: 213, 218, and 223 and SED ID NOs: 228, 233, and 238 (antibody D12);
- i) SED ID NOs: 243, 248, and 253 and SED ID NOs: 258, 263 and 268 (antibody H01);
- j) SED ID NOs: 273, 278, and 283 and SED ID NOs: 288, 293, and 298 (antibody C11);
- k) SED ID NOs: 303, 308, and 313 and SED ID NOs: 318, 323, and 328 (antibody E05b);
- l) SED ID NOs: 333, 338, and 343 and SED ID NOs: 348, 353 and 358 (antibody F10);
- m) SED ID NOs: 363, 368 and 373 and SED ID NOs: 378, 383 and 388 (antibody G10);
- n) SEQ ID NOs: 393, 398, and 403 and SEQ ID NOs: 408, 413, and 418 (antibody E04);
- o) SED ID NOs: 423, 428, and 433 and SED ID NOs: 438, 443, and 448 (antibody E07);
- p) SED ID NOs: 453, 458, and 463 and SED ID NOs: 468, 473, and 478 (antibody E12);

q) SED ID NOs: 483, 488, and 493 and SED ID NOs: 498, and 503, and 508 (antibody D08);

r) SED ID NOs: 513, 518, and 523 and SED ID NOs: 528, 533, and 538 (antibody E10);

S) SEQ ID NOs: 543, 548, and 553 and SEQ ID NOs: 558, 563, and 568 (antibody D06); and t) SED ID NOs: 573, 578, and 583 and SED ID NOs: 588, 593, and 598 (antibody E01), or having sequences that differ from the selected sets of CDR sequences (a)-(t) by at most two conservative amino acid changes in each CDR.

In some embodiments of the methods, the antibody or antigen-binding fragment comprises three heavy chain CDRs and three light chain CDRs with sequences identical to the selected CDRs. In some embodiments the three heavy chain CDRs and three light chain CDRs have sequences selected from:

b) SEQ ID NOs: 33, 38, and 43 and SEQ ID NOs: 48, 53 and 58 (antibody H08);

d) SEQ ID NOs: 93, 98, and 103 and SEQ ID NOs: 108, 113, and 118 (antibody A12);

g) SEQ ID NOs: 183, 188, and 193 and SEQ ID NOs: 198, 203, and 208 (antibody B06);

n) SEQ ID NOs: 393, 398, and 403 and SEQ ID NOs: 408, 413, and 418 (antibody E04);

s) SEQ ID NOs: 543, 548, and 553 and SEQ ID NOs: 558, 563, and 568 (antibody D06); and t) SEQ ID NOs: 573, 578, and 583 and SEQ ID NOs: 588, 593, and 598 (antibody E01), or having sequences that differ from the selected sets of CDR sequences b), d), g), n) s), and t) by at most two conservative amino acid changes in each CDR.

In some embodiments the antibody or antigen-binding fragment comprises three heavy chain CDRs and three light chain CDRs with sequences identical to the selected CDRs.

In some embodiments the antibody framework regions are human antibody framework regions.

In some embodiments the antibody is a full length bivalent monospecific monoclonal antibody. In some embodiments the antibody comprises human IgG1, IgG2, or IgG4 heavy chain constant regions. In some embodiments the antibody comprises a human IgG1 constant region. In some embodiments the antibody Fc region has engineered mutations that reduce antibody binding to at least one type of Fc receptor and/or reduce complement fixation. In some embodiments the antibody is a Fab, optionally wherein the Fab is PEGylated. In some embodiments the antibody or antigen binding fragment is further capable of binding to cynomolgus monkey NBL1. In some embodiments the antibody or antigen binding fragment is further capable of binding to mouse NBL1.

In some embodiments the antibody or antigen binding fragment has a binding affinity ($K_D$) for human NBL1 of less than 100 nM. In some embodiments the antibody or antigen binding fragment has a binding affinity ($K_D$) for human NBL1 of less than 10 nM. In some embodiments the antibody or antigen binding fragment has a binding affinity ($K_D$) for human NBL1 of less than 5 nM. In some embodiments the antibody or antigen binding fragment has a binding affinity ($K_D$) for human NBL1 of less than 1 nM.

In some embodiments, the agent comprises a bone morphogenetic protein (BMP) or soluble fragment thereof. In some embodiments the agent comprises a soluble fragment of human BMP-2. In some particular embodiments the agent further comprises a moiety that extends serum half-life. In some embodiments the half-life extension moiety is an antibody Fc domain. In some embodiments the half-life extension moiety is at least one covalently linked polyethylene glycol (PEG) moiety.

In some embodiments the agent is capable of inhibiting dimerization of NBL1.

In some embodiments the agent is capable of inhibiting NBL1 expression.

In some embodiments, the agent is administered parenterally. In some embodiments the agent is administered intravenously. In some embodiments the agent is administered subcutaneously. In some embodiments the agent is administered for at least 3 months. In some embodiments the agent is administered for at least 6 months. In some embodiments the agent is administered for at least 12 months.

In some embodiments the subject has elevated pre-treatment plasma levels of NBL1. In some embodiments the subject has type 1 diabetes. In some embodiments the subject has type 2 diabetes. In some embodiments the subject has a glomerular disease. In some embodiments the subject with glomerular disease does not have type 1 diabetes or type 2 diabetes. In some embodiments the glomerular disease is selected from the group consisting of focal segmental glomerulosclerosis (FSGS), chronic glomerulopathies, hereditary nephritis, and minimal change disease.

In another aspect, antibodies or antigen binding fragments capable of binding to NBL1 and inhibiting NBL1-induced toxicity of human podocytes are provided.

In some embodiments, the antibody or antigen-binding fragment comprises three heavy chain CDRs and three light chain CDRs having sequences selected from:

a) SEQ ID NOs: 3, 8, and 13 and SEQ ID NOs: 18, 23, and 28 (antibody E05a);

b) SEQ ID NOs: 33, 38, and 43 and SEQ ID NOs: 48, 53, and 58 (antibody H08);

c) SED ID NOs: 63, 68, and 73 and SED ID NOs: 78, 83, and 88 (antibody F06);

d) SEQ ID NOs: 93, 98, and 103 and SEQ ID NOs: 108, 113, and 118 (antibody A12);

e) SED ID NOs: 123, 128, and 133 and SED ID NOs: 138, 143, and 148 (antibody G01);

f) SED ID NOs: 153, 158, and 163 and SED ID NOs: 168, 173 and 178 (antibody E11);

g) SEQ ID NOs: 183, 188, and 193 and SEQ ID NOs: 198, 203, and 208 (antibody B06);

h) SED ID NOs: 213, 218, and 223 and SED ID NOs: 228, 233, and 238 (antibody D12);

i) SED ID NOs: 243, 248, and 253 and SED ID NOs: 258, 263 and 268 (antibody H01);

j) SED ID NOs: 273, 278, and 283 and SED ID NOs: 288, 293, and 298 (antibody C11);

k) SED ID NOs: 303, 308, and 313 and SED ID NOs: 318, 323, and 328 (antibody E05b);

l) SED ID NOs: 333, 338, and 343 and SED ID NOs: 348, 353 and 358 (antibody F10);

m) SED ID NOs: 363, 368 and 373 and SED ID NOs: 378, 383 and 388 (antibody G10);

n) SEQ ID NOs: 393, 398, and 403 and SEQ ID NOs: 408, 413, and 418 (antibody E04);

o) SED ID NOs: 423, 428, and 433 and SED ID NOs: 438, 443, and 448 (antibody E07);

p) SED ID NOs: 453, 458, and 463 and SED ID NOs: 468, 473, and 478 (antibody E12);

q SED ID NOs: 483, 488, and 493 and SED ID NOs: 498, and 503, and 508 (antibody D08);

r) SED ID NOs: 513, 518, and 523 and SED ID NOs: 528, 533, and 538 (antibody E10);

s) SEQ ID NOs: 543, 548, and 553 and SEQ ID NOs: 558, 563, and 568 (antibody D06); and t) SED ID NOs: 573, 578, and 583 and SED ID NOs: 588, 593, and 598 (antibody E01), or having sequences that differ from the CDR sequences selected from (a)-(t) by at most two conservative amino acid substitutions in each CDR. In some embodiments, the antibody or antigen-binding fragment comprises three heavy chain CDRs and three light chain CDRs with sequences identical to one of the selected sets of CDRs (a)-(t).

In some embodiments, the three heavy chain CDRs and three light chain CDRs have sequences selected from:

b) SEQ ID NOs: 33, 38, and 43 and SEQ ID NOs: 48, 53 and 58 (antibody H08);

d) SEQ ID NOs: 93, 98, and 103 and SEQ ID NOs: 108, 113, and 118 (antibody A12);

g) SEQ ID NOs: 183, 188, and 193 and SEQ ID NOs: 198, 203, and 208 (antibody B06);

n) SEQ ID NOs: 393, 398, and 403 and SEQ ID NOs: 408, 413, and 418 (antibody E04);

s) SEQ ID NOs: 543, 548, and 553 and SEQ ID NOs: 558, 563, and 568 (antibody D06); and t) SEQ ID NOs: 573, 578, and 583 and SEQ ID NOs: 588, 593, and 598 (antibody E01), or having sequences that differ from the selected CDR sequences b), d), g), n) s), and t) by at most two conservative amino acid substitutions in each CDR. In some embodiments, the antibody or antigen-binding fragment comprises three heavy chain CDRs and three light chain CDRs with sequences identical to the selected CDRs b), d), g), n), s), or t).

In some embodiments, the antibody or antigen-binding fragment framework regions are human antibody framework regions.

In some embodiments, the antibody or antigen binding fragment is a full length bivalent monospecific monoclonal antibody. In some embodiments, the antibody comprises human IgG1, IgG2, or IgG4 heavy chain constant regions. In some embodiments, the antibody comprises a human IgG1 constant region. In some embodiments, the antibody Fc region has engineered mutations that reduce antibody binding to FcRγ and/or reduce complement fixation.

In some embodiments, the antigen binding fragment is a Fab, optionally wherein the Fab is PEGylated.

In some embodiments, the antibody or antigen binding fragment is further capable of binding to cynomolgus monkey NBL1. In some embodiments, the antibody or antigen binding fragment is further capable of binding to mouse NBL1.

In some embodiments, the antibody or antigen binding fragment has a binding affinity ($K_D$) for human NBL1 of less than 100 nM, 10 nM, 5 nM or 1 nM.

In another aspect, pharmaceutical compositions are provided. The compositions comprise the anti-NBL1 antibody or antigen binding fragment, and a pharmaceutically acceptable carrier. In some embodiments, the composition is formulated for parenteral administration. In some embodiments, the composition is formulated for intravenous administration. In some embodiments, the composition is formulated for subcutaneous administration.

4. BRIEF DESCRIPTION OF THE SEVERAL VIEWS OF THE DRAWINGS

These and other features, aspects, and advantages of the present invention will become better understood with regard to the following description, and accompanying drawings, where:

FIGS. 1A-1D are bar graphs summarizing cell death analysis in human kidney cells. FIG. 1A shows data from human podocytes (HuPodo) cultured with escalating doses of recombinant human NBL1, from 0.2 μg/ml to 2 μg/ml. FIG. 1B shows data from human mesangial cells (HuMRC) cultured in the presence of 2 μg/ml recombinant human NBL1. FIG. 1C shows data from human renal tubular cells (HuK2) cultured in the presence of 2 μg/ml recombinant human NBL1. FIG. 1D shows data from control human umbilical vein endothelial cells (Huvec) cultured in the presence of 2 μg/ml recombinant human NBL1.

FIGS. 2A-2B depict representative images of confocal analysis conducted on human podocytes cultured with NBL1 at 2 μg/ml (FIG. 2A) or left untreated (FIG. 2B). The podocytes were stained with Apoptag, a marker for apoptosis, and Synaptopodin, a marker for podocytes. FIG. 2C is a bar graph quantifying the percentage of human podocytes that are double positive for Apoptag and Synaptopodin ($Syn^+Apo^+$). The experiment demonstrates NBL1-induced apoptosis of differentiated human podocytes (arrows in FIG. 2B, quantified in FIG. 2C).

Figure 5A:
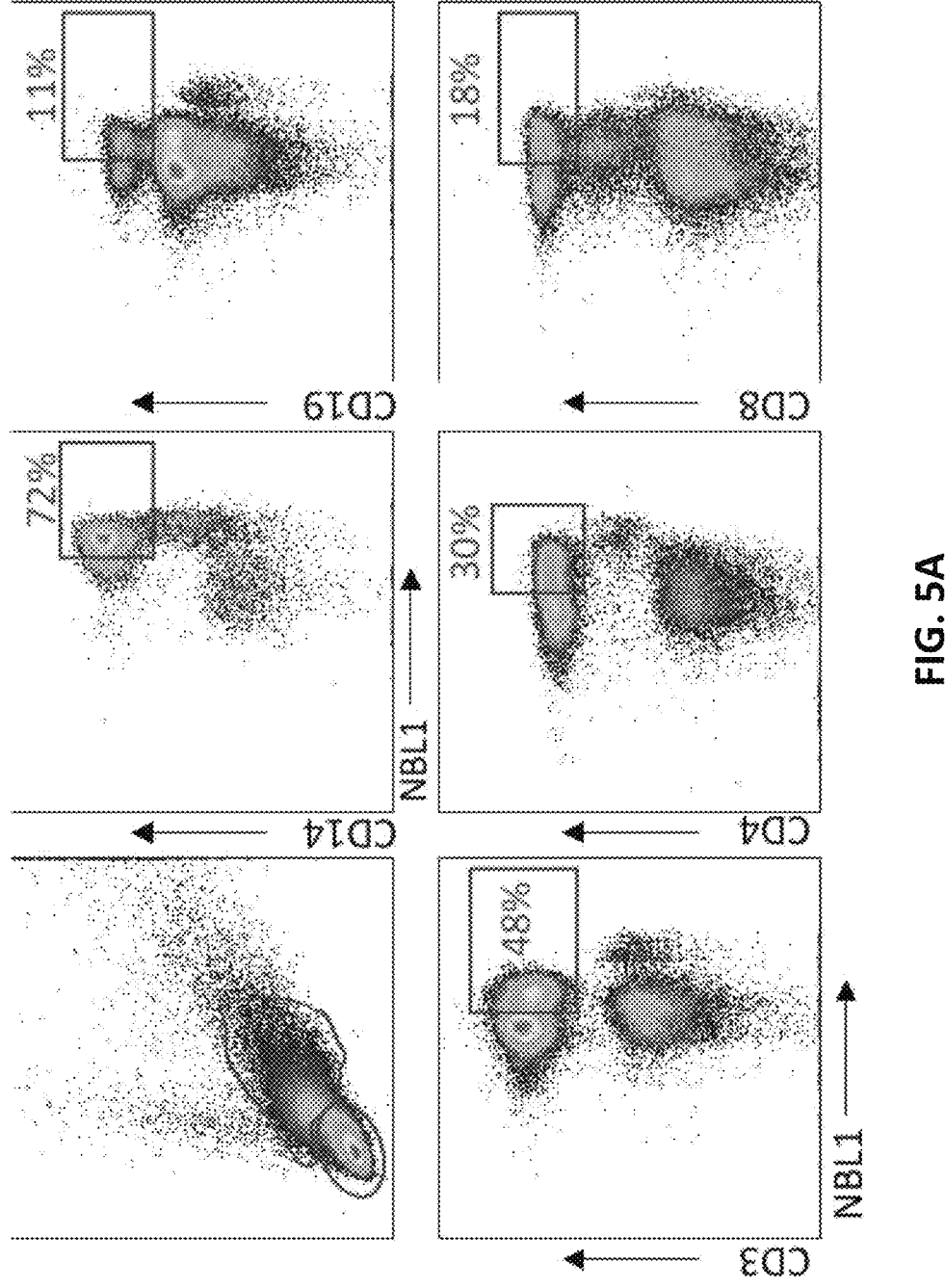
Figure 5B:
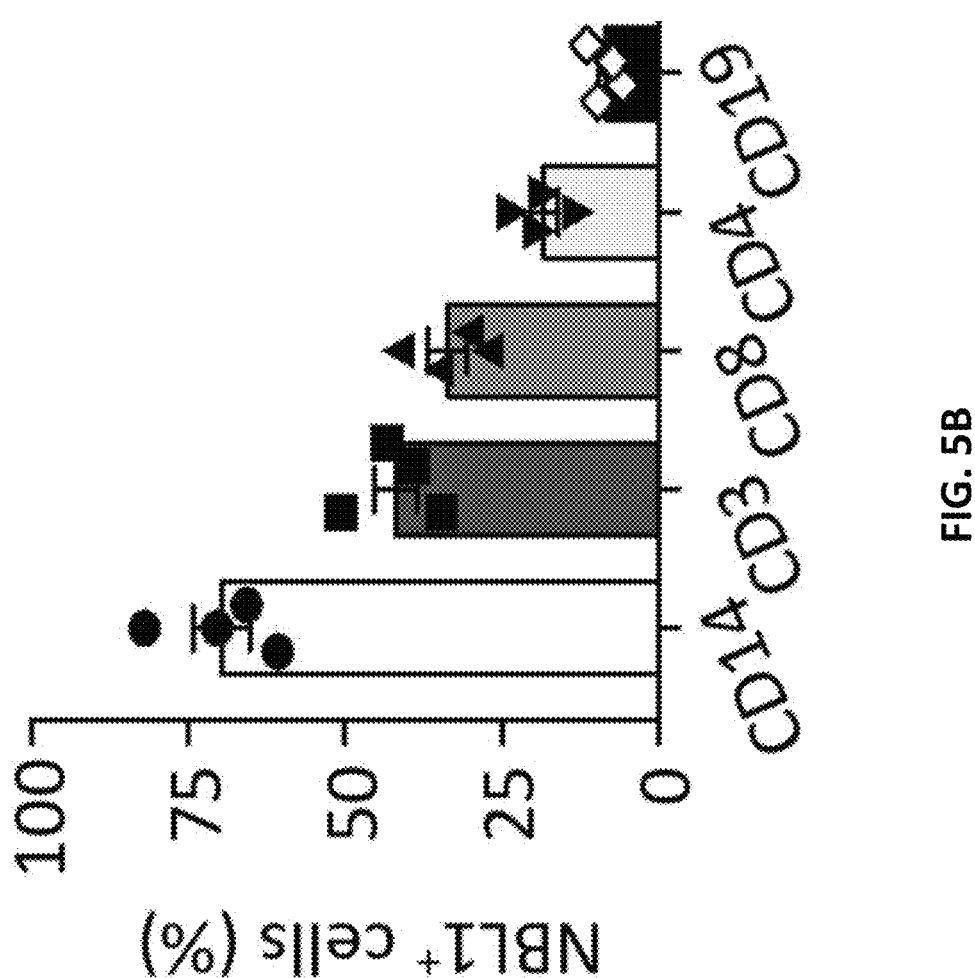
Figure 5C:
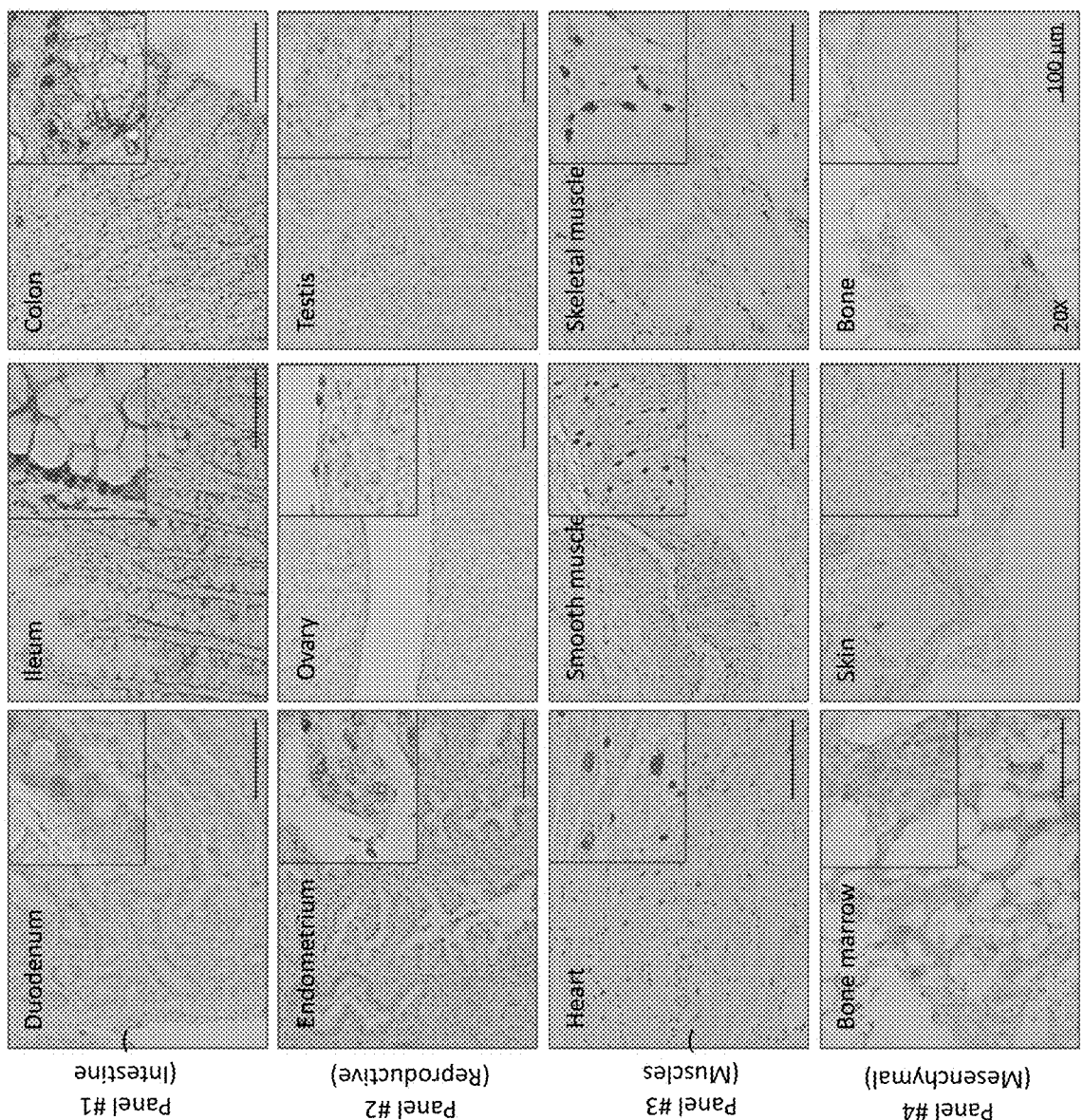
Figure 5D:
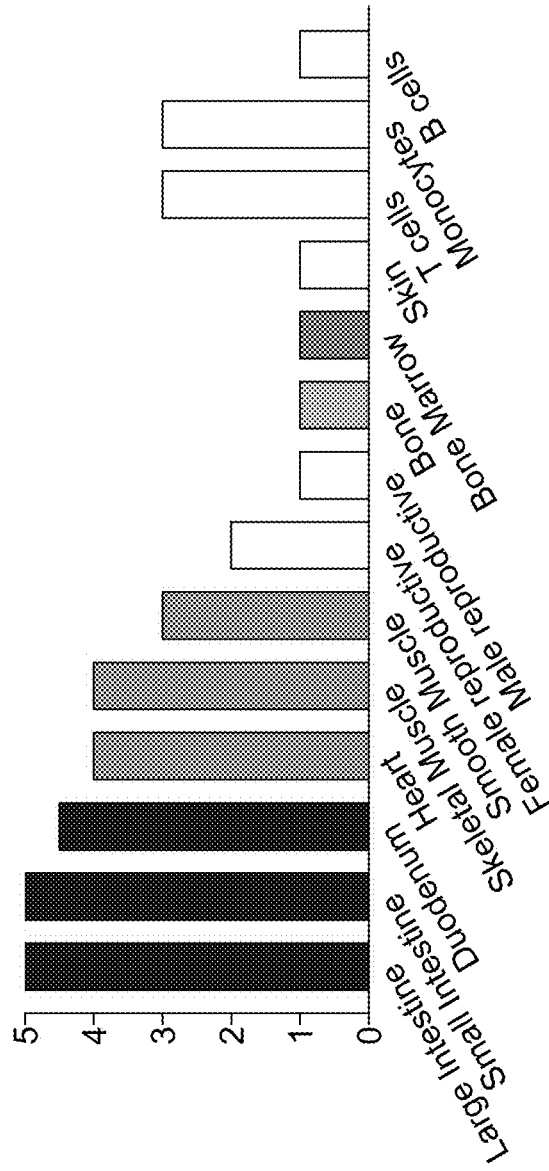

FIGS. 5A-5B depict the high expression of NBL1 protein in T cells and various T cell subsets ($CD3^+$, $CD4^+$ and $CD8^+$ T cells) and in myeloid cells ($CD14^+$) using flow-cytometry analysis. The upper left panel of FIG. 5A depicts physical gating on monocytes (upper gate) and lymphocytes (lower gate). All analysis was conducted on peripheral blood mononuclear cells (PBMCs) isolated from blood samples of healthy volunteers. FIGS. 5C-5D depict the results of an NBL1 Atlas study surveying NBL1 expression in various human tissues by immunohistochemistry. FIG. 5C shows images of various tissue samples illustrating the presence of NBL1 through immunohistochemistry techniques. FIG. 5D is a bar graphing showing high expression of NBL1 protein in intestinal and muscular tissues.

Figure 6:
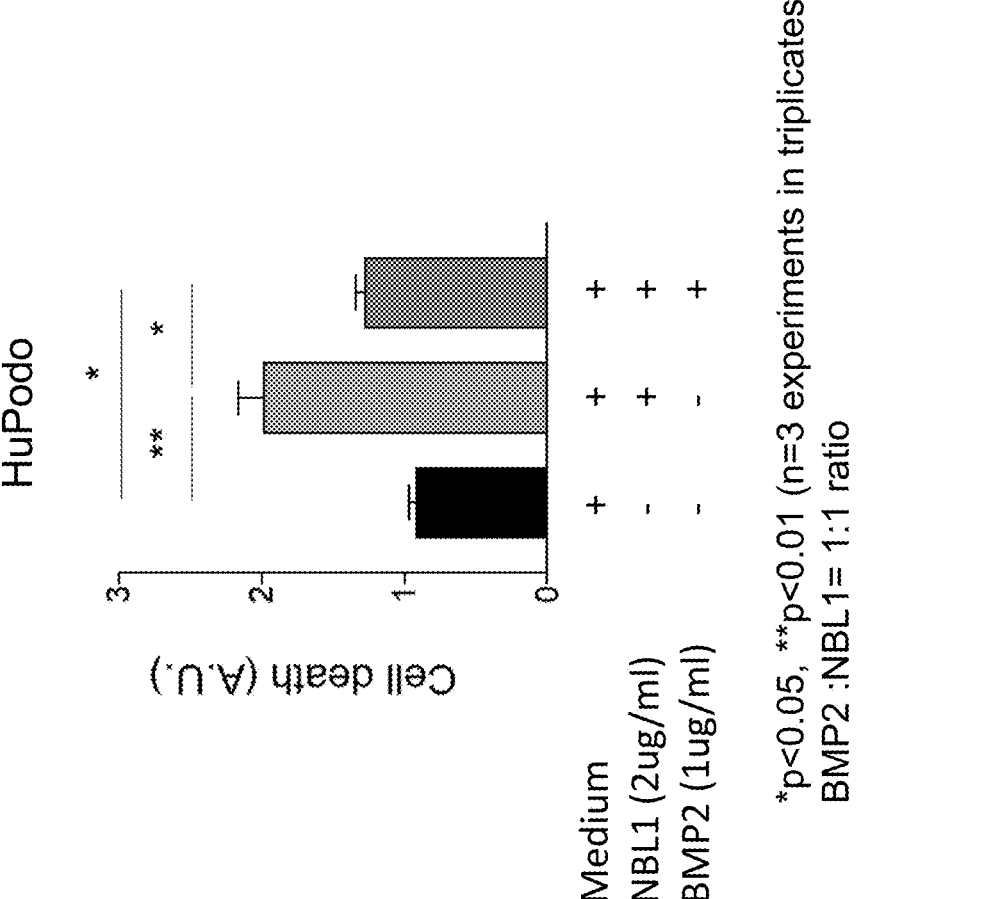

FIG. 6 depicts the neutralizing effect of soluble BMP2 on NBL1-mediated apoptosis. Human podocytes were cultured in the presence of NBL1 (2 μg/ml) and in the presence/absence of soluble BMP2 (1 μg/ml) for 48 hours.

Figure 7B:
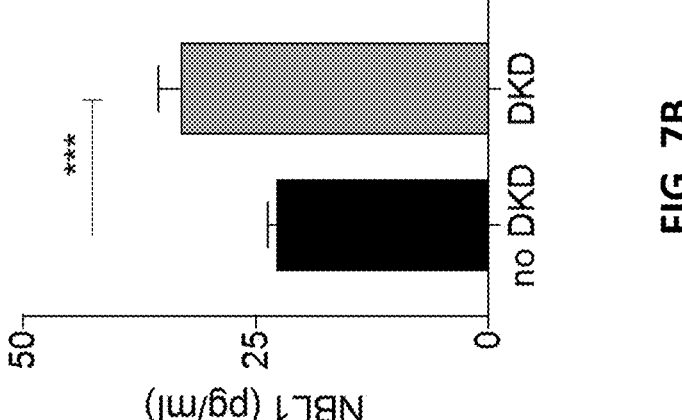
Figure 7A:
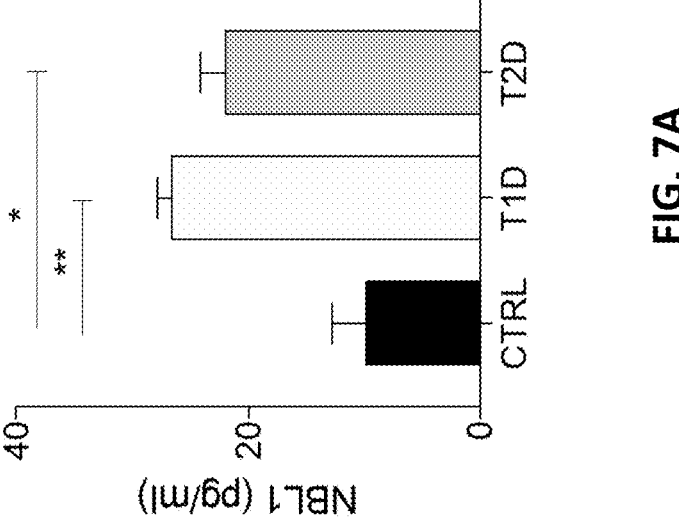

FIGS. 7A-7B depict increased NBL1 serum levels measured by ELISA, with FIG. 7A comparing levels in patients with long-standing type 1 diabetes (T1D), type 2 diabetes (T2D), and non-diabetic subjects (CTRL), with FIG. 7B showing NBL1 serum levels in patients with diabetic kidney disease (DKD) stage 2-3 compared to those without DKD.

Figure 8:
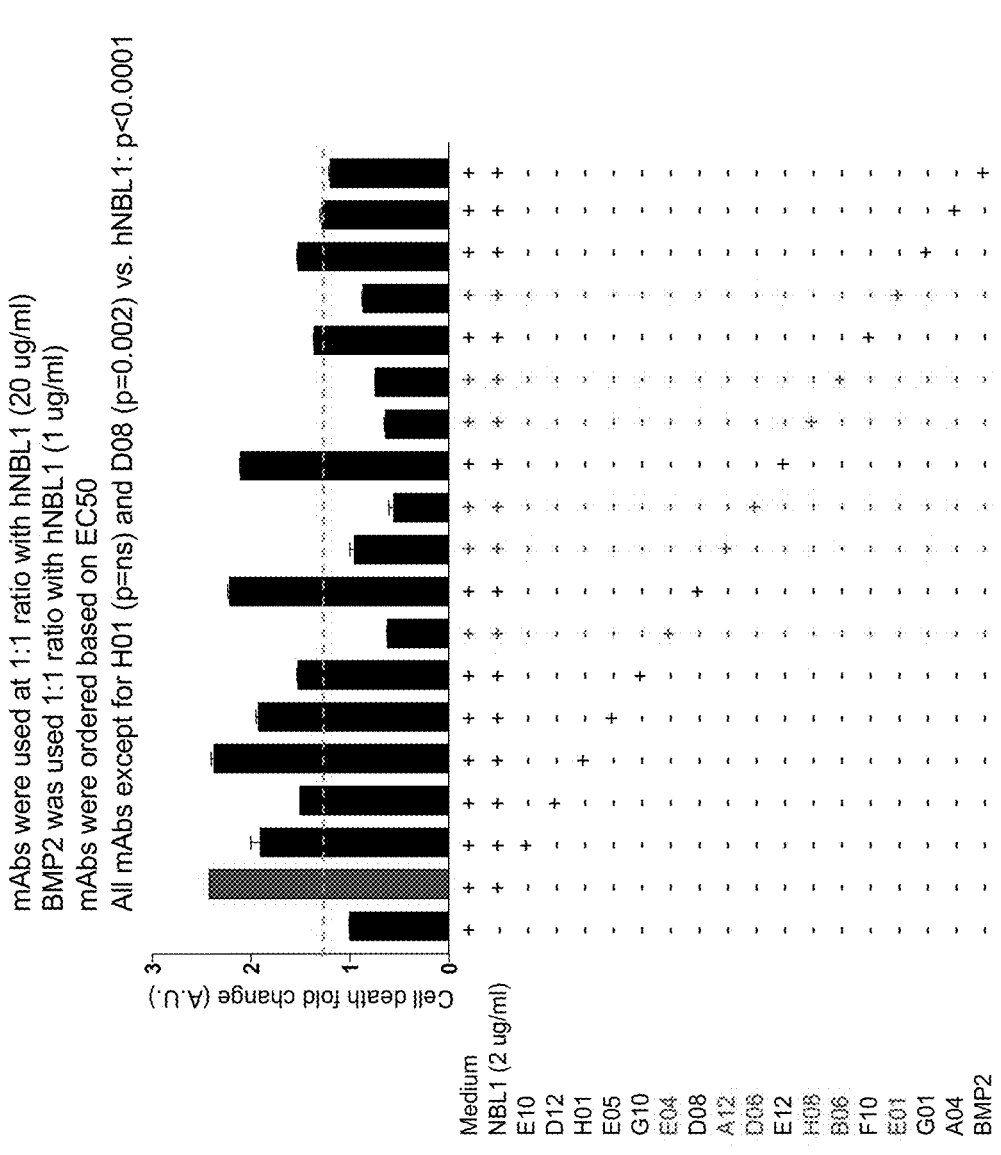

FIG. 8 are bar graphs quantifying cell death in human podocytes cultured in the presence of NBL1 (2 μg/ml) in the presence and absence of either anti-NBL1 antibodies (20 μg/ml) or soluble BMP2 (1 μg/ml). The left-most bar shows data from cells incubated in medium alone, without NBL1, and without treatment with antibody or sBMP.

5. DETAILED DESCRIPTION OF THE INVENTION

5.1. Definitions

Unless defined otherwise, all technical and scientific terms used herein have the meaning commonly understood by a person skilled in the art to which this disclosure belongs.

The terms "individual" and "subject" are used interchangeably and refer to an animal to be treated, including but not limited to humans; non-human primates; rodents, including rats and mice; bovines; equines; ovines; felines; and canines.

The term "patient" refers to a human subject.

The terms "treating," "treatment," and grammatical variations thereof are used in the broadest sense understood in the clinical arts. Accordingly, the terms do not require cure or complete remission of disease and encompass obtaining any clinically desired pharmacologic and/or physiologic effect. As used herein, "treating diabetic kidney disease (DKD)" explicitly encompasses delaying onset of kidney damage, delaying progression of kidney damage, and slowing decline in kidney function in patients with type 1 or type 2 diabetes or a glomerular disorder.

The phrase "therapeutically effective amount" refers to the amount of a compound that, when administered to a mammal or other subject for treating a disease, condition, or disorder, is sufficient to effect treatment of the disease, condition, or disorder, as treatment is defined herein. Determining the "therapeutically effective amount" is within the skill in the art.

Neuroblastoma suppressor of tumorigenicity 1 (NBL1) is a founding member of the DAN (differential screening-selected gene aberrant in neuroblastoma) gene family. Members of the DAN gene family are expressed during development and function as bone morphogenetic protein (BMP) antagonists; DAN proteins bind to BMPs and prevent them from interacting with BMP receptors. Neuroblastoma suppressor of tumorigenicity 1 (NBL1), also known as DIS1733E, DAN, DAND1, NB, and NO3, is identified by NCBI Gene ID: 4681. The protein sequence of NCBI Gene ID: 4681 is incorporated herein by reference.

Bone morphogenetic proteins (BMPs) are a group of growth factors originally identified by their ability to induce the formation of bone and cartilage, and now considered to constitute a group of pivotal morphogenetic signals, orchestrating tissue architecture throughout the body. Human BMP-2, also known as BDA2, BMP2A, SSFSC, and SSFSC1, is identified by NCBI Gene ID: 650. The protein sequence of NCBI Gene ID: 650 is incorporated herein by reference. Human BMP-4, also known as BMP2B, BMP2B1, MCOPS6, OFC11, and ZYME, is identified by NCBI Gene ID: 652. The protein sequence of NCBI Gene ID: 652 is incorporated herein by reference. Human BMP-7, also known as OP-1, is identified by NCBI Gene ID: 655. The protein sequence of NCBI Gene ID: 655 is incorporated herein by reference.

As used herein, the term "antibody" has its broadest art-recognized meaning, and therefore includes all known formats. The term specifically includes, without limitation, polyclonal antibodies, monoclonal antibodies, monospecific antibodies, multispecific antibodies (including bispecific antibodies), chimeric antibodies, humanized and fully human antibodies. Antibodies that include heavy chain constant region domains can be of any class, including IgG, IgE, IgM, IgD, and IgA and any subclass, including IgG1, IgG2, IgG3, IgG4, IgA1, and IgA2. "Antigen binding fragments" of antibodies are antibody fragments (and/or polypeptides that comprise antibody fragments) that retain the binding characteristics (e.g., specificity, monovalent affinity or bivalent avidity) of the antibody from which derived, and has its broadest art-recognized meaning. The term includes, without limitation, Fab, Fab', F(ab')$_2$, Fv, scFv, (scFv)$_2$, single domain antibody (including camelid VHH and shark VNAR formats), and multispecific antibodies formed from antibody fragments, including without limitation F(ab)2, and diabody.

As used herein, "chronic kidney disease" (CKD) has the meaning ascribed in the National Kidney Foundation KDOQI guidelines, and stages of CKD are defined as provided in the NKF KDOQI guidelines. "End stage kidney disease" (ESKD) and "end stage renal disease" (ESRD) are used interchangeably herein and have the meaning ascribed in the National Kidney foundation KDOQI guidelines.

In this disclosure, "comprises," "comprising," "containing," "having," "includes," "including", and linguistic variants thereof have the meaning ascribed to them in U.S. Patent law, permitting the presence of additional components beyond those explicitly recited.

Unless specifically stated or apparent from context, as used herein the term "or" is understood to be inclusive.

Unless specifically stated or apparent from context, as used herein, the terms "a", "an", and "the" are understood to be singular or plural.

As used herein, "conservative amino acid substitutions" are those substitutions in which the original and substituted amino acids have similar biochemical properties, or their biochemical effects are similarly maintained across substitutions, as set forth in Table 45.

5.2. Summary of Experimental Results

As detailed in the experimental examples in this disclosure, we have discovered that NBL1 is directly toxic to renal cells, including podocytes and tubular cells. The toxic effect is not mediated through inhibition of renal BMP proteins; we show that BMPs are not expressed in and are not secreted by kidney cells. Moreover, we have discovered that NBL1 is also not expressed in kidney cells, but is expressed in circulating immune cells. Neutralizing NBL1 with an antagonist prevents toxicity. Finally, we demonstrate that NBL1 is elevated in Type 1 Diabetes and Type 2 Diabetes.

5.3. Methods of Delaying Onset or Progression of Kidney Damage

Accordingly, in a first aspect, methods are presented for delaying onset or progression of kidney damage in a subject who has, or is at risk for, type 1 diabetes or type 2 diabetes or who has or is at risk for developing a glomerular disease. The method comprises administering to the subject an effective amount of an agent capable of inhibiting NBL1 activity, and in particular, inhibiting NBL1-mediated toxicity of human podocytes.

In various embodiments, the method delays onset or progression of damage to one or more of renal blood vessels, podocytes, renal tubular cells, or glomerular or tubular basement membrane. In some embodiments, the method delays onset or progression of thickening of glomerular and tubular basement membrane, increase in mesangial matrix, Kimmelstiel-Wilson nodules, microaneurysms, exudative or hyalinosis lesions, capsular drop or afferent and efferent arteriolar hyalinosis.

In some embodiments, the subject has type 1 diabetes. In some embodiments, the subject has type 2 diabetes. In some embodiments, the subject is pre-diabetic. In some embodiments, the subject is not prediabetic as measured by hemoglobin A1c levels or blood glucose levels but is at risk for type 1 diabetes or type 2 diabetes and has elevated NBL1 plasma levels.

In some embodiments, the subject has a glomerular disease. In certain embodiments, the subject with glomerular disease does not have type 1 diabetes or type 2 diabetes. In certain embodiments, the glomerular disease is selected from the group consisting of focal segmental glomeruloscle-rosis (FSGS), chronic glomerulopathies, hereditary nephri-tis, and minimal change disease.

In some embodiments, the subject has pre-treatment plasma NBL1 levels at least 10%, 20%, 30%, 40%, 50%, 60%, 70%, 80%, 90% or 100% higher than normal subjects who do not have type 1 or type 2 diabetes or prediabetes. In some embodiments, the subjects to be treated have NBL1 plasma levels at least 2-fold, 3-fold, 4-fold, 5-fold, 6-fold, 7-fold, 8-fold, 9-fold, or 10-fold higher than normal subjects who do not have type 1 or type 2 diabetes or prediabetes.

In some embodiments, the method effectively reduces the availability of circulating free NBL1 in subjects having type 1 or type 2 diabetes, or who are prediabetic, or who are at risk for type 1 diabetes or type 2 diabetes, and have elevated NBL1 plasma levels, as compared to normal subjects who do not have type 1 or type 2 diabetes or prediabetes. In some embodiments, the method effectively reduces the availabil-ity of circulating free NBL1 in subjects who have a glom-erular disease. In certain embodiments, the method effec-tively reduces the availability of circulating free NBL1 in subjects who have a glomerular disease selected from the group consisting of focal segmental glomerulosclerosis (FSGS), chronic glomerulopathies, hereditary nephritis, and minimal change disease.

In some embodiments, the agent capable of inhibiting NBL1 activity is capable of binding to NBL1. In some embodiments, the binding occurs in the N-terminus of NBL1. In some embodiments, the binding occurs in the functional DAN domain of NBL1. In some embodiments, the binding occurs in the C-terminus of NBL1. In some embodiments, the binding is noncovalent. In some embodi-ments, the binding is covalent. In certain covalent embodi-ments, the inhibitor binds to NBL1 via disulfide bonds within the DAN domain.

In some embodiments, the agent capable of inhibiting NBL1 activity is capable of inhibiting dimerization of NBL1.

In some embodiments, the agent capable of inhibiting NBL1 activity is a dimerization inhibitor that prevents the formation of stabilizing hydrogen bonds between two NBL1 monomers. In some embodiments, the dimerization inhibitor disrupts at least one of the three disulfide bonds that form a ring-like structure known as cysteine-knot motif within each monomer, or the disulfide bond linking F1 to F2, where F1 and F2 are the first loop from the N terminus, finger 1, and the third loop from the N terminus, finger 2, respectively.

5.3.1. Soluble BMP Inhibitors

In some embodiments, the agent capable of inhibiting NBL1 activity comprises a bone morphogenetic protein (BMP) or soluble NBL1-binding fragment thereof. In some embodiments, the BMP is BMP-2 or a soluble NBL1-binding fragment thereof. In some embodiments, the BMP is BMP-4 or a soluble NBL1-binding fragment thereof. In some embodiments, the BMP is BMP-7 or a soluble NBL1-binding fragment thereof. In currently preferred embodi-ments, the BMP is a human BMP or soluble NBL1-binding fragment thereof.

In some embodiments, the agent capable of inhibiting NBL1 further comprises a moiety that extends serum half-life.

In some embodiments, the moiety that extends serum half-life is provided through covalent chemical modification. In some embodiments, the moiety that extends serum half-life is at least one polyethylene glycol (PEG) moiety. In some embodiments, the PEG moiety is permanently attached to the agent. In some embodiments, the PEG moiety is a releasable carrier, provided through covalent chemical modification. In certain embodiments, the agent comprises a PEGylated BMP or soluble NBL1-binding fragment thereof.

In some embodiments, the moiety that extends serum half-life is an antibody Fc domain. In some embodiments, the Fc domain is engineered to optimize the pH-dependent IgG Fc-FcRn interaction. In certain embodiments, the Fc domain is engineered to have the YTE triple mutation (M252Y/S254T/T256E). In certain embodiments, the Fc domain is engineered to have the M428L/N434S mutations. In certain embodiments, the Fc domain is fused in frame to a BMP or soluble NBL1-binding fragment thereof.

In some embodiments, the moiety that extends serum half-life is a serum albumin molecule. In certain embodi-ments, the half-life extending moiety is a human serum albumin molecule fused in frame to a BMP or soluble NBL1-binding fragment thereof.

In some embodiments, the moiety that extends serum half-life is an XTEN protein polymer covalently attached to the agent, as described in Podust et al., *Protein Eng. Des. Sel.* 26 (11): 743-53 (2013), the disclosure of which is incorporated herein by reference in its entirety.

5.3.2. Antibodies and Antigen-Binding Fragments Thereof

In some embodiments, the agent capable of inhibiting NBL1 activity is an antibody capable of binding NBL1, or an NBL1-binding fragment thereof and inhibiting NBL1 activity, and in particular, inhibiting NBL1-mediated toxic-ity of human podocytes. In preferred embodiments, the antibody or antigen-binding antibody fragment is capable of binding human NBL1.

In some embodiments, the antibody or antigen-binding fragment thereof binds to an epitope within the N-terminal domain of NBL1. In some embodiments, the antibody or antigen-binding fragment thereof binds to an epitope within the DAN domain of NBL1. In some embodiments, the antibody or antigen-binding fragment thereof binds to an epitope within the C-terminal domain of NBL1.

In some embodiments, the antibody or antigen-binding fragment thereof comprises heavy chain and light chain CDRs selected from Tables 23-44 below, or the heavy chain and light chain CDRs selected from Tables 23-44 below with no more than 10 amino acid deletions, insertions, or con-servative amino acid substitutions (as defined in Table 45), as compared thereto.

TABLE 45

| Conservative amino acid substitutions | |
| --- | --- |
| Class | Amino Acids |
| Aliphatic | Glycine, Alanine, Valine, Leucine, Isoleucine |
| Hydroxyl or sulfur/ selenium containing | Serine, Cysteine, Selenocysteine, Threonine, Methionine |
| Cyclic | Proline |
| Aromatic | Phenylalanine, Tyrosine, Tryptophan |
| Basic | Histidine, Lysine, Arginine |
| Acidic and their amides | Aspartate, Glutamate, Asparagine, Glutamine |

In some embodiments, the amino acid deletions, inser-tions, or conservative substitutions are no more than 8. In some embodiments, the amino acid deletions, insertions, or conservative substitutions are no more than 6. In some embodiments, the amino acid deletions, insertions, or conservative substitutions are no more than 4.

In some embodiments, the antibody or antigen-binding fragment thereof comprises heavy chain V region and light chain V region selected from Tables 1-22 below.

In some embodiments, the antibody or antigen-binding fragment thereof comprises the heavy chain and light chain CDRs selected from Tables 23-44 and with no more than 10 amino acid deletions, insertions, or conservative amino acid substitutions (as defined in Table 45), as compared thereto. In some embodiments, the amino acid deletions, insertions, or conservative substitutions are no more than 8. In some embodiments, the amino acid deletions, insertions, or conservative substitutions are no more than 6. In some embodiments, the amino acid deletions, insertions, or conservative substitutions are no more than 4.

TABLE 1

| Antibody YU1018-E05a | |
| --- | --- |
| VH | EVQLLESGPGLVKPSQTLSLTCTVSGGSISSGGYYWSWIRQHPGK GLEWIGYIYYSGSTYYNPSLKSRVTISVDTSKNQFSLKLSSVTAAD TAVYYCARTNSRITMIADWGQGTLVTVSS |
| VL | QSVLTQPPSVSAAPGQKVTISCSGSSSNIGNNYVSWYQQLPGTAP KLLIYDNNKRPSGIPDRFSGSKSGTSATLGITGLQTGDEADYYCGT WDSSLSAGVFGGGTQLTVL |

TABLE 23

Antibody Y1018-E05a
CDRs

| | Chothia | AbM | Kabat | Contact | IMGT |
| --- | --- | --- | --- | --- | --- |
| heavy chain CDR1 | GGSISSGGY (SEQ ID NO: 1) | GGSISSGGYYWS (SEQ ID NO: 2) | SGGYYWS (SEQ ID NO: 3) | SSGGYYWS (SEQ ID NO: 4) | GGSISSGGYY (SEQ ID NO: 5) |
| heavy chain CDR2 | YYSGS (SEQ ID NO: 6) | YIYYSGSTY (SEQ ID NO: 7) | YIYYSGSTYYNPSL KS (SEQ ID NO: 8) | WIGYIYYSGSTY (SEQ ID NO: 9) | IYYSGST (SEQ ID NO: 10) |
| heavy chain CDR3 | TNSRITMIAD (SEQ ID NO: 11) | TNSRITMIAD (SEQ ID NO: 12) | TNSRITMIAD (SEQ ID NO: 13) | ARTNSRITMIA (SEQ ID NO: 14) | ARTNSRITMIAD (SEQ ID NO: 15) |
| light chain CDR1 | SGSSSNIGNNYVS (SEQ ID NO: 16) | SGSSSNIGNNYVS (SEQ ID NO: 17) | SGSSSNIGNNYVS (SEQ ID NO: 18) | IGNNYVSWY (SEQ ID NO: 19) | SSNIGNNY (SEQ ID NO: 20) |
| light chain CDR2 | DNNKRPS (SEQ ID NO: 21) | DNNKRPS (SEQ ID NO: 22) | DNNKRPS (SEQ ID NO: 23) | LLIYDNNKRP (SEQ ID NO: 24) | DN (SEQ ID NO: 25) |
| light chain CDR3 | GTWDSSLSAGV (SEQ ID NO: 26) | GTWDSSLSAGV (SEQ ID NO: 27) | GTWDSSLSAQV (SEQ ID NO: 28) | CTWDSSLSAG (SEQ ID NO: 29) | GTWDSSLSAGV (SEQ ID NO: 30) |

TABLE 2

| Antibody YU1018-H08 | |
| --- | --- |
| VH | EVQLLESGPGLVKPSQTLSLTCTVSGGSISSGGYYWSWIRQHPGK GLEWIGYIYYSGSTYYNPSLKSRVTISVDTSKNQFSLKLSSVTAAD TAVYYCARTNSRITMIADWGQGTLVTVSS |
| VL | QSVLTQPPSVSAAPGQKVTISCSGSSSNIGNNYVSWYQQLPGTAP KLLTYDNNKRPSGIPDRFSGSKSGTSATLGITGLQTGDEADYYCGT WDSSLSAGHVFGGGTKVTVL |

TABLE 24

Antibody Y1018-H08
CDRs

| | Chothia | AbM | Kabat | Contact | IMGT |
| --- | --- | --- | --- | --- | --- |
| heavy chain CDR1 | GGSISSGGY (SEQ ID NO: 31) | GGSISSGGYYWS (SEQ ID NO: 32) | SGGYYWS (SEQ ID NO: 33) | SSGGYYWS (SEQ ID NO: 34) | GGSISSGGYY 3(SEQ ID NO: 35) |
| heavy chain CDR2 | YYSGS (SEQ ID NO: 36) | YIYYSGSTY (SEQ ID NO: 37) | YIYYSGSTYYNPSLKS (SEQ ID NO: 38) | WIGYIYYSGSTY (SEQ ID NO: 39) | IYYSGST (SEQ ID NO: 40) |
| heavy chain CDR3 | TNSRITMIAD (SEQ ID NO: 41) | TNSRITMIAD (SEQ ID NO: 42) | TNSRITMIAD (SEQ ID NO: 43) | ARTNSRITMIA (SEQ ID NO: 44) | ARINSRITMIAD (SEQ ID NO: 45) |
| light chain CDR1 | SGSSSNIGNNYVS (SEQ ID NO: 46) | SGSSSNIGNNYVS (SEQ ID NO: 47) | SGSSSNIGNNYVS (SEQ ID NO: 48) | IGNNYVSWY (SEQ ID NO: 49) | SSNIGNNY (SEQ ID NO: 50) |
| light chain CDR2 | DNNKRPS (SEQ ID NO: 51) | DNNKRPS (SEQ ID NO: 52) | DNNKRPS (SEQ ID NO: 53) | LLTYDNNKRP (SEQ ID NO: 54) | DN (SEQ ID NO: 55) |

TABLE 24-continued

| Antibody Y1018-H08 CDRs | | | | |
|---|---|---|---|---|
| Chothia | AbM | Kabat | Contact | IMGT |
| light chain CDR3 CTWDSSLSAGHV (SEQ ID NO: 56) | GTWDSSLSAGHV (SEQ ID NO: 57) | GTWDSSLSAGHV (SEQ ID NO: 58) | GTWDSSLSAGH (SEQ ID NO: 59) | GTWDSSLSAGHV (SEQ ID NO: 60) |

TABLE 3

| Antibody YU1018-F06 | |
|---|---|
| VH | QVQLVESGGGLVQPGGSLRLSCAASGFTFSSYAMSWVRQAPGKGL EWVSAISGSGGSTYYADSVKGRFTISRDNSKNTLYLQMNSLRAED TAVYYCAKGSPYYYDSSGYYPLDYWGQGTLVTVSS |
| VL | DVVMTQSPLSLPVTPGEPASISCRSSQSLLHSNGYNYLDWYLQKP GQSPQLLIYLGSNRAPGVPDRFSGSGSGTDFTLKISRVEAEDVGV YYCMQALQTPLTFGPGTKLEIK |

TABLE 25

| Antibody Y1018-F06 CDRs | | | | |
|---|---|---|---|---|
| Chothia | AbM | Kabat | Contact | IMGT |
| heavy chain CDR1 GFTESSY (SEQ ID NO: 61) | GFTFSSYAMS (SEQ ID NO: 62) | SYAMS (SEQ ID NO: 63) | SSYAMS (SEQ ID NO: 64) | GFTFSSYA (SEQ ID NO: 65) |
| heavy chain CDR2 SGSGGS (SEQ ID NO: 66) | AISGSGGSTY (SEQ ID NO: 67) | AISGSGGSTYYADSVKG (SEQ ID NO: 68) | WVSAISGSGGSTY (SEQ ID NO: 69) | ISGSGGST (SEQ ID NO: 70) |
| heavy chain CDR3 GSPYYYDSSGYYPLDY (SEQ ID NO: 71) | GSPYYYDSSGYYPLDY (SEQ ID NO: 72) | GSPYYYDSSGYYPLDY (SEQ ID NO: 73) | AKGSPYYYDSSGYYPLD (SEQ ID NO: 74) | AKGSPYYYDSSGYY PLDY (SEQ ID NO: 75) |
| light chain CDR1 RSSQSLLHSNGYNYLD (SEQ ID NO: 76) | RSSQSLLHSNQYNYLD (SEQ ID NO: 77) | RSSQSLLHSNGYNYLD (SEQ ID NO: 78) | LHSNGYNYLDWY (SEQ ID NO: 79) | QSLLHSNGYNY (SEQ ID NO: 80) |
| light chain CDR2 LGSNRAP (SEQ ID NO: 81) | LGSNRAP (SEQ ID NO: 82) | LGSNRAP (SEQ ID NO: 83) | LLIYLGSNRA (SEQ ID NO: 84) | LG (SEQ ID NO: 85) |
| light chain CDR3 MQALQTPLT (SEQ ID NO: 86) | MQALQTPLT (SEQ ID NO: 87) | MQALQTPLT (SEQ ID NO: 88) | MQALQTPL (SEQ ID NO: 89) | MQALQTPLT (SEQ ID NO: 90) |

TABLE 4

| Antibody YU1019-A12 | |
|---|---|
| VH | EVQLLESGPGLVKPSQTLSLTCTVSGGSISSGDYYWSWIRQPPGK GLEWIGYIYYSGSTYYNPSLKSRVTISVDTSKNQFSLKLSSVTAAD TAVYYCARGRRLLLFHWGQGTTVTVSS |

TABLE 4-continued

| Antibody YU1019-A12 | |
|---|---|
| VL | QSVLTQPPSVSAAPGQKVTISCSGSGSSIGNNYVSWYQQVPGTPP KLLIYDNNKRASGIPDRFSGSKSGTSATLGITGLQTGDEADYYCGT WDNSLSAVVFGGGTKLTVL |

TABLE 26

| Antibody YU1019-A12 CDRs | | | | |
|---|---|---|---|---|
| Chothia | AbM | Kabat | Contact | IMGT |
| heavy chain CDR1 GGSISSGDY (SEQ ID NO: 91) | GGSISSGDYYWS (SEQ ID NO: 92) | SGDYYWS (SEQ ID NO: 93) | SSGDYYWS (SEQ ID NO: 94) | GGSISSGDYY (SEQ ID NO: 95) |
| heavy chain CDR2 YYSGS (SEQ ID NO: 96) | YIYYSGSTY (SEQ ID NO: 97) | YIYYSGSTYYNPSLKS (SEQ ID NO: 98) | WIGYIYYSGSTY (SEQ ID NO: 99) | IYYSQST (SEQ ID NO: 100) |
| heavy chain CDR3 GRRLLLFH (SEQ ID NO: 101) | GRRLLLFH (SEQ ID NO: 102) | GRRLLLFH (SEQ ID NO: 103) | ARGRRLLLE (SEQ ID NO: 104) | ARGRRLLLFH (SEQ ID NO: 105) |

TABLE 26-continued

| Antibody YU1019-A12 CDRs | | | | |
|---|---|---|---|---|
| Chothia | AbM | Kabat | Contact | IMGT |
| light chain CDR1 SGSGSSIGNNYVS (SEQ ID NO: 106) | SGSGSSIGNNYVS (SEQ ID NO: 107) | SGSGSSIGNNYVS (SEQ ID NO: 108) | IGNNYVSWY (SEQ ID NO: 109) | GSSIGNNY (SEQ ID NO: 110) |
| light chain CDR2 DNNKRAS (SEQ ID NO: 111) | DNNKRAS SEQ ID NO: 112) | DNNKRAS (SEQ ID NO: 113) | LLIYDNNKRA (SEQ ID NO: 114) | DN (SEQ ID NO: 115) |
| light chain CDR3 GTWDNSLSAVV (SEQ ID NO: 116) | GTWDNSLSAVV (SEQ ID NO: 117) | GTWDNSLSAVV (SEQ ID NO: 118) | GTWDNSLSAV (SEQ ID NO: 119) | GTWDNSLSAVV (SEQ ID NO: 120) |

TABLE 5

| Antibody YU1018-G01 |
|---|
| VH   QVQLVQSGAEVKKPGASVKVSCKASGYTFTSYAMHWVRQAPGQ RLEWMGWINAGNGNTKYSQKFQGRVTITRDTSASTAYMELSSL RSEDTAVYYCARGRELLTFDYWGQGTLVTVSS |
| VL   DVVMTQSPLSLPVTPGEPASISCRSSQSLLHSNGYNYLDWYLQKP GQSPQLLIYLGSNRASGVPDRFSGSGSGTDFTLKISRVEAEDVGVY YCMQALQTPLTFGGGTKVEIK |

TABLE 27

| Antibody YU1018-G01 CDRs | | | | |
|---|---|---|---|---|
| Chothia | AbM | Kabat | Contact | IMGT |
| heavy chain CDR1 GYTFTSY (SEQ ID NO: 121) | GYTFTSYAMH (SEQ ID NO: 122) | SYAMH (SEQ ID NO: 123) | TSYAMH (SEQ ID NO: 124) | GYTFTSYA (SEQ ID NO: 125) |
| heavy chain CDR2 NAGNGN (SEQ ID NO: 126) | WINAGNGNTK (SEQ ID NO: 127) | WINAGNGNTKYSQKF QG (SEQ ID NO: 128) | WMGWINAGNGNTK (SEQ ID NO: 129) | INAGNGNT (SEQ ID NO: 130) |
| heavy chain CDR3 GRELLTEDY (SEQ ID NO: 131) | GRELLTEDY (SEQ ID NO: 132) | GRELLIFDY (SEQ ID NO: 133) | ARGRELLTED (SEQ ID NO: 134) | ARGRELLTEDY (SEQ ID NO: 135) |
| light chain CDR1 RSSQSLLHSNGYNYL D (SEQ ID NO: 136) | RSSQSLLHSNGYNYLD (SEQ ID NO: 137) | RSSQSLLHSNGYNYLD (SEQ ID NO: 138) | LHSNGYNYLDWY (SEQ ID NO: 139) | QSLLHSNGYNY (SEQ ID NO: 140) |
| light chain CDR2 LGSNRAS (SEQ ID NO: 141) | LGSNRAS (SEQ ID NO: 142) | LGSNRAS (SEQ ID NO: 143) | LLIYLGSNRA (SEQ ID NO: 144) | LG (SEQ ID NO: 145) |
| light chain CDR3 MQALQTPLI (SEQ ID NO: 146) | MQALQTPLT (SEQ ID NO: 147) | MQALQTPLT (SEQ ID NO: 148) | MQALQTPL (SEQ ID NO: 149) | MQALQTPLT (SEQ ID NO: 150) |

TABLE 6

| Antibody YU1019-E11 |
|---|
| VH   QVQLQESGPGLVKPSQTLSLTCTVSGGSISSGGYYWSWIRQHPGK GLEWIGYIYYSGSTYYNPSLKSRVTISVDTSKNQFSLKLSSVTAAD TAVYYCARDAPLRIGAFDIWGQGTMVTVSS |

TABLE 6-continued

| Antibody YU1019-E11 |
|---|
| VL   QSVLTQPPSVSAAPGQKVTISCSGSSSNIGNNYVSWYQQLPGTAP KLLIYDNNKRPSGIPDRFSGSKSGTSATLGITRLQTGDEADYYCGT WDSSLSAGVFGGGTKLTVL |

TABLE 28

| Antibody YU1019-E11 CDRs | | | | |
|---|---|---|---|---|
| Chothia | AbM | Kabat | Contact | IMGT |
| heavy chain CDR1 GGSISSGGY (SEQ ID NO: 151) | GGSISSGGYYWS (SEQ ID NO: 152) | SGGYYWS (SEQ ID NO: 153) | SSGGYYWS (SEQ ID NO: 154) | GGSISSGGYY (SEQ ID NO: 155) |

TABLE 28-continued

Antibody YU1019-E11
CDRs

|  | Chothia | AbM | Kabat | Contact | IMGT |
|---|---|---|---|---|---|
| heavy chain CDR2 | YYSGS (SEQ ID NO: 156) | YIYYSGSTY (SEQ ID NO: 157) | YIYYSGSTYYNPSLKS (SEQ ID NO: 158) | WIGYIYYSGSTY (SEQ ID NO: 159) | IYYSGST (SEQ ID NO: 160) |
| heavy chain CDR3 | DAPLRIGAFDI (SEQ ID NO: 161) | DAPLRIGAFDI (SEQ ID NO: 162) | DAPLRIG AFDI (SEQ ID NO: 163) | ARDAPLRIGAFD (SEQ ID NO: 164) | ARDAPLRIGAFDI (SEQ ID NO: 165) |
| light chain CDR1 | SGSSSNIGNNYVS (SEQ ID NO: 166) | SGSSSNIGNNYVS (SEQ ID NO: 167) | SGSSSNIGNNYVS (SEQ ID NO: 168) | IGNNYVSWY (SEQ ID NO: 169) | SSNIGNNY (SEQ ID NO: 170) |
| light chain CDR2 | DNNKRPS (SEQ ID NO: 171) | DNNKRPS (SEQ ID NO: 172) | DNNKRPS (SEQ ID NO: 173) | LLIYDNNKRP (SEQ ID NO: 174) | DN (SEQ ID NO: 175) |
| light chain CDR3 | CTWDSSLSAGV (SEQ ID NO: 176) | GTWDSSLSAGV (SEQ ID NO: 177) | GTWDSSLSAGV (SEQ ID NO: 178) | GTWDSSLSAG (SEQ ID NO: 179) | GTWDSSLSAGV (SEQ ID NO: 180) |

TABLE 7

Antibody YU1019-B06

| VH | EVQLLESGGGVVQPGRSLRLSCAASGFTFSSYAMHWVRQAPGKG LEWVAVISYDGSNKYYADSVKGRFTISRDNSKNTLYLQMNSLRA EDTAVYYCASPVLRYFDWLPNYWGQGTLVTVSS |
|---|---|
| VL | DVVMTQSPLSLPVTLGQPASISCRSSQSLVYSDGNTYLNWFQQRP GQSPRRLIYKVSNRDSGVPDRFSGSGSGTDFTLKISRVEAEDVGV YYCMQGTHWPPAFGPGTKVDIK |

TABLE 29

Antibody YU1019-B06
CDRs

|  | Chothia | AbM | Kabat | Contact | IMGT |
|---|---|---|---|---|---|
| heavy chain CDR1 | GFTFSSY (SEQ ID NO: 181) | GFTFSSYAMH (SEQ ID NO: 182) | SYAMH (SEQ ID NO: 183) | SSYAMH (SEQ ID NO: 184) | GFTFSSYA (SEQ ID NO: 185) |
| heavy chain CDR2 | SYDGSN (SEQ ID NO: 186) | VISYDGSNKY (SEQ ID NO: 187) | VISYDGSNKYYADSVK G (SEQ ID NO: 188) | WVAVISYDQSNKY (SEQ ID NO: 189) | ISYDGSNK (SEQ ID NO: 190) |
| heavy chain CDR3 | PVLRYEDWLPNY (SEQ ID NO: 191) | PVLRYFDWLPNY (SEQ ID NO: 192) | PVLRYFDWLPNY (SEQ ID NO: 193) | ASPVLRYFDWLPN (SEQ ID NO: 194) | ASPVLRYEDWLPNY (SEQ ID NO: 195) |
| light chain CDR1 | RSSQSLVYSDGNTYL N (SEQ ID NO: 196) | RSSQSLVYSDGNTY LN (SEQ ID NO: 197) | RSSQSLVYSDGNTYLN (SEQ ID NO: 198) | VYSDGNTYLNWF (SEQ ID NO: 199) | QSLVYSDGNTY (SEQ ID NO: 200) |
| light chain CDR2 | KVSNRDS (SEQ ID NO: 201) | KVSNRDS (SEQ ID NO: 202) | KVSNRDS (SEQ ID NO: 203) | RLIYKVSNRD (SEQ ID NO: 204) | KV (SEQ ID NO: 205) |
| light chain CDR3 | MQGTHWPPA (SEQ ID NO: 206) | MQGTHWPPA (SEQ ID NO: 207) | MQGTHWPPA (SEQ ID NO: 208) | MQGTHWPP (SEQ ID NO: 209) | MQGTHWPPA (SEQ ID NO: 210) |

TABLE 8

Antibody YU1018-D12

| VH | EVQLVQSGAEVKKPGASVKVSCKASGYTFTSYGISWVRQAPGQGL EWMGWISAYNGNTNYAQKLQGRVTMTTDTSTSTAYMELRSLRSDD TAVYYCARDVGYSYGIFDYWGQGTLVTVSS |
|---|---|
| VL | DVVMTQSPLSLPATPGEPASISCRSSQSLLHSNGYNYLDWYLQKP GQSPQLLIYLGSNRASGVPDRFSGSGSGTDFTLKISRVEAEDVGV YYCMQALQTPYTFGQGTKVEIK |

TABLE 30

Antibody YU1018-D12
CDRs

| | Chothia | AbM | Kabat | Contact | IMGT |
|---|---|---|---|---|---|
| heavy chain CDR1 | GYTFTSY (SEQ ID NO: 211) | GYTFTSYGIS (SEQ ID NO: 212) | SYGIS (SEQ ID NO: 213) | TSYGIS (SEQ ID NO: 214) | GYTFTSYG (SEQ ID NO: 215) |
| heavy chain CDR2 | SAYNGN (SEQ ID NO: 216) | WISAYNGNTN (SEQ ID NO: 217) | WISAYNGNTNYAQKLQG (SEQ ID NO: 218) | WMGWISAYNGNTN (SEQ ID NO: 219) | ISAYNGNT (SEQ ID NO: 220) |
| heavy chain CDR3 | DVGYSYGIFDY (SEQ ID NO: 221) | DVGYSYGIFDY (SEQ ID NO: 222) | DVQYSYGIFDY (SEQ ID NO: 223) | ARDVGYSYGIFD (SEQ ID NO: 224) | ARDVGYSYGIFDY (SEQ ID NO: 225) |
| light chain CDR1 | RSSQSLLHSNGYNYLD (SEQ ID NO: 226) | RSSQSLLHSNGYNYLD (SEQ ID NO: 227) | RSSQSLLHSNGYNYLD (SEQ ID NO: 228) | LHSNGYNYLDWY (SEQ ID NO: 229) | QSLLHSNGYNY (SEQ ID NO: 230) |
| light chain CDR2 | LGSNRAS (SEQ ID NO: 231) | LGSNRAS (SEQ ID NO: 232) | LQSNRAS (SEQ ID NO: 233) | LLIYLGSNRA (SEQ ID NO: 234) | LG (SEQ ID NO: 235) |
| light chain CDR3 | MQALQTPYT (SEQ ID NO: 236) | MQALQTPYT (SEQ ID NO: 237) | MQALQTPYT (SEQ ID NO: 238) | MQALQTPY (SEQ ID NO: 239) | MQALQTPYT (SEQ ID NO: 240) |

TABLE 9

Antibody YU1019-H01

| VH | EVQLVQSGAEVKKPGASVKVSCKASGYTFTSYYMHWVRQAPGQGL EWMGIINPSGGSTSYAQKFQGRVTMTRDTSTSTVYMELSSLRSED TAVYYCARAPGKFPLDYWGQGTLVTVSS |
|---|---|
| VL | DVVMTQSPLSLPVTPGEPASISCRSSQSLLHSNGYNYLDWYLQKP GQSPQLLIYLGSNRASGVPDRFSGSGSGTDFTLKISRVEAEDVGV YYCMQALQTPRTFGGGTKVEIK |

TABLE 31

Antibody YU1019-H01
CDRs

| | Chothia | AbM | Kabat | Contact | IMGT |
|---|---|---|---|---|---|
| heavy chain CDR1 | GYTFTSY (SEQ ID NO: 241) | GYTFTSYYMH (SEQ ID NO: 242) | SYYMH (SEQ ID NO: 243) | TSYYMH (SEQ ID NO: 244) | GYTFTSYY (SEQ ID NO: 245) |
| heavy chain CDR2 | NPSGGS (SEQ ID NO: 246) | IINPSGGSTS (SEQ ID NO: 247) | IINPSGGSTSYAQKFQG (SEQ ID NO: 248) | WMGIINPSGGSTS (SEQ ID NO: 249) | INPSGGST (SEQ ID NO: 250) |
| heavy chain CDR3 | APGKFPLDY (SEQ ID NO: 251) | APGKFPLDY (SEQ ID NO: 252) | APGKFPLDY (SEQ ID NO: 253) | ARAPGKFPLD (SEQ ID NO: 254) | ARAPGKFPLDY (SEQ ID NO: 255) |
| light chain CDR1 | RSSQSLLHSNGYNYLD (SEQ ID NO: 256) | RSSQSLLHSNGYNYLD (SEQ ID NO: 257) | RSSQSLLHSNGYNYLD (SEQ ID NO: 258) | LHSNGYNYLDWY (SEQ ID NO: 259) | QSLLHSNGYNY (SEQ ID NO: 260) |
| light chain CDR2 | LGSNRAS (SEQ ID NO: 261) | LGSNRAS (SEQ ID NO: 262) | LGSNRAS (SEQ ID NO: 263) | LLIYLGSNRA (SEQ ID NO: 264) | LG (SEQ ID NO: 265) |
| light chain CDR3 | MQALQTPRT (SEQ ID NO: 266) | MQALQTPRT (SEQ ID NO: 267) | MQALQTPRT (SEQ ID NO: 268) | MQALQTPR (SEQ ID NO: 269) | MQALQTPRT (SEQ ID NO: 270) |

TABLE 10

Antibody YU1018-C11

| VH | QVQLVQSGGGLVQPGGSLRLSCAASGFTFSSYAMSWVRQAPGKGL EWVSAISGSGGSTYYADSVKGRFTISRDNSKNTLYLQMNSLRAED TAVYYCARGGFWGSYRYWSAAFDIWGQGTMVTVSS |
|---|---|
| VL | DIVMTQSPLSLPVTPGEPASISCRSSQSLLHSNGYNYLDWYLQKP GQSPQLLIYLGSNRASGVPDRFSGSGSGTDFTLKISRVEAEDVGV YYCMQALQTPPTFGGGTKVEIK |

TABLE 32

Antibody YU1018-C11
CDRs

|  | Chothia | AbM | Kabat | Contact | IMGT |
|---|---|---|---|---|---|
| heavy chain CDR1 | GFTFSSY (SEQ ID NO: 271) | GFTFSSYAMS (SEQ ID NO: 272) | SYAMS (SEQ ID NO: 273) | SSYAMS (SEQ ID NO: 274) | GFTFSSYA (SEQ ID NO: 275) |
| heavy chain CDR2 | SGSGGS (SEQ ID NO: 276) | AISGSGGSTY (SEQ ID NO: 277) | AISGSGGSTYYADSVK G (SEQ ID NO: 278) | WVSAISGSGGSTY (SEQ ID NO: 279) | ISGSGGST (SEQ ID NO: 280) |
| heavy chain CDR3 | GGFWGSYRYWSAAFD I (SEQ ID NO: 281) | GGFWGSYRYWSAAFDI (SEQ ID NO: 282) | GGFWGSYRYWSAAFD I (SEQ ID NO: 283) | ARGGFWGSYRYWSA AFD (SEQ ID NO: 284) | ARGGFWGSYRYWSAAF DI (SEQ ID NO: 285) |
| light chain CDR1 | RSSQSLLHSNGYNYLD (SEQ ID NO: 286) | RSSQSLLHSNGYNYLD (SEQ ID NO: 287) | RSSQSLLHSNGYNYLD (SEQ ID NO: 288) | LHSNGYNYLDWY (SEQ ID NO: 289) | QSLLHSNGYNY (SEQ ID NO: 290) |
| light chain CDR2 | LGSNRAS (SEQ ID NO: 291) | LGSNRAS (SEQ ID NO: 292) | LGSNRAS (SEQ ID NO: 293) | LLIYLGSNRA (SEQ ID NO: 294) | LG (SEQ ID NO: 295) |
| light chain CDR3 | MQALQTPPT (SEQ ID NO: 296) | MQALQTPPT (SEQ ID NO: 297) | MQALQTPPT (SEQ ID NO: 298) | MQALQTPP (SEQ ID NO: 299) | MQALQTPPT (SEQ ID NO: 300) |

TABLE 11

Antibody YU1019-E05b

| VH | EVQLVESGAEVKKPGASVKVSCKASGYTFTSYGITWVRQAPGQGL EWMGWISAYNGNTNYAQKLQGRVTMTTDTSTSTAYMELRSLRSDD TAVYYCARHHPTGGSATIVFDYWGQGTLVTVSS |
|---|---|
| VL | DVVMTQSPLSLPVTPGEPASISCRSSQSLLHSNGYNYLDWYLQKP GQSPQLLIYLGSNRASGVPDRFRGSGSGTDFTLKISRVEAEDVGV YYCMQALQTPGFGQGTKVEIK |

TABLE 12

Antibody YU1019-F10

| VH | QVQLVQSGAEVKKPGASVKVSCKASGYTFTSYYMHWVRQAPGQGL EWMGIINPSGGSTSYAQKFQGRVTMTRDTSTSTVYMELSSLRSED TAVYYCARAPGKFPLDYWGQGTLVTVSS |
|---|---|
| VL | DVVMTQSPLSLPVTPGEPASISCRSSQSLLHSNGYNYLDWYLQKP GQSPQLLIYLGSNRASGVPDRFRGSGSGTDFTLKISRVEAEDVGV YYCMQALQTPGFGQGTKVEIK |

TABLE 33

Antibody YU1019-E05b
CDRs

|  | Chothia | AbM | Kabat | Contact | IMGT |
|---|---|---|---|---|---|
| heavy chain CDR1 | GYTFTSY (SEQ ID NO: 301) | GYTFTSYGIT (SEQ ID NO: 302) | SYGIT (SEQ ID NO: 303) | TSYGIT (SEQ ID NO: 304) | GYTFTSYG (SEQ ID NO: 305) |
| heavy chain CDR2 | SAYNGN (SEQ ID NO: 306) | WISAYNGNTN (SEQ ID NO: 307) | WISAYNGNTNYAQKL QG (SEQ ID NO: 308) | WMGWISAYNGNTN (SEQ ID NO: 309) | ISAYNGNT (SEQ ID NO: 310) |
| heavy chain CDR3 | HHPTGGSATIVFDY (SEQ ID NO: 311) | HHPTGGSATIVFDY (SEQ ID NO: 312) | HHPTGGSATIVFDY (SEQ ID NO: 313) | ARHHPIGGSATIVFD (SEQ ID NO: 314) | ARHHPTGGSATIVFDY (SEQ ID NO: 315) |
| light chain CDR1 | RSSQSLLHSNGYNYL D (SEQ ID NO: 316) | RSSQSLLHSNGYNYLD (SEQ ID NO: 317) | RSSQSLLHSNGYNYLD (SEQ ID NO: 318) | LHSNGYNYLDWY (SEQ ID NO: 319) | QSLLHSNGYNY (SEQ ID NO: 320) |
| light chain CDR2 | LGSNRAS (SEQ ID NO: 321) | LGSNRAS (SEQ ID NO: 322) | LGSNRAS (SEQ ID NO: 323) | LLIYLGSNRA (SEQ ID NO: 324) | LG (SEQ ID NO: 325) |
| light chain CDR3 | MQALQTPLT (SEQ ID NO: 326) | MQALQTPLT (SEQ ID NO: 327) | MQALQTPLT (SEQ ID NO: 328) | MQALQTPL (SEQ ID NO: 329) | MQALQTPLT (SEQ ID NO: 330) |

TABLE 34

| | Antibody YU1019-F10 CDRs | | | | |
|---|---|---|---|---|---|
| | Chothia | AbM | Kabat | Contact | IMGT |
| heavy chain CDR1 | GYTFTSY (SEQ ID NO: 331) | GYTFTSYYMH (SEQ ID NO: 332) | SYYMH (SEQ ID NO: 333) | TSYYMH (SEQ ID NO: 334) | GYTFTSYY (SEQ ID NO: 335) |
| heavy chain CDR2 | NPSGGS (SEQ ID NO: 336) | IINPSGGSTS (SEQ ID NO: 337) | IINPSGGSTSYAQKFQG (SEQ ID NO: 338) | WMGIINPSGGSTS (SEQ ID NO: 339) | INPSGGST (SEQ ID NO: 340) |
| heavy chain CDR3 | APGKFPLDY (SEQ ID NO: 341) | APGKFPLDY (SEQ ID NO: 342) | APGKFPLDY (SEQ ID NO: 343) | ARAPGKFPLD (SEQ ID NO: 344) | ARAPGKFPLDY (SEQ ID NO: 345) |
| light chain CDR1 | RSSQSLLHSNGYNYL D (SEQ ID NO: 346) | RSSQSLLHSNGYNYLD (SEQ ID NO: 347) | RSSQSLLHSNGYNYLD (SEQ ID NO: 348) | LHSNGYNYLDWY (SEQ ID NO: 349) | QSLLHSNGYNY (SEQ ID NO: 350) |
| light chain CDR2 | LGSNRAS (SEQ ID NO: 351) | LGSNRAS (SEQ ID NO: 352) | LGSNRAS (SEQ ID NO: 353) | LLIYLGSNRA (SEQ ID NO: 354) | LG (SEQ ID NO: 355) |
| light chain CDR3 | MQALQTPG (SEQ ID NO: 356) | MQALQTPG (SEQ ID NO: 357) | MQALQTPG (SEQ ID NO: 358) | MQALQTP (SEQ ID NO: 359) | MQALQTPG (SEQ ID NO: 360) |

TABLE 13

| | Antibody YU1018-G10 |
|---|---|
| VH | EVQLVQSGAEVKKPGASVKVSCKASGYTFTSYYMHWVRQAPGQGL EWMGIINPSGGSTSYAQKFQGRVTMTRDTSTSTVYMELSSLRSED TAVYYCARAPGKFPLDYWGQGTLVTVSS |
| VL | DVVMTQSPLSLPVTPGEPASISCRSSQSLLHSNGYNYLDWYLQKP GQSPQLLIYLGSNRASGVPDRFSGSGSGTDFTLKISRVEAEDVGV YYCMQALQTPWTFGQGTKLEIK |

TABLE 35

| | Antibody YU1018-G10 CDRs | | | | |
|---|---|---|---|---|---|
| | Chothia | AbM | Kabat | Contact | IMGT |
| heavy chain CDR1 | GYTFTSY (SEQ ID NO: 361) | GYTFTSYYMH (SEQ ID NO: 362) | SYYMH (SEQ ID NO: 363) | TSYYMH (SEQ ID NO: 364) | GYTFTSYY (SEQ ID NO: 365) |
| heavy chain CDR2 | NPSGGS (SEQ ID NO: 366) | IINPSGGSTS (SEQ ID NO: 367) | IINPSGGSTSYAQKFQG (SEQ ID NO: 368) | WMGIINPSGGSTS (SEQ ID NO: 369) | INPSGGST (SEQ ID NO: 370) |
| heavy chain CDR3 | APGKFPLDY (SEQ ID NO: 371) | APGKFPLDY (SEQ ID NO: 372) | APGKFPLDY (SEQ ID NO: 373) | ARAPGKFPLD (SEQ ID NO: 374) | ARAPGKFPLDY (SEQ ID NO: 375) |
| light chain CDR1 | RSSQSLLHSNGYNYLD (SEQ ID NO: 376) | RSSQSLLHSNGYNYLD (SEQ ID NO: 377) | RSSQSLLHSNGYNYLD (SEQ ID NO: 378) | LHSNGYNYLDWY (SEQ ID NO: 379) | QSLLHSNGYNY (SEQ ID NO: 380) |
| light chain CDR2 | LGSNRAS (SEQ ID NO: 381) | LGSNRAS (SEQ ID NO: 382) | LGSNRAS (SEQ ID NO: 383) | LLIYLGSNRA (SEQ ID NO: 384) | LG (SEQ ID NO: 385) |
| light chain CDR3 | MQALQTPWT (SEQ ID NO: 386) | MQALQTPWT (SEQ ID NO: 387) | MQALQTPWT (SEQ ID NO: 388) | MQALQTPW (SEQ ID NO: 389) | MQALQTPWT (SEQ ID NO: 390) |

TABLE 14

| | Antibody YU1018-E04 |
|---|---|
| VH | QVQLVQSGAEVKKPGESLKISCKGSGYSFTSYWIGWVRQMPGKGL EWMGIIYPGDSDTRYSPSFQGQVTISADKSISTAYLQWSSLKASD TAMYYCARAIVGATSGYWFDPWGQGTLVTVSS |
| VL | DIVMTQSPLSLPVTPGEPASISCRSSQSLLHSNGYNYLDWYLQKP GQSPQLLIYLGSNRASGVPDRFSGSGSGTDFTLKISRVEAEDVGV YYCMQALQTPLTFGGGTKVEIK |

TABLE 36

Antibody YU1018-E04
CDRs

| | Chothia | AbM | Kabat | Contact | IMGT |
|---|---|---|---|---|---|
| heavy chain CDR1 | GYSFTSY (SEQ ID NO: 391) | GYSFTSYWIG (SEQ ID NO: 392) | SYWIG (SEQ ID NO: 393) | TSYWIG (SEQ ID NO: 394) | GYSFTSYW (SEQ ID NO: 395) |
| heavy chain CDR2 | YPGDSD (SEQ ID NO: 396) | IIYPGDSDTR (SEQ ID NO: 397) | IIYPGDSDTRYSPSFQG (SEQ ID NO: 398) | WMGIIYPGDSDTR (SEQ ID NO: 399) | IYPGDSDT (SEQ ID NO: 400) |
| heavy chain CDR3 | AIVGATSGYWFDP (SEQ ID NO: 401) | AIVGATSGYWFDP (SEQ ID NO: 402) | AIVGATSGYWFDP (SEQ ID NO: 403) | ARAIVGATSGYWFD (SEQ ID NO: 404) | ARAIVGATSGYWFDP (SEQ ID NO: 405) |
| light chain CDR1 | RSSQSLLHSNGYNYLD (SEQ ID NO: 406) | RSSQSLLHSNGYNYLD (SEQ ID NO: 407) | RSSQSLLHSNGYNYLD (SEQ ID NO: 408) | LHSNGYNYLDWY (SEQ ID NO: 409) | QSLLHSNGYNY (SEQ ID NO: 410) |
| light chain CDR2 | LGSNRAS (SEQ ID NO: 411) | LGSNRAS (SEQ ID NO: 412) | LGSNRAS (SEQ ID NO: 413) | LLIYLGSNRA (SEQ ID NO: 414) | LG (SEQ ID NO: 415) |
| light chain CDR3 | MQALQTPLT (SEQ ID NO: 416) | MQALQTPLT (SEQ ID NO: 417) | MQALQTPLT (SEQ ID NO: 418) | MQALQTPL (SEQ ID NO: 419) | MQALQTPLT (SEQ ID NO: 420) |

TABLE 15

Antibody YU1018-E07

| VH | EVQLLESGGGVVQPGRSLRLSCAASGFTFSSYAMHWVRQAPGKGLEWVAVISYDGSNKYYADSVKGRFTISRDNSKNTLYLQMNSLRAEDTAVYYCASPVLRYFDWLPNYWGQGTTVTVSS |
|---|---|

TABLE 15-continued

Antibody YU1018-E07

| VL | DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPYSFGQGTKVEIK |
|---|---|

TABLE 37

Antibody YU1018-E07
CDRs

| | Chothia | AbM | Kabat | Contact | IMGT |
|---|---|---|---|---|---|
| heavy chain CDR1 | GFTFSSY (SEQ ID NO: 421) | GFTFSSYAMH (SEQ ID NO: 422) | SYAMH (SEQ ID NO: 423) | SSYAMH (SEQ ID NO: 424) | GFTFSSYA (SEQ ID NO: 425) |
| heavy chain CDR2 | SYDGSN (SEQ ID NO: 426) | VISYDGSNKY (SEQ ID NO: 427) | VISYDGSNKYYADSVKG (SEQ ID NO: 428) | WVAVISYDGSNKY (SEQ ID NO: 429) | ISYDGSNK (SEQ ID NO: 430) |
| heavy chain CDR3 | PVLRYFDWLPNY (SEQ ID NO: 431) | PVLRYFDWLPNY (SEQ ID NO: 432) | PVLRYFDWLPNY (SEQ ID NO: 433) | ASPVLRYFDWLPN (SEQ ID NO: 434) | ASPVLRYFDWLPNY (SEQ ID NO: 435) |
| light chain CDR1 | RSSQSLVYSDGNTYLN (SEQ ID NO: 436) | RSSQSLVYSDGNTYLN (SEQ ID NO: 437) | RSSQSLVYSDGNTYLN (SEQ ID NO: 438) | VYSDGNTYLNWF (SEQ ID NO: 439) | QSLVYSDGNTY (SEQ ID NO: 440) |
| light chain CDR2 | KVSNRDS (SEQ ID NO: 441) | KVSNRDS (SEQ ID NO: 442) | KVSNRDS (SEQ ID NO: 443) | RLIYKVSNRD (SEQ ID NO: 444) | KV (SEQ ID NO: 445) |
| light chain CDR3 | MQGTHWPYS (SEQ ID NO: 446) | MQGTHWPYS (SEQ ID NO: 447) | MQGTHWPYS (SEQ ID NO: 448) | MQGTHWPY (SEQ ID NO: 449) | MQGTHWPYS (SEQ ID NO: 450) |

TABLE 16

Antibody YU1018-E12

| VH | QVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARGHGATAFDIWGQGTMVTVSS |
|---|---|
| VL | DVVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPPTFGPGTKLEIK |

TABLE 38

Antibody YU1018-E12
CDRs

| | Chothia | AbM | Kabat | Contact | IMGT |
|---|---|---|---|---|---|
| heavy chain CDR1 | GYSFTSY (SEQ ID NO: 451) | GYSFTSYWIG (SEQ ID NO: 452) | SYWIG (SEQ ID NO: 453) | TSYWIG (SEQ ID NO: 454) | GYSFTSYW (SEQ ID NO: 455) |
| heavy chain CDR2 | YPGDSD (SEQ ID NO: 456) | IIYPGDSDTR (SEQ ID NO: 457) | IIYPGDSDTRYSPSFQG (SEQ ID NO: 458) | WMGIIYPGDSDTR (SEQ ID NO: 459) | IYPGDSDT (SEQ ID NO: 460) |
| heavy chain CDR3 | GHGATAFDI (SEQ ID NO: 461) | GHGATAFDI (SEQ ID NO: 462) | GHGATAFDI (SEQ ID NO: 463) | ARGHGATAFD (SEQ ID NO: 464) | ARGHGATAFDI (SEQ ID NO: 465) |
| light chain CDR1 | RSSQSLLHSNGYNYLD (SEQ ID NO: 466) | RSSQSLLHSNGYNYLD (SEQ ID NO: 467) | RSSQSLLHSNGYNYLD (SEQ ID NO: 468) | LHSNGYNYLDWY (SEQ ID NO: 469) | QSLLHSNGYNY (SEQ ID NO: 470) |
| light chain CDR2 | LGSNRAS (SEQ ID NO: 471) | LGSNRAS (SEQ ID NO: 472) | LGSNRAS (SEQ ID NO: 473) | LLIYLGSNRA (SEQ ID NO: 474) | LG (SEQ ID NO: 475) |
| light chain CDR3 | MQALQTPPT (SEQ ID NO: 476) | MQALQTPPT (SEQ ID NO: 477) | MQALQTPPT (SEQ ID NO: 478) | MQALQTPP (SEQ ID NO: 479) | MQALQTPPT (SEQ ID NO: 480) |

TABLE 17

Antibody YU1018-D08

| VH | QVQLVQSGAEVKKPGSSVKVSCKASGGTFSSYAISWVRQAPGQGLEWMGGIIPIFGTANYAQKFQGRVTITADKSTSTAYMELSSLR SEDTAVYYCARDRYYDSSGYYLMDPWGQGTLVTVSS |
|---|---|
| VL | DIVMTQSPLSSPVTLGQPASISCRSSQSLVHSDGNTYLSWLQQRPGQPPRLLIYKISNRFSGVPDRFSGSGAGTDFTLKISRVEAED VGVYYCMQATQFPLTFGGGTRLEIK |

TABLE 39

Antibody YU1018-D08
CDRs

| | Chothia | AbM | Kabat | Contact | IMGT |
|---|---|---|---|---|---|
| heavy chain CDR1 | GGTFSSY (SEQ ID NO: 481) | GGTFSSYAIS (SEQ ID NO: 482) | SYAIS (SEQ ID NO: 483) | SSYAIS (SEQ ID NO: 484) | GGTFSSYA (SEQ ID NO: 485) |
| heavy chain CDR2 | IPIFGT (SEQ ID NO: 486) | GIIPIFGTAN (SEQ ID NO: 487) | GIIPIFGTANYAQKFQG (SEQ ID NO: 488) | WMGGIIPIFGTAN (SEQ ID NO: 489) | IIPIFGTA (SEQ ID NO: 490) |
| heavy chain CDR3 | DRYYDSSGYYLMDP (SEQ ID NO: 491) | DRYYDSSGYYLMDP (SEQ ID NO: 492) | DRYYDSSGYYLMDP (SEQ ID NO: 493) | ARDRYYDSSGYYLM D (SEQ ID NO: 494) | ARDRYYDSSGYYLMDP (SEQ ID NO: 495) |
| light chain CDR1 | RSSQSLVHSDGNTYLS (SEQ ID NO: 496) | RSSQSLVHSDGNTYLS (SEQ ID NO: 497) | RSSQSLVHSDGNTYLS (SEQ ID NO: 498) | VHSDGNTYLSWL (SEQ ID NO: 499) | QSLVHSDGNTY (SEQ ID NO: 500) |
| light chain CDR2 | KISNRFS (SEQ ID NO: 501) | KISNRFS (SEQ ID NO: 502) | KISNRFS (SEQ ID NO: 503) | LLIYKISNRE (SEQ ID NO: 504) | KI (SEQ ID NO: 505) |
| light chain CDR3 | MQATQFPLT (SEQ ID NO: 506) | MQATQFPLT (SEQ ID NO: 507) | MQATQFPLT (SEQ ID NO: 508) | MQATQFPL (SEQ ID NO: 509) | MQATQFPLT (SEQ ID NO: 510) |

TABLE 18

| Antibody YU1018-E10 |
| --- |

| VH | QVQLVQSGAEVKKPGASVKVSCKASGYTFTSYYMHWVRQAPGQGLEWMGIINPSGGSTSYAQKFQGRVTMTRDTSTSTVYMELSS LRSEDTAVYYCARAPGKFPLDYWGQGTLVTVSS |
| VL | DVVMTQSPLSLPVTPGEPASISCRSSQSLLKSNGYNYLDWYLQKPGQSPQLLIYLGSNRASGVPDRFSGSGSGTDFSLKIRRVEA EDVGVYYCMQTLQTPYTFGQGTKLEIK |

TABLE 40

| Antibody YU1018-E10 CDRs | | | | | |
| --- | --- | --- | --- | --- | --- |
| | Chothia | AbM | Kabat | Contact | IMGT |
| heavy chain CDR1 | GYTFTSY (SEQ ID NO: 511) | GYTFTSYYMH (SEQ ID NO: 512) | SYYMH (SEQ ID NO: 513) | TSYYMH (SEQ ID NO: 514) | GYTFTSYY (SEQ ID NO: 515) |
| heavy chain CDR2 | NPSGGS (SEQ ID NO: 516) | IINPSGGSTS (SEQ ID NO: 517) | IINPSGGSTSYAQKFQG (SEQ ID NO: 518) | WMGIINPSGGSTS (SEQ ID NO: 519) | INPSGGST (SEQ ID NO: 520) |
| heavy chain CDR3 | APGKFPLDY (SEQ ID NO: 521) | APGKFPLDY (SEQ ID NO: 522) | APGKFPLDY (SEQ ID NO: 523) | ARAPGKFPLD (SEQ ID NO: 524) | ARAPGKFPLDY (SEQ ID NO: 525) |
| light chain CDR1 | RSSQSLLKSNGYNYL D (SEQ ID NO: 526) | RSSQSLLKSNGYNYLD (SEQ ID NO: 527) | RSSQSLLKSNGYNYLD (SEQ ID NO: 528) | LKSNGYNYLDWY (SEQ ID NO: 529) | QSLIKSNGYNY (SEQ ID NO: 530) |
| light chain CDR2 | LGSNRAS (SEQ ID NO: 531) | LGSNRAS (SEQ ID NO: 532) | LGSNRAS (SEQ ID NO: 533) | LLIYLGSNRA (SEQ ID NO: 534) | LG (SEQ ID NO: 535) |
| light chain CDR3 | MQTLQTPYT (SEQ ID NO: 536) | MQTLQTPYT (SEQ ID NO: 537) | MQTLQTPYT (SEQ ID NO: 538) | MQTLQTPY (SEQ ID NO: 539) | MQTLQTPYT (SEQ ID NO: 540) |

TABLE 19

| Antibody YU1018-D06 |
| --- |

| VH | QVQLVESGPGLVKPSQTLSLTCTVSGGSISSGGYYWSWIRQHPGKGLEWIGYIYYSGSTYYNPSLKSRVTISVDTSKNQFSLKLSS VTAADTAVYYCARSGAAGIPWFDPWGQGTLVTVSS |
| VL | QSVLTQPPSVSAAPGQKVTISCSGSSSNIGNNYVSWYQQLPGTAPKLLIYENNERPSGIPDRLSGSKSGTSATLAITGLQTGDEAD YYCGTWDSSLSAVVFGGGTKLTVL |

TABLE 41

| Antibody YU1018-D06 CDRs | | | | | |
| --- | --- | --- | --- | --- | --- |
| | Chothia | AbM | Kabat | Contact | IMGT |
| heavy chain CDR1 | GGSISSGGY (SEQ ID NO: 541) | GGSISSGGYYWS (SEQ ID NO: 542) | SGGYYWS (SEQ ID NO: 543) | SSSGGYYWS (SEQ ID NO: 544) | GGSISSGGYY (SEQ ID NO: 545) |
| heavy chain CDR2 | YYSGS (SEQ ID NO: 546) | YIYYSGSTY (SEQ ID NO: 547) | YIYYSGSTYYNPSLKS (SEQ ID NO: 548) | WIGYIYYSGSTY (SEQ ID NO: 549) | IYYSGST (SEQ ID NO: 550) |
| heavy chain CDR3 | SGAAGIPWFDP (SEQ ID NO: 551) | SGAAGIPWFDP (SEQ ID NO: 552) | SGAAGIPWFDP (SEQ ID NO: 553) | ARSGAAGIPWED (SEQ ID NO: 554) | ARSGAAGIPWFDP (SEQ ID NO: 555) |

TABLE 41-continued

Antibody YU1018-D06
CDRs

| | Chothia | AbM | Kabat | Contact | IMGT |
|---|---|---|---|---|---|
| light chain CDR1 | SGSSSNIGNNYVS (SEQ ID NO: 556) | SGSSSNIGNNYVS (SEQ ID NO: 557) | SGSSSNIGNNYVS (SEQ ID NO: 558) | IGNNYVSWY (SEQ ID NO: 559) | SSNIGNNY (SEQ ID NO: 560) |
| light chain CDR2 | ENNERPS (SEQ ID NO: 561) | ENNERPS (SEQ ID NO: 562) | ENNERPS (SEQ ID NO: 563) | LLIYENNERP (SEQ ID NO: 564) | EN (SEQ ID NO: 565) |
| light chain CDR3 | GTWDSSLSAVV (SEQ ID NO: 566) | GTWDSSLSAVV (SEQ ID NO: 567) | GTWDSSLSAVV (SEQ ID NO: 568) | GTWDSSLSAV (SEQ ID NO: 569) | GTWDSSLSAVV (SEQ ID NO: 570) |

TABLE 20

Antibody YU1018-E01

| | |
|---|---|
| VH | QVQLVQSGAEVKKPGASVKVSCKASGYTFTSYGISWVRQAPGRGLEWMGWISAYNGNTNYAQKLQGRVTMTTDTSTSTAYMELRS LRSDDTAVYYCARGPRDGYNDYWGQGTLVTVSS |
| VL | DVVMTQSPLSLPVTPGEPASISCRSSQSLLHSNGYNYLNWYLQKPGQSPQLLIYLGSNRASGVPDRFSGSGSGTDFTLKISRVEA EDVGVYYCMQPLQTPLTFGGGTKLEIK |

TABLE 42

Antibody YU1018-E01
CDRs

| | Chothia | AbM | Kabat | Contact | IMGT |
|---|---|---|---|---|---|
| heavy chain CDR1 | GYTFTSY (SEQ ID NO: 571) | GYTFTSYGIS (SEQ ID NO: 572) | SYGIS (SEQ ID NO: 573) | TSYGIS (SEQ ID NO: 574) | GYTFTSYG (SEQ ID NO: 575) |
| heavy chain CDR2 | SAYNGN (SEQ ID NO: 576) | WISAYNGNTN (SEQ ID NO: 577) | WISAYNGNTNYAQKL QG (SEQ ID NO: 578) | WMGWISAYNGNTN (SEQ ID NO: 579) | ISAYNGNT (SEQ ID NO: 580) |
| heavy chain CDR3 | GPRDGYNDY (SEQ ID NO: 581) | GPRDGYNDY (SEQ ID NO: 582) | GPRDGYNDY (SEQ ID NO: 583) | ARGPRDGYND (SEQ ID NO: 584) | ARGPRDGYNDY (SEQ ID NO: 585) |
| light chain CDR1 | RSSQSLLHSNGYNYL N (SEQ ID NO: 586) | RSSQSLLHSNGYNYLN (SEQ ID NO: 587) | RSSQSLLHSNGYNYLN (SEQ ID NO: 588) | LHSNGYNYLNWY (SEQ ID NO: 589) | QSLLHSNGYNY (SEQ ID NO: 590) |
| light chain CDR2 | LGSNRAS (SEQ ID NO: 591) | LGSNRAS (SEQ ID NO: 592) | LGSNRAS (SEQ ID NO: 593) | LLIYLGSNRA (SEQ ID NO: 594) | LG (SEQ ID NO: 595) |
| light chain CDR3 | MQPLQTPLT (SEQ ID NO: 596) | MQPLQTPLT (SEQ ID NO: 597) | MQPLQTPLT (SEQ ID NO: 598) | MQPLQTPL (SEQ ID NO: 599) | MQPLQTPLI (SEQ ID NO: 600) |

TABLE 21

Antibody YU1018-A04

| | |
|---|---|
| VH | QVQLVQSGAEVKKPGASVKVSCKASGYTFTSYGISWVRQAPGQGLEWMGWISAYNGNTNYAQKLQGRVTMTTDTSTSTAYMELRS LRSDDTAVYYCARMAGWELIDPWGQGTLVTVSS |
| VL | DVVMTQSPLSLPVTPGEPASISCRSSQSLLHSNGYNYLDWYLQKPGKSPQLLIYLGSNRASGVPDRFSGSGSGTDFTLKISRVEA EDVGVYYCMQALQTPYSFGQGTKVEIK |

TABLE 43

Antibody
YU1018-A04
CDRs

| | Chothia | AbM | Kabat | Contact | IMGT |
|---|---|---|---|---|---|
| heavy chain CDR1 | GYTFTSY (SEQ ID NO: 601) | GYTFTSYGIS (SEQ ID NO: 602) | SYGIS (SEQ ID NO: 603) | TSYGIS (SEQ ID NO: 604) | GYTFTSYG (SEQ ID NO: 605) |
| heavy chain CDR2 | SAYNGN (SEQ ID NO: 606) | WISAYNGNIN (SEQ ID NO: 607) | WISAYNGNTNYAQKL QG (SEQ ID NO: 608) | WMGWISAYNGNTN (SEQ ID NO: 609) | ISAYNGNT (SEQ ID NO: 610) |
| heavy chain CDR3 | MAGWELIDP (SEQ ID NO: 611) | MAGWELIDP (SEQ ID NO: 612) | MAGWELIDP (SEQ ID NO: 613) | ARMAGWELID (SEQ ID NO: 614) | ARMAGWELIDP (SEQ ID NO: 615) |
| light chain CDR1 | RSSQSLLHSNGYNYL D (SEQ ID NO: 616) | RSSQSLLHSNGYNYLD (SEQ ID NO: 617) | RSSQSLLHSNGYNYLD (SEQ ID NO: 618) | LHSNGYNYLDWY (SEQ ID NO: 619) | QSLLHSNGYNY (SEQ ID NO: 620) |
| light chain CDR2 | LGSNRAS (SEQ ID NO: 621) | LGSNRAS (SEQ ID NO: 622) | LGSNRAS (SEQ ID NO: 623) | LLIYLGSNRA (SEQ ID NO: 624) | LG (SEQ ID NO: 625) |
| light chain CDR3 | MQALQTPYS (SEQ ID NO: 626) | MQALQTPYS (SEQ ID NO: 627) | MQALQTPYS (SEQ ID NO: 628) | MQALQTPY (SEQ ID NO: 629) | MQALQTPYS (SEQ ID NO: 630) |

TABLE 22

Antibody YU1018-G09

| VH | EVQLLESGAEVKKPGESLKISCKGSGYSFTSYWIGWVRQMPGKGLEWMGIIYPGDSDTRYSPSFQGQVTISADKSISTAYLQWSSL KASDTAMYYCARGVGSVVFDYWGQGTLVTVSS |
|---|---|
| VL | DVVMTQSPLPLPVTPGEPASISCRSSQSLLHSNGYNYLDWYLQKPGQSPQLLIYLGSNRASGVPDRFSGSGSGTDFTLKISRVEAE DVGVYYCMQALQTPPTFGQGTKVEIK |

TABLE 44

Antibody
YU1018-G09
CDRs

| | Chothia | AbM | Kabat | Contact | IMGT |
|---|---|---|---|---|---|
| heavy chain CDR1 | GYSFTSY (SEQ ID NO: 631) | GYSFTSYWIG (SEQ ID NO: 632) | SYWIG (SEQ ID NO: 633) | TSYWIG (SEQ ID NO: 634) | GYSFTSYW (SEQ ID NO: 635) |
| heavy chain CDR2 | YPGDSD (SEQ ID NO: 636) | IIYPGDSDTR (SEQ ID NO: 637) | IYPGDSDTRYSPSFQG (SEQ ID NO: 638) | WMGIIYPGDSDTR (SEQ ID NO: 639) | IYPGDSDT (SEQ ID NO: 640) |
| heavy chain CDR3 | CVGSVVEDY (SEQ ID NO: 641) | GVGSVVEDY (SEQ ID NO: 642) | GVGSVVEDY (SEQ ID NO: 643) | ARGVGSVVED (SEQ ID NO: 644) | ARGVGSVVFD (SEQ ID NO: 645) |
| light chain CDR1 | RSSQSLLHSNGYNYL D (SEQ ID NO: 646) | RSSQSLLHSNGYNYLD (SEQ ID NO: 647) | RSSQSLLHSNGYNYLD (SEQ ID NO: 648) | LHSNGYNYLDWY (SEQ ID NO: 649) | QSLLHSNGYNY (SEQ ID NO: 650) |
| light chain CDR2 | LGSNRAS (SEQ ID NO: 651) | LGSNRAS (SEQ ID NO: 652) | LGSNRAS (SEQ ID NO: 653) | LLIYLGSNRA (SEQ ID NO: 654) | LG (SEQ ID NO: 655) |
| light chain CDR3 | MQALQTPPT (SEQ ID NO: 656) | MQALQTPPT (SEQ ID NO: 657) | MQALQTPPT (SEQ ID NO: 658) | MQALQTPP (SEQ ID NO: 659) | MQALQTPPT (SEQ ID NO: 660) |

In some embodiments, the antibody or antigen-binding fragment comprises three heavy chain CDRs and three light chain CDRs having sequences selected from:

a) SEQ ID NOs: 3, 8, and 13 and SEQ ID NOs: 18, 23, and 28 (antibody E05a);

b) SEQ ID NOs: 33, 38, and 43 and SEQ ID NOs: 48, 53, and 58 (antibody H08);

c) SED ID NOs: 63, 68, and 73 and SED ID NOs: 78, 83, and 88 (antibody F06);

d) SEQ ID NOs: 93, 98, and 103 and SEQ ID NOs: 108, 113, and 118 (antibody A12);

e) SED ID NOs: 123, 128, and 133 and SED ID NOs: 138, 143, and 148 (antibody G01);

f) SED ID NOs: 153, 158, and 163 and SED ID NOs: 168, 173 and 178 (antibody E11);

g) SEQ ID NOs: 183, 188, and 193 and SEQ ID NOs: 198, 203, and 208 (antibody B06);

h) SED ID NOs: 213, 218, and 223 and SED ID NOs: 228, 233, and 238 (antibody D12);

i) SED ID NOs: 243, 248, and 253 and SED ID NOs: 258, 263 and 268 (antibody H01);

j) SED ID NOs: 273, 278, and 283 and SED ID NOs: 288, 293, and 298 (antibody C11);

k) SED ID NOs: 303, 308, and 313 and SED ID NOs: 318, 323, and 328 (antibody E05b);

l) SED ID NOs: 333, 338, and 343 and SED ID NOs: 348, 353 and 358 (antibody F10);

m) SED ID NOs: 363, 368 and 373 and SED ID NOs: 378, 383 and 388 (antibody G10);

n) SEQ ID NOs: 393, 398, and 403 and SEQ ID NOs: 408, 413, and 418 (antibody E04);

o) SED ID NOs: 423, 428, and 433 and SED ID NOs: 438, 443, and 448 (antibody E07);

p) SEQ ID NOs: 453, 458, and 463 and SED ID NOs: 468, 473, and 478 (antibody E12);

q) SED ID NOs: 483, 488, and 493 and SED ID NOs: 498, and 503, and 508 (antibody D08);

r) SED ID NOs: 513, 518, and 523 and SED ID NOs: 528, 533, and 538 (antibody E10);

s) SEQ ID NOs: 543, 548, and 553 and SEQ ID NOs: 558, 563, and 568 (antibody D06); and t) SED ID NOs: 573, 578, and 583 and SED ID NOs: 588, 593, and 598 (antibody E01), or having sequences that differ from the selected CDR sequences (a)-(t) by at most two conservative amino acid substitutions in each CDR.

In some embodiments, the antibody or antigen-binding fragment comprises three heavy chain CDRs and three light chain CDRs with sequences identical to the selected CDRs (a)-(t). In some embodiments, the antibody or antigen-binding fragment comprises three heavy chain CDRs and three light chain CDRs having sequences that differ from the selected CDR sequences (a)-(t) by at most two conservative amino acid substitutions in each CDR, or by at most 1 conservative amino acid substitution in each CDR. In some embodiments, the antibody or antigen-binding fragment comprises three heavy chain CDRs and three light chain CDRs having sequences that differ from the selected CDR sequences (a)-(t) by 6 conservative amino acid changes in total across all 6 CDRs, 5 conservative amino acid substitutions in total across all 6 CDRs, 4 conservative amino acid substitutions in total across all 6 CDRs, 3 conservative amino acid substitutions in total across all 6 CDRs, 2 conservative amino acid substitutions in total across all 6 CDRs, or 1 conservative amino acid substitution total across all 6 CDRs.

In some embodiments, the antibody or antigen-binding fragment comprises three heavy chain CDRs and three light chain CDRs having sequences selected from:

b) SEQ ID NOs: 33, 38, and 43 and SEQ ID NOs: 48, 53 and 58 (antibody H08);

d) SEQ ID NOs: 93, 98, and 103 and SEQ ID NOs: 108, 113, and 118 (antibody A12);

g) SEQ ID NOs: 183, 188, and 193 and SEQ ID NOs: 198, 203, and 208 (antibody B06);

n) SEQ ID NOs: 393, 398, and 403 and SEQ ID NOs: 408, 413, and 418 (antibody E04);

s) SEQ ID NOs: 543, 548, and 553 and SEQ ID NOs: 558, 563, and 568 (antibody D06); and t) SEQ ID NOs: 573, 578, and 583 and SEQ ID NOs: 588, 593, and 598 (antibody E01), or having sequences that differ from the selected CDR sequences b), d), g), n) s), and t) by at most two conservative amino acid substitutions in each CDR.

In some embodiments, the antibody or antigen-binding fragment comprises three heavy chain CDRs and three light chain CDRs with sequences identical to the selected CDRs (b), (d), (g), (n), (s) or (t). In some embodiments, the antibody or antigen-binding fragment comprises three heavy chain CDRs and three light chain CDRs having sequences that differ from the selected CDR sequences (b), (d), (g), (n), (s) or (t) by at most two conservative amino acid substitutions in each CDR, or by at most 1 conservative amino acid substitution in each CDR. In some embodiments, the antibody or antigen-binding fragment comprises three heavy chain CDRs and three light chain CDRs having sequences that differ from the selected CDR sequences (b), (d), (g), (n), (s) or (t) by 6 conservative amino acid changes in total across all 6 CDRs, 5 conservative amino acid substitutions in total across all 6 CDRs, 4 conservative amino acid substitutions in total across all 6 CDRs, 3 conservative amino acid substitutions in total across all 6 CDRs, 2 conservative amino acid substitutions in total across all 6 CDRs, or 1 conservative amino acid substitution total across all 6 CDRs.

In some embodiments, the antibody framework regions are human antibody framework regions. In some embodiments, the antibody is a full length bivalent monospecific monoclonal antibody. In some embodiments, the antibody comprises human IgG1, IgG2, or IgG4 heavy chain constant regions. In some embodiments, the antibody comprises a human IgG1 constant region. In some embodiments, the antibody Fc region has at least one engineered mutation that reduces antibody binding to at least an Fc γ receptor. In some embodiments, the mutation is N297A. In some embodiments, the antibody Fc region has at least one engineered mutation that reduces complement fixation. In some embodiments, the mutation is K322A.

In some embodiments, the antibody is a Fab, optionally wherein the Fab is PEGylated.

In some embodiments, the antibody or antigen binding fragment is further capable of binding to cynomolgus monkey NBL1. In some embodiments, the antibody or antigen binding fragment is further capable of binding to mouse NBL1.

In some embodiments, the antibody is an IgG monoclonal antibody. In particular embodiments, the antibody is an IgG1 or IgG4 monoclonal antibody.

In some embodiments, the antibody is a human monoclonal antibody. In some embodiments, the antibody is a humanized antibody. In some embodiments, the antibody is a chimeric mouse-human antibody. In some embodiments, the agent comprises an NBL1-binding antigen binding fragment selected from a Fab, Fab', F(ab')$_2$, Fv, scFv, Fd, or diabody.

In some embodiments the antibody or antigen binding fragment has a binding affinity (K$_D$) for human NBL1 of less than 100 nM. In some embodiments the antibody or antigen binding fragment has a binding affinity (K$_D$) for human NBL1 of less than 10 nM. In some embodiments the antibody or antigen binding fragment has a binding affinity (K$_D$) for human NBL1 of less than 5 nM. In some embodiments the antibody or antigen binding fragment has a binding affinity (K$_D$) for human NBL1 of less than 1 nM.

In certain embodiments, the NBL1 dimerization inhibitor is an antibody. In some of these embodiments, the antibody is a monoclonal antibody. In some of these embodiments, the antibody is polyclonal. In some embodiments the dimerization inhibitor binds to at least one of the synonymous β-strands from each NBL1 monomer.

5.3.3. NBL1 Expression Inhibitors

In some embodiments, the agent is capable of inhibiting NBL1 expression.

In certain embodiments, the agent inhibits transcription of the NBL1 gene. In certain embodiments, the agent causes degradation of the NBL1 mRNA. In certain embodiments, the agent inhibits translation of the NBL1 mRNA. In certain embodiments, the agent targets NBL1 protein for degradation.

In specific embodiments, the agent is an antisense oligonucleotide. In specific embodiments, the agent mediates RNA interference. In particular RNA interference embodiments, the agent is a short hairpin RNA (shRNA) or short interfering RNA (siRNA). In specific embodiments, the agent is a microRNA (miRNA). In specific embodiments, the agent is a sequence-specific mRNA interferase.

5.4. Methods of Slowing Decline in Kidney Function

In a further aspect, methods are provided for slowing decline in kidney function in a subject who has, or is at risk for, type 1 or type 2 diabetes, or who has or is at risk for developing a glomerular disease. The method comprises administering to the subject an effective amount of an agent capable of inhibiting NBL1 activity. In various embodiments, the agent capable of inhibiting NBL1 activity is an inhibitor as described in Section 5.3.1, 5.3.2, or 5.3.3 above.

In some embodiments, the method slows progression of microalbuminuria, slows progression of macroalbuminuria, slows progression of proteinuria, or slows reduction of glomerular filtration rate (GFR).

In some embodiments, the method prevents onset of or slows progressive kidney function decline (PKFD). In some embodiments, the agent inhibits the progression of at least one or more symptoms associated with PKFD. In some embodiments, the rate of decline in kidney function of the subject in relation to an untreated control group is reduced by 10%, 20%, 30%, 40%, 50%, 60%, 70%, 80% or 90%.

In some embodiments, the method prevents onset of or slows progression to end-stage kidney disease (ESKD). In some embodiments, the method inhibits the progression of at least one or more symptoms associated with ESKD. In some embodiments, the method inhibits progression to required dialysis.

In some embodiments, the method slows progression of chronic kidney disease (CKD) stage 1 to stage 2, stage 2 to stage 3, stage 3A to stage 3B, stage 3B to stage 4, stage 4 to stage 5, or progression from stage 5 without dialysis to stage 5 with dialysis.

In some embodiments, the subject has type 1 diabetes. In some embodiments, the subject has type 2 diabetes. In some embodiments, the subject is pre-diabetic. In some embodiments, the subject is not prediabetic as measured by hemoglobin A1c levels or blood glucose levels but is at risk for type 1 diabetes or type 2 diabetes and has elevated NBL1 plasma levels. In some embodiments, the subject has a glomerular disorder. In particular embodiments, the subject has a glomerular disorder and does not have type 1 or type 2 diabetes. In particular embodiments, the glomerular disorder is selected from the group consisting of focal segmental glomerulosclerosis (FSGS), chronic glomerulopathies, hereditary nephritis, and minimal change disease.

In some embodiments, the method effectively reduces the availability of circulating free NBL1 in subjects having type 1 or type 2 diabetes, or who are prediabetic, or who are at risk for type 1 diabetes or type 2 diabetes and have elevated NBL1 plasma levels, as compared to normal subjects who do not have type 1 or type 2 diabetes or prediabetes. In some embodiments, the method effectively reduces the availability of circulating free NBL1 in subjects who have a glomerular disease. In certain embodiments, the method effectively reduces the availability of circulating free NBL1 in subjects who have a glomerular disease selected from the group consisting of focal segmental glomerulosclerosis (FSGS), chronic glomerulopathies, hereditary nephritis, and minimal change disease.

In various embodiments, the agent is an agent described in Section 5.3.1, 5.3.2, or 5.3.3 above, incorporated herein by reference.

5.5. Methods of Treating Diabetic Kidney Disease or a Glomerular Disease

In a further aspect, methods are presented for treating diabetic kidney disease (DKD) in a subject who has type 1 or type 2 diabetes or who has a glomerular disease. The method comprises administering to the subject an effective amount of an agent capable of inhibiting NBL1 activity.

In some embodiments, the subject has type 1 or type 2 diabetes and one or more of glomerular hypertrophy, glomerulosclerosis, tubulointerstitial inflammation, fibrosis, glomerular hyperfiltration, progressive albuminuria, declining GFR, and ESKD.

In some embodiments, the subject has a glomerular disease. In certain embodiments, the subject has a glomerular disease and does not have type 1 or type 2 diabetes. In certain embodiments, the glomerular disorder is selected from the group consisting of focal segmental glomerulosclerosis (FSGS), chronic glomerulopathies, hereditary nephritis, and minimal change disease.

In various embodiments, the agent is an agent described in Section 5.3.1, 5.3.2, or 5.3.3 above, incorporated here by reference.

5.6. Dose Regimen

In some embodiments of the methods described herein, the agent is administered parenterally. In particular embodiments, the agent is administered intravenously. In specific embodiments, the subject is on dialysis and the agent is administered intravenously. In particular embodiments, the agent is administered subcutaneously.

In some embodiments, the agent is administered once. In some embodiments, the agent is administered more than one. In particular embodiments, the agent is administered for at least 3 months. In particular embodiments, the agent is administered for at least 6 months. In particular embodiments, the agent is administered for at least 12 months.

5.7. Antibodies and Pharmaceutical Formulations Thereof

In another aspect, antibodies or antigen binding fragments are provided that are capable of binding to NBL1 and inhibiting NBL1-induced toxicity of human podocytes. Embodiments include all antibodies and antigen-binding fragment embodiments described in Section 5.3.2 above, which is incorporated herein by reference.

In a further aspect, pharmaceutical compositions are provided. The pharmaceutical compositions comprise the antibody or antigen binding fragment described herein and a pharmaceutically acceptable carrier. In some embodiments, the composition is formulated for parenteral administration. In some embodiments, the composition is formulated for intravenous administration. In some embodiments, the composition is formulated for subcutaneous administration.

5.8. Additional Embodiments

Additional embodiments are set out in the following numbered clauses.

1. A method for delaying onset or progression of kidney damage in a subject who has type 1 diabetes or type 2 diabetes or a glomerular disease, the method comprising:
   administering to the subject an effective amount of an agent capable of inhibiting NBL1 activity.
2. The method of clause 1, wherein the agent is capable of binding to NBL1.
3. The method of clause 2, wherein the agent comprises a bone morphogenetic protein (BMP) or soluble fragment thereof.
4. The method of clause 3, wherein the agent comprises a soluble fragment of human BMP-2.
5. The method of clause 3 or clause 4, wherein the agent further comprises a moiety that extends serum half-life.
6. The method of clause 5, wherein the half-life extension moiety is an antibody Fc domain.
7. The method of clause 5, wherein the half-life extension moiety is at least one covalently linked polyethylene glycol (PEG) moiety.
8. The method of clause 2, wherein the agent comprises an antibody or antigen binding fragment thereof.
9. The method of clause 2, wherein the agent is capable of inhibiting dimerization of NBL1.
10. The method of clause 1, wherein the agent is capable of inhibiting NBL1 expression.
11. The method of any one of clauses 1-10, wherein the subject has type 1 diabetes.
12. The method of any one of clauses 1-10, wherein the subject has type 2 diabetes.
13. The method of any one of clauses 1-10, wherein the subject has a glomerular disease.
14. The method of clause 13, wherein the subject with glomerular disease does not have type 1 diabetes or type 2 diabetes.
15. The method of clause 13 or clause 14, wherein the glomerular disease is selected from the group consisting of focal segmental glomerulosclerosis (FSGS), chronic glomerulopathies, hereditary nephritis, and minimal change disease.
16. The method of clause 15, wherein the glomerular disease is focal segmental glomerulosclerosis.
17. The method of clause 15, wherein the glomerular disease is chronic glomerulopathies.
18. The method of clause 15, wherein the glomerular disease is hereditary nephritis.
19. The method of clause 15, wherein the glomerular disease is minimal change disease.
20. The method of any one of clauses 1-19, wherein the method prevents onset of or slows decline in kidney function.
21. A method of slowing decline in kidney function in a subject who has type 1 or type 2 diabetes or a glomerular disease, the method comprising:
   administering to the subject an effective amount of an agent capable of inhibiting NBL1 activity.
22. The method of clause 21, wherein the method prevents onset of or slows progressive kidney function decline (PKFD).
23. The method of clause 21, wherein the method prevents onset of or slows progression to end-stage kidney disease (ESKD).
24. The method of any one of clauses 21-23, wherein the agent is capable of binding to NBL1.
25. The method of clause 24, wherein the agent comprises a bone morphogenetic protein (BMP) or soluble fragment thereof.
26. The method of clause 25, wherein the agent comprises a soluble fragment of human BMP-2.
27. The method of clause 25 or clause 26, wherein the agent further comprises a moiety that extends serum half-life.
28. The method of clause 27, wherein the half-life extension moiety is an antibody Fc domain.
29. The method of clause 27, wherein the half-life extension moiety is at least one covalently linked polyethylene glycol (PEG) moiety.
30. The method of clause 24, wherein the agent comprises an antibody or antigen binding fragment thereof.
31. The method of clause 24, wherein the agent is capable of inhibiting dimerization of NBL1.
32. The method of any one of clauses 21-23, wherein the agent is capable of inhibiting NBL1 expression.
33. The method of any one of clauses 21-32 wherein the subject has type 1 diabetes.
34. The method of any one of clauses 21-32, wherein the subject has type 2 diabetes.
35. The method of any one of clauses 21-32, wherein the subject has a glomerular disease.
36. The method of clause 35, wherein the subject with glomerular disease does not have type 1 diabetes or type 2 diabetes.
37. The method of clause 35 or clause 36, wherein the glomerular disease is selected from the group consisting of focal segmental glomerulosclerosis (FSGS), chronic glomerulopathies, hereditary nephritis, minimal change disease.
38. The method of clause 37, wherein the glomerular disease is focal segmental glomerulosclerosis.
39. The method of clause 37, wherein the glomerular disease is chronic glomerulopathies.
40. The method of clause 37, wherein the glomerular disease is hereditary nephritis.

41. The method of clause 37, wherein the glomerular disease is minimal change disease.

42. A method of treating diabetic kidney disease (DKD) or a glomerular disease in a subject who has type 1 or type 2 diabetes or a glomerular disease, the method comprising:

administering to the subject an effective amount of an agent capable of inhibiting NBL1 activity.

43. The method of clause 42, wherein the agent is capable of binding to NBL1.

44. The method of clause 43, wherein the agent comprises a bone morphogenetic protein (BMP) or soluble fragment thereof.

45. The method of clause 44, wherein the agent comprises a soluble fragment of human BMP-2.

46. The method of clause 44 or clause 45, wherein the agent further comprises a moiety that extends serum half-life.

47. The method of clause 46, wherein the half-life extension moiety is an antibody Fc domain.

48. The method of clause 46, wherein the half-life extension moiety is at least one covalently linked polyethylene glycol (PEG) moiety.

49. The method of clause 43, wherein the agent comprises an antibody or antigen binding fragment thereof.

50. The method of clause 43, wherein the agent is capable of inhibiting dimerization of NBL1.

51. The method of clause 42, wherein the agent is capable of inhibiting NBL1 expression.

52. The method of any one of clauses 42-51, wherein the subject has type 1 diabetes.

53. The method of any one of clauses 42-51, wherein the subject has type 2 diabetes.

54. The method of any one of clauses 42-51, wherein the subject has a glomerular disease.

55. The method of clause 54, wherein the subject with glomerular disease does not have type 1 diabetes or type 2 diabetes.

56. The method of clause 54 or clause 55, wherein the glomerular disease is selected from the group consisting of focal segmental glomerulosclerosis, chronic glomerulopathies, hereditary nephritis, minimal change disease.

57. The method of clause 56, wherein the glomerular disease is focal segmental glomerulosclerosis.

58. The method of clause 56, wherein the glomerular disease is chronic glomerulopathies.

59. The method of clause 56, wherein the glomerular disease is hereditary nephritis.

60. The method of clause 56, wherein the glomerular disease is minimal change disease.

61. The method of any one of clauses 1-60, wherein the agent is administered parenterally.

62. The method of any one of clauses 1-61, wherein the agent is administered for at least 3 months.

63. The method of clause 62, wherein the agent is administered for at least 6 months.

64. The method of clause 63, wherein the agent is administered for at least 12 months.

6. EXAMPLES

Below are examples of specific embodiments for carrying out the present disclosure. The examples are offered for illustrative purposes only, and are not intended to limit the scope of the present disclosure in any way. Efforts have been made to ensure accuracy with respect to numbers used (e.g., amounts, temperatures, etc.), but some experimental error and deviation should, of course, be allowed for.

The practice of the present disclosure will employ, unless otherwise indicated, conventional methods of protein chemistry, biochemistry, recombinant DNA techniques and pharmacology. Such techniques are explained fully in the literature.

6.1. Example 1. NBL1 is Directly Toxic to Podocytes and Renal Tubular Cells

Increased DAN protein (Grem1, Grem2, Grem3, Cerberus, NBL1, SOST, and USG1) levels have been associated with severe disease-states in adult kidneys. Wen et al., *Biochimie* 160:113-121 (2019).

To assess whether the increased presence of a DAN protein has a causal effect on kidney damage, we cultured human podocytes (HuPodo), human mesangial cells (HuHMRC), and human renal tubular cells (HuK2) in vitro for 48 hours in the presence or absence of human NBL1. Human umbilical vein endothelial cells (Huvec) were used as a control. Podocytes were cultured in increasing concentrations of NBL1: 0.2 µg/ml, 1.0 µg/ml, and 2.0 µg/ml. Mesangial cells and tubular cells were cultured in 2 µg/ml NBL1. Human umbilical vein endothelial cells were cultured in increasing concentrations of 0.2 µg/ml, 2 µg/ml, and 10 µg/ml NBL1.

FIGS. 1A-1D are bar graphs summarizing cell death analysis data, quantified using arbitrary units (AU) for convenience. The results show increased apoptosis/death of human podocytes, and to a lesser degree mesangial and tubular cells, directly correlated to the added presence of NBL1 to culture media. Cell death was undetectable in NBL1-cultured human umbilical vein endothelial cells (Huvec), even at higher concentrations.

Figures 2A, 2B:
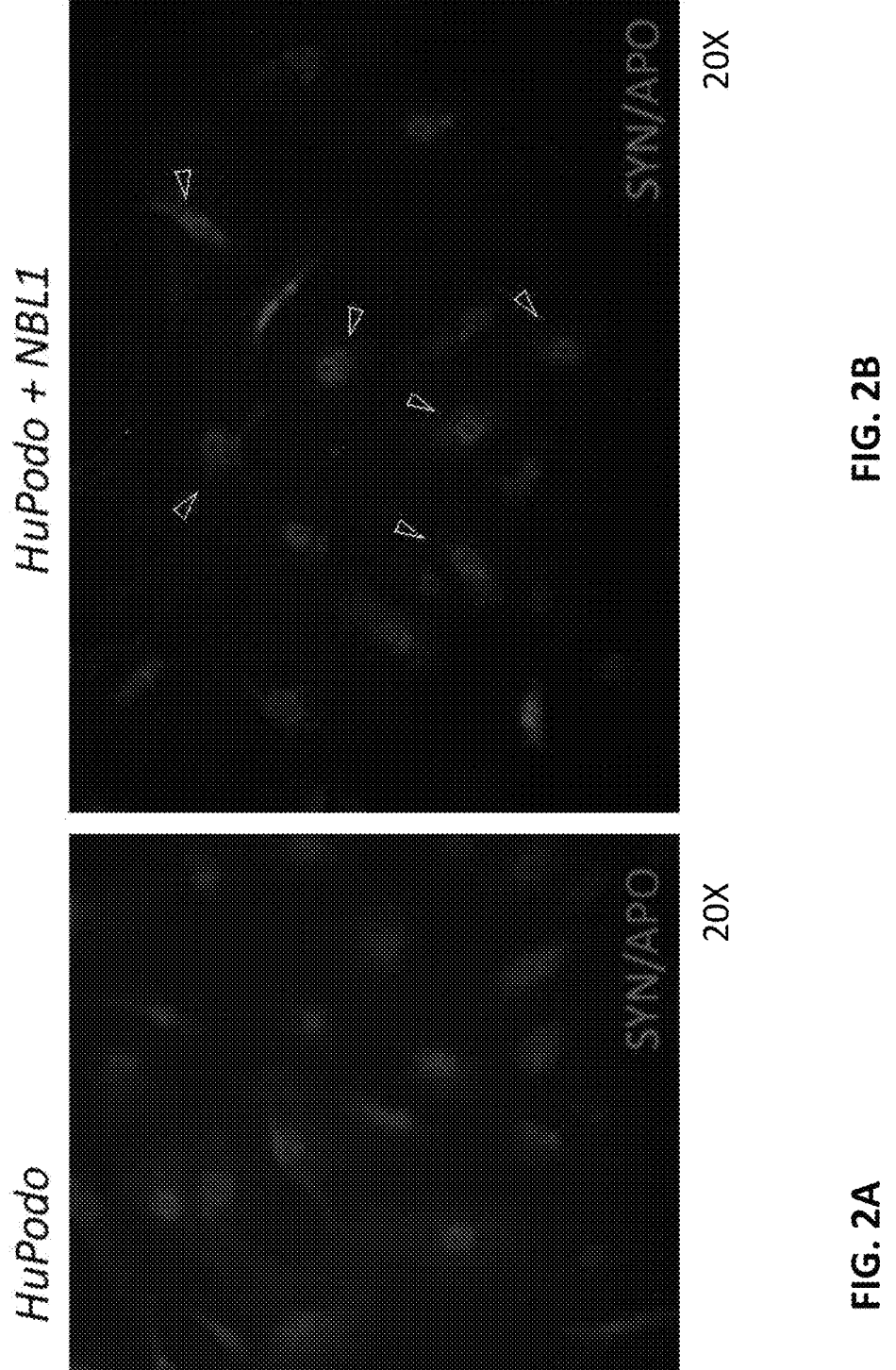
Figure 2C:
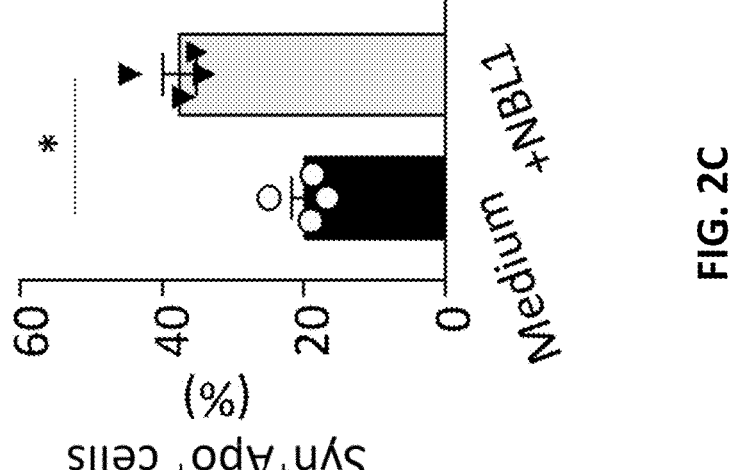

FIGS. 2A-2B show representative images of confocal analysis conducted on human podocytes left untreated (FIG. 2A) or cultured with NBL1 at 2 µg/ml (FIG. 2B), stained with Synaptopodin and Apoptag. Merged pictures are presented. These micrographs show evidence of NBL1-induced apoptosis of human podocytes. The arrows highlight the colocalization of Apoptag and Synaptopodin, which are markers for apoptosis and podocytes respectively. The image emphasizes that the majority of podocytes are undergoing apoptosis. FIG. 2C is a bar graph quantifying the percentage of Apoptag Synaptopodyn$^+$ double positive human podocytes in the presence/absence of NBL1 (n=3). The results indicate increased level of apoptotic differentiated human podocytes in the presence of NBL1.

Figure 3:
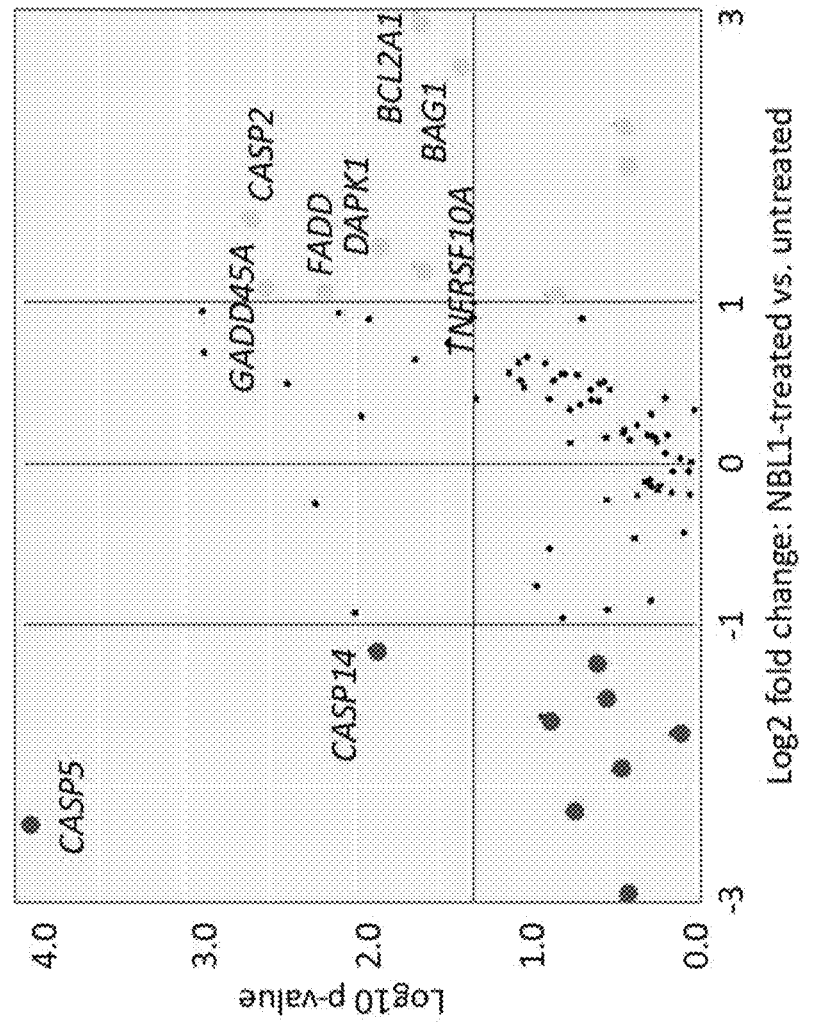
FIG. 3 depicts changes in levels of apoptosis-related transcripts in human podocytes cultured with NBL1 at 2 μg/ml as compared to untreated cells.

FIG. 3 shows transcriptome analysis of apoptosis-related genes of human podocytes cultured with NBL1 at 2 µg/ml or left untreated. The data show significant increase in expression of apoptosis-related genes upon exposure to NBL-1 in vitro.

Collectively, these experiments show that NBL1 is directly toxic to podocytes and renal tubular cells, with exposure to NBL1 causing apoptosis of human podocytes and renal tubular cells.

6.2. Example 2. BMP Proteins are not Expressed in and are not Secreted by Kidney Cells In Vitro Like other DAN proteins, NBL1 is known to interact with bone morphogenetic proteins. Hung et al., Biol. of Reprod. (2012) 86 (5): 158, 1-9.

To determine whether NBL1 exerts its toxicity through inhibition of BMPs within the kidney, we analyzed whether BMP2, BMP4 and BMP7 were expressed as mRNA in human podocytes. We did not detect any mRNA expression of any of the BMPs. Next, we assessed whether BMP2, BMP4 or BMP7 are secreted from podocytes into the supernatant, thus allowing an autocrine/paracrine pro-survival effect. We did not detect any of the BMPs in the supernatants of human podocytes, thus confirming that podocytes are not able to synthesize and secrete BMPs in vitro (data not shown).

The toxic effect of NBL1 on podocytes is thus independent of the presence of BMPs; NBL1's pro-apoptotic effect is not mediated via inhibition of BMPs.

Figure 4:
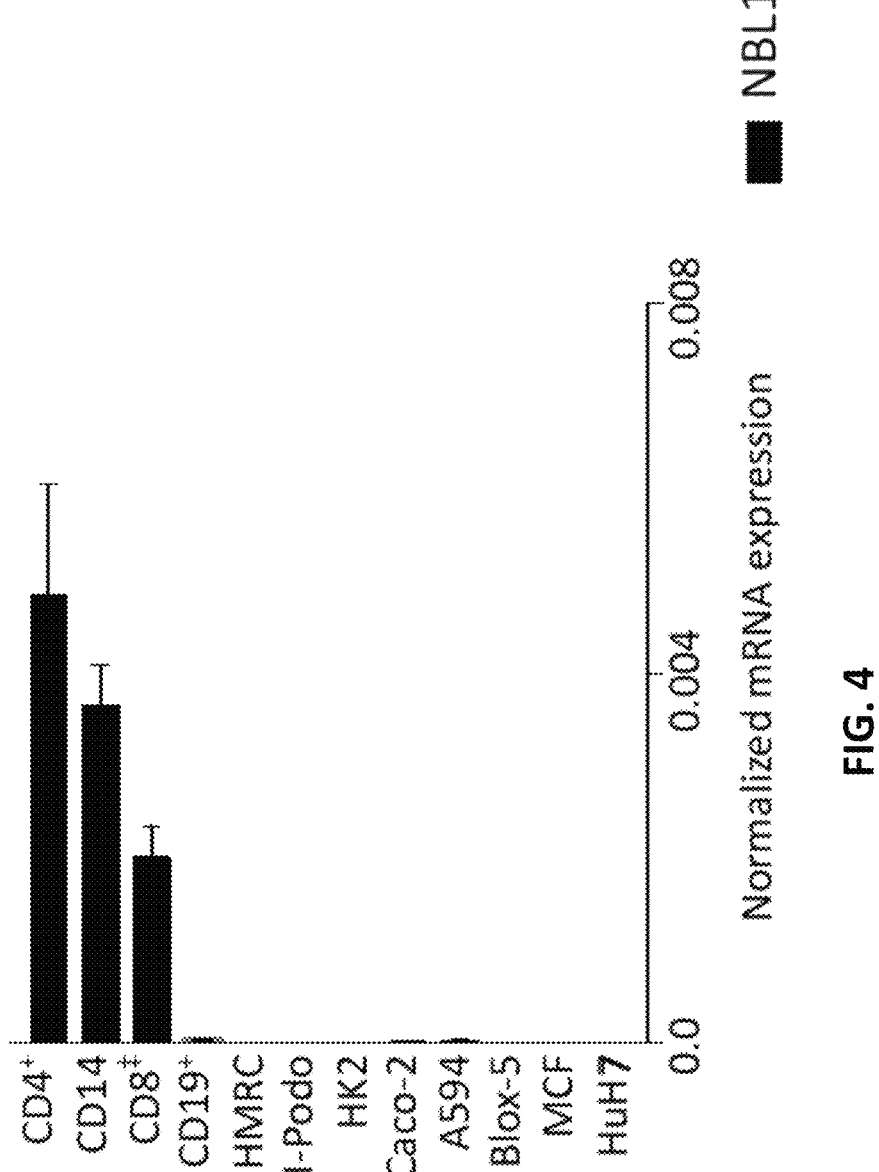
FIG. 4 is a bar graph quantifying expression of NBL1 mRNA in human immune cells and cell lines. mRNA levels were normalized to beta-actin level.

6.3. Example 3. NBL1 is not Expressed in Kidney Cells, but is Expressed in Circulating Immune Cells, Intestinal and Muscle Tissue Having determined that NBL1 is directly toxic to podocytes and renal tubular cells, we sought its physiological origin by measuring mRNA expression of NBL1 in a number of human cell lines, including kidney cell lines, using RT-PCR with expression normalized to beta actin expression. FIG. 4 shows that NBL1 was undetectable in kidney-derived cells. NBL1 was also undetectable in various other cell lines. However, it was highly expressed in immune cells, such as CD14$^+$ monocytes and CD4$^+$ and CD8$^+$ T cells (see FIG. 4).

Additional analysis using flow-cytometry of peripheral blood mononuclear cells (PBMCs) isolated from blood samples of healthy volunteers confirmed high expression of NBL1 protein in myeloid (CD14$^+$) cells and various T cell subsets (CD3$^+$, CD4$^+$ and CD8$^+$ T cells) (see FIGS. 5A-5B). Human PBMCs were purified from 8 ml blood samples collected from non-diabetic subjects (n=5) at the ASST Sacco-FBF in Milan (Italy) by using Lymphoprep (07801, Stem Cell Technologies, Cambridge, MA) and cells were then stained for flow-cytometry analysis with anti-human CD3 (300330), anti-CD45 (560178), anti-CD4 (561030), anti-CD8 (560774), anti-CD14 (561707) from Biolegend (San Diego, CA) and BD Biosciences (San Jose, CA) to quantify surface expression. Rabbit polyclonal anti-NBL1 (Sigma, HPA007394) followed by donkey anti-rabbit AlexaFluor488 antibody (ThermoFisher Scientific) was used to stain for NBL1. Cells were analyzed using a BD FACS Celesta (BD Biosciences).

To further explore the expression of NBL1, a comprehensive immunostaining study of NBL1 human tissue expression was performed. In this study, NBL1 expression was detected by immunohistochemistry and flow cytometry on human tissue specimens. NBL1 immunoreactivity was semi-quantitatively scored based on the percentage of NBL1 positive cells in the total cells per region of interest. The scoring was as follows: <10%, 1+; 10-30%, 2+; 30-50%, 3+; 50-80%, 4+, and >80%, 5+. Archival formalin-fixed, paraffin-embedded tissue samples of non-diabetic subjects from Pathology Unit, University of Parma were used for NBL1 immunostaining (anti-NBL1 primary antibody #HPA007394, Merck). A further magnification of each panel is shown in the insert on the top right black square, in which black arrows highlight the positive staining. Original magnification 20×, scale bar 100 um (See FIG. 5C).

A semi-quantitative score was also applied to NBL1 expression detected in T cells (CD3$^+$NBL1$^+$), B cells (CD19$^+$NBL1$^+$) and monocytes (CD14$^+$NBL1$^+$) (See FIG. 5A) based on the quantification of percentage of double positive cells as follows: <15%, 1+; 15-45%, 2+; 45-75%, 3+; 75-90%, 4+, and >90%, 5+.

The semi-quantitative scores illustrating NBL1 protein expression in human tissues are illustrated in the bar graph presented in FIG. 5D. For histocytochemistry, the mean value of the score calculated in n=3 separate slides are presented. For flow cytometry, scores representing T cells, B cells and monocytes, mean values obtained in n=5 samples analyzed are presented. (See FIG. 5D).

The results of the study demonstrate that NBL1, which is not expressed in kidney, is expressed in circulatory immune cells, notably T cells and monocytes, in various intestinal tissues, and muscle, with lesser expression in reproductive tissues, bone and bone marrow.

6.4. Example 4. Neutralizing NBL1 with an Antagonist Prevents Toxicity

Having shown that NBL1 is toxic to podocytes and renal tubular cells, that this toxicity is directly mediated, and that NBL1 is not produced locally in renal cells but is instead expressed in circulating immune cells and other non-renal tissues, we tested whether NBL1 could be an appropriate target for direct therapeutic intervention to protect kidney cells from damage.

Human podocytes were cultured for 48 hours in the presence of NBL1 (2 μg/ml) in the presence or absence of soluble BMP2 in a 1:1 ratio (NBL1:sBMP2=1:1). Cell death was detected by ELISA. Incubation with soluble BMP2 significantly reduced the cell death effects experienced by human podocytes cultured in the presence of NBL1, indicating that soluble BMP2 is capable of partially neutralizing NBL1's pro-apoptotic effect on human podocytes in vitro. Results for the above experiments are shown in FIG. 6. Three independent experiments were run in duplicate. Data are presented as mean±SEM. A commercial anti-NBL1 tool antibody (Sigma) showed a smaller effect (data not shown).

6.5. Example 5. Human Anti-NBL1 Antibody Discovery Campaign

Naïve human phage display libraries were panned to discover Fabs capable of binding human NBL1 (UniProt ID P41271), and further screened for potential inter species cross reactivity to mouse NBL1 (UniProt ID Q61477) and/or cynomolgus ("cyno") NBL1 (UniProt ID A0A2K5WIY3). The top 25 Fabs were cloned into expression vectors and expressed as full length human IgG1 antibodies. Antigen binding of the IgG1 formatted antibodies was tested by ELISA and EC50 values were calculated. Twenty (20) IgG1 antibodies were shown to bind to human, mouse, and cyno NBL1 with EC50 in the ELISA of between 10 ng/ml and 100 ng/ml (~0 to 600 pM).

Tables presented in Section 5.3.2 above provide the VH and VL sequences, and separately, the CDR sequences, of the 20 IgG1 antibodies.

6.6. Example 6. Monoclonal Anti-NBL1 Antibodies Rescue NBL1-Mediated Apoptosis of Human Podocytes In Vitro Having demonstrated that NBL1 is directly toxic to podocytes and renal tubular cells, and that the toxicity can be averted using sBMP2, which is capable of specific binding to NBL1, we decided to assess the effects of monoclonal anti-NBL1 antibodies on the cell death effects experienced by human podocytes cultured in the presence of NBL1. Of the monoclonal antibodies generated in Example 6, we tested 16 antibodies and assessed their ability to prevent cell death and apoptosis in human podocytes cultured in vivo.

Human podocytes were cultured in RPMI supplemented with 10% FBS and with ITS (1×). Human NBL1 recombinant protein was obtained from Genscript (Piscataway, NJ). Human monoclonal NBL1 antibodies obtained by cloning NBL1-binding phage-displayed Fabs into a human IgG1 format (Example 6 above) were tested at a concentration of 20 μg/ml.

The human podocytes were cultured for 48 hours in the presence/absence of human NBL1 (2 μg/ml) and in the presence/absence of our generated anti-NBL1 mAbs (20 μg/ml) at a ratio of 1:1 (mAbs: NBL1). Cell lysates were collected at 48 hours of culture, and cell death/apoptosis was assessed by using ELISA (Roche Diagnostics GmbH, 11544675001, Mannheim, Germany). Quantification of cell death was normalized to untreated cells.

We observed that following incubation in the presence of these newly generated mAbs, a number of the mAbs were able to prevent/reduce NBL1-induced cell death (p<0.0001) to varying degrees. Most importantly, 6 out of the 16 mAbs (YU1018-H08, YU1019-B06, YU1018-E01, YU1018-E04, YU1019-A12, YU1018-D06) were able to reduce the cell death effects experienced by human podocytes cultured in the presence of NBL1 to levels at or below the negative control (left-most bar, "Medium"), demonstrating that these mAbs are capable of completely neutralizing NBL1's pro-apoptotic effect on human podocytes in vitro, which further indicates that among the tested antibodies, these antibodies will most potently be able to reduce progression of glomerular/renal disease in subjects with elevated levels of circulating NBL1, including human subjects with T1D and T2D. Results are shown in FIG. 8.

In the same experiment, we tested the ability of soluble BMP2 (1 μg/ml, at a 1:1 BMP2: NBL1 ratio), to neutralize the effects of NBL1. As shown in FIG. 8, mAbs H08, B06, and E01 were significantly more robust in the reduction of NBL1-mediated apoptotic effects on human podocytes than sBMP2. This highlights the beneficial effectiveness of anti-NBL1 antibodies in protecting podocytes from NBL1-mediated toxicity and damage.

6.7. Example 7. NBL1 is Elevated in Type 1 Diabetes and Type 2 Diabetes

In order to determine whether NBL1 contributes to kidney damage in diabetes, NBL1 serum levels were assessed using an immunotargeted assay. NBL1 serum levels were measured in patients with long-standing type 1 diabetes (T1D, n=150) and compared with NBL1 serum levels observed in sera of non-diabetic subjects (n=15). NBL1 serum levels of patients with long-standing type 1 diabetes displayed a significant increase in NBL1. A parallel comparison of NBL1 serum levels in patients with type 2 diabetes (T2D, n=70) versus levels in non-diabetic subjects also displayed a significant increase in NBL1. Results are shown in FIG. 7A.

Subsequently, patients with T1D or T2D, and who had also received a diagnosis of diabetic kidney disease (DKD), were selected and we analyzed their NBL1 serum levels. The analysis demonstrated that patients with chronic kidney disease (CKD) at stage 2-3 (eGFR<60 ml/min/m$^2$, n=60) had a 3-fold increase in NBL1 serum levels as compared to non-diabetic subjects and a 2-fold increase in NBL1 serum levels as compared to diabetic patients without CKD (see FIG. 7B).

Inhibition of NBL1 is therefore a new therapeutic approach for preventing onset and progression of kidney damage in a patient with type 1 or type 2 diabetes. Inhibition of NBL1 will also be effective in treating non-diabetes glomerular diseases in which damage is mediated by NBL1.

7. EQUIVALENTS AND INCORPORATION BY REFERENCE

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents, and patent applications cited within the body of the instant specification are hereby incorporated by reference in their entirety, for all purposes.

What is claimed:

1. An antibody or antigen binding fragment thereof comprising three heavy chain variable region (VH) CDRs and three light chain variable region (VL) CDRs, wherein (a) the three VH CDRs respectively have the sequences of SEQ ID NO:93, SEQ ID NO:98, and SEQ ID NO:103, and (b) the three VL CDRs respectively have the sequences of SEQ ID NO:108, SEQ ID NO:113, and SEQ ID NO:118;

wherein the antibody or antigen binding fragment thereof is capable of binding to neuroblastoma suppressor of tumorgenicity 1 (NBL1).

2. The antibody or antigen binding fragment thereof of claim 1, comprising a VH having the sequence of SEQ ID NO:668.

3. The antibody or antigen binding fragment thereof of claim 1, comprising a VL having the sequence of SEQ ID NO:669.

4. The antibody or antigen binding fragment thereof of claim 1, comprising a VH having the sequence of SEQ ID NO:668 and a VL having the sequence of SEQ ID NO:669.

5. The antibody or antigen binding fragment of claim 4, wherein the antibody framework regions are human antibody framework regions.

6. The antibody or antigen binding fragment thereof of claim 1, wherein the antibody is a full length monospecific monoclonal antibody.

7. The antibody or antigen binding fragment thereof of claim 6, wherein the antibody is an IgG1, IgG2 or IgG4 antibody.

8. The antibody or antigen binding fragment thereof of claim 7, wherein the antibody is an IgG1 antibody.

9. The antibody or antigen binding fragment thereof of claim 7, wherein the antibody is humanized or fully human.

10. The antibody or antigen binding fragment thereof of claim 9, wherein the antibody comprises a human Fc region.

11. The antibody or antigen binding fragment thereof of claim 10, wherein the human Fc region has at least one engineered mutation that reduces antibody binding to an Fcγ receptor.

12. The antibody or antigen binding fragment thereof of claim 11, wherein the at least one engineered mutation is a N297A substitution.

13. The antibody or antigen binding fragment thereof of claim 10, wherein the human Fc region has at least one engineered mutation that reduces complement fixation.

14. The antibody or antigen binding fragment thereof of claim 13, wherein the at least one engineered mutation is K322A substitution.

15. A pharmaceutical composition, comprising:

(a) the antibody or antigen binding fragment thereof of claim 1, and (b) a pharmaceutically acceptable carrier.

16. A pharmaceutical composition, comprising:
(a) the antibody or antigen binding fragment thereof of claim 2, and
(b) a pharmaceutically acceptable carrier.
17. A pharmaceutical composition, comprising:
(a) the antibody or antigen binding fragment thereof of claim 3, and
(b) a pharmaceutically acceptable carrier.
18. A pharmaceutical composition, comprising:
(a) the antibody or antigen binding fragment thereof of claim 4, and
(b) a pharmaceutically acceptable carrier.
19. A pharmaceutical composition, comprising:
(a) the antibody or antigen binding fragment thereof of claim 5, and
(b) a pharmaceutically acceptable carrier.
20. A pharmaceutical composition, comprising:
(a) the antibody or antigen binding fragment thereof of claim 6, and
(b) a pharmaceutically acceptable carrier.
21. A pharmaceutical composition, comprising:
(a) the antibody or antigen binding fragment thereof of claim 7, and
(b) a pharmaceutically acceptable carrier.
22. A pharmaceutical composition, comprising:
(a) the antibody or antigen binding fragment thereof of claim 8, and
(b) a pharmaceutically acceptable carrier.
23. A pharmaceutical composition, comprising:
(a) the antibody or antigen binding fragment thereof of claim 9, and
(b) a pharmaceutically acceptable carrier.

24. A pharmaceutical composition, comprising:
(a) the antibody or antigen binding fragment thereof of claim 10, and
(b) a pharmaceutically acceptable carrier.
25. A pharmaceutical composition, comprising:
(a) the antibody or antigen binding fragment thereof of claim 11, and
(b) a pharmaceutically acceptable carrier.
26. A pharmaceutical composition, comprising:
(a) the antibody or antigen binding fragment thereof of claim 12, and
(b) a pharmaceutically acceptable carrier.
27. A pharmaceutical composition, comprising:
(a) the antibody or antigen binding fragment thereof of claim 13, and
(b) a pharmaceutically acceptable carrier.
28. A method for treating or delaying onset or progression of kidney damage in a subject who has type 1 or type 2 diabetes or a glomerular disease, the method comprising:
administering to the subject an effective amount of an antibody or antigen binding fragment thereof comprising three heavy chain variable region (VH) CDRs and three light chain variable region (VL) CDRs, wherein
(a) the three VH CDRs respectively have the sequences of SEQ ID NO:93, SEQ ID NO:98, and SEQ ID NO:103, and
(b) the three VL CDRs respectively have the sequences of SEQ ID NO:108, SEQ ID NO:113, and SEQ ID NO:118; and
wherein the antibody or antigen binding fragment thereof is capable of inhibiting neuroblastoma suppressor of tumorgenicity 1 (NBL1) activity.

\* \* \* \* \*